(12) United States Patent
Claffey et al.

(10) Patent No.: US 8,278,295 B2
(45) Date of Patent: Oct. 2, 2012

(54) AMINO-HETEROCYCLIC COMPOUNDS

(75) Inventors: Michelle M. Claffey, Stonington, CT (US); Christopher J. Helal, East Lyme, CT (US); Patrick R. Verhoest, Old Lyme, CT (US)

(73) Assignee: Pfizer Inc., New York, NY (US)

( * ) Notice: Subject to any disclaimer, the term of this patent is extended or adjusted under 35 U.S.C. 154(b) by 200 days.

(21) Appl. No.: 12/693,480

(22) Filed: Jan. 26, 2010

(65) Prior Publication Data

US 2010/0190771 A1    Jul. 29, 2010

Related U.S. Application Data

(60) Provisional application No. 61/206,092, filed on Jan. 26, 2009.

(51) Int. Cl.
| | | |
|---|---|---|
| *A01N 43/00* | (2006.01) | |
| *A01N 43/90* | (2006.01) | |
| *A61K 31/00* | (2006.01) | |
| *A61K 31/519* | (2006.01) | |
| *C07D 487/00* | (2006.01) | |

(52) U.S. Cl. ............... 514/210.21; 514/262.1; 544/262

(58) Field of Classification Search .................. None
See application file for complete search history.

(56) References Cited

U.S. PATENT DOCUMENTS 6,235,742 B1    5/2001  Bell et al. .................. 514/258
7,262,186 B2 *  8/2007  Fraley et al. ............... 514/218

FOREIGN PATENT DOCUMENTS

| WO | WO 03037432 | 5/2003 |
|---|---|---|
| WO | WO 03037899 | 5/2003 |
| WO | 2008139293 | 11/2008 |
| WO | WO 2009121919 | 10/2009 |

OTHER PUBLICATIONS

Boess et al., Neuropharmacology, vol. 47, (2004). pp. 1081-1092.
Martin Hendrix, BMC Pharmacology, 2005, vol. 5(Suppl 1): 55.
Bol'But, A.V., et al., "Condensed Pyrimidine Systems, 5.6-methyl-functionalized in pyrazolo [3,4-d]pyrimidin-4(5H)-ones", Chemical Abstract Service, 2007, Zhurnal Organichnoi TA Farmatsevtichnoi Khimii, Zofkam,2006, pp. 57-61, 4(4).
PCT/IB2010/050133, International Search Report, Mail date Apr. 20, 2010, 7 pages, PC33470A.

* cited by examiner

*Primary Examiner* — Jeffrey Murray
(74) *Attorney, Agent, or Firm* — Martha G. Munchhof

(57) ABSTRACT

The invention provides PDE9-inhibiting compounds of Formula (I),

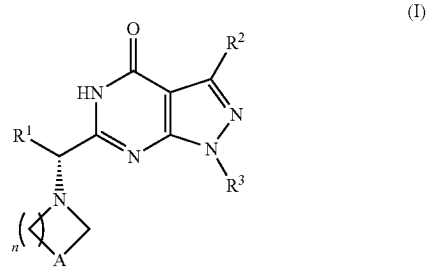

and pharmaceutically acceptable salts thereof, wherein $R^1$, $R^2$, $R^3$, A, and n are as defined herein. Pharmaceutical compositions containing the compounds of Formula I, and uses thereof in treating neurodegenerative and cognitive disorders, such as Alzheimer's disease and schizophrenia, are also provided.

11 Claims, No Drawings

AMINO-HETEROCYCLIC COMPOUNDS

FIELD OF THE INVENTION

This invention relates to a series of novel compounds that are selective inhibitors of phosphodiesterase type 9 ("PDE9"). More particularly, the invention relates to pyrazolo[3,4-d]pyrimidinone compounds for use in the treatment and prevention of neurodegenerative diseases and other diseases and disorders influenced by modulation of PDE9.

BACKGROUND OF THE INVENTION

Cyclic nucleotides cyclic guanosine monophosphate (cGMP) and cyclic adenosine monophosphate (cAMP) are important second messengers and thus are central to the control and regulation of a multitude of cellular events, both physiological and pathophysiological, in a wide variety of organs.

Cyclic GMP is formed from GTP by the catalytic reaction of guanylyl cyclase (GC), which is activated by nitric oxide (NO). Cyclic GMP in turn activates cGMP-dependent protein kinases (cGK), which mediate local and global signaling. A variety of physiological processes in the cardiovascular, nervous and immune systems are controlled by the NO/cGMP pathway, including ion channel conductance, glycogenolysis, cellular apoptosis, and smooth muscle relaxation. In blood vessels, relaxation of vascular smooth muscles leads to vasodilation and increased blood flow.

The phosphodiesterase (PDE) enzyme family hydrolyzes cGMP and cAMP. The PDE9 enzyme has been identified as a novel member of the PDE enzyme family that selectively hydrolyzes cGMP over cAMP. See Fisher et al., *J. Biol. Chem.*, 273(25), 15559-15564 (1998). PDE9 has been found to be present in a variety of human tissues, namely the testes, brain, small intestine, skeletal muscle, heart, lung, thymus and spleen, as well as in smooth muscle cells within the human vasculature of a variety of tissues.

Recent studies have directly implicated dysfunction of NO/cGMP/cGK signaling in Alzheimer's disease. For example, disruption of Long Term Potentiation (LTP), a physiological correlate of learning and memory, by amyloid-β peptide was shown to result from a malfunction of NO/cGMP signaling. Puzzo et al., *J. Neurosci.*, 25(29):6887-6897 (2005). Moreover, in rats showing deficits in memory tasks due to depletion in forebrain acetylcholinesterase (which is associated with Alzheimer's disease), administration of a nitric oxide mimetic increased GC activity and reversed the cognitive deficits in memory tasks. Bennett et al., *Neuropsychopharmacology*, 32:505-513 (2007). It is therefore believed that therapeutic agents capable of enhancing the GC/NO/cGMP/cGK signaling cascade may be useful as a new approach to the treatment of Alzheimer's disease and other neurodegenerative disorders.

By reducing or preventing the hydrolysis of cGMP by PDE9, PDE9 inhibitors elevate the intracellular level of cGMP, thus enhancing or prolonging its effects. It has been found that an increase in cGMP concentration in rats leads to improvement in learning and memory in social and object recognition tests. See, e.g., Boess et al., *Neuropharmacology*, 47:1081-1092 (2004). Inhibition of PDE9 has been shown to increase LTP. Hendrix, *BMC Pharmacol.*, 5(Supp 1):55 (2005).

Accordingly, there is a need for PDE9 inhibitors that are effective in treating conditions that may be regulated or normalized by inhibition of PDE9.

SUMMARY OF THE INVENTION

The present invention is directed to compounds of Formula (I),

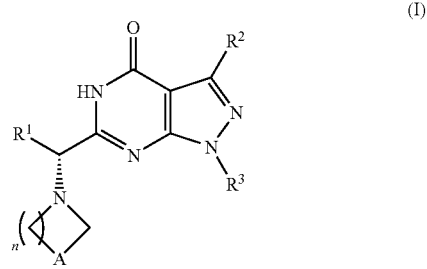

and pharmaceutically acceptable salts thereof, wherein $R^1$, $R^2$, $R^3$, A and n are as defined herein.

The present invention is also directed to pharmaceutical compositions containing a compound of Formula (I), or a pharmaceutically acceptable salt thereof, and a pharmaceutically acceptable vehicle, carrier or diluent, and optionally further comprising a second pharmaceutical agent.

The present invention is further directed to a method of inhibiting PDE9 in a mammal in need of such inhibition, comprising the step of administering to the mammal a PDE9-inhibiting amount of a) a compound of Formula I, or a pharmaceutically acceptable salt thereof; or b) a pharmaceutical composition comprising a compound of Formula I, or a pharmaceutically acceptable salt thereof, and a pharmaceutically acceptable vehicle, carrier or diluent.

The present invention is further directed to a method of treating a neurodegenerative disease in a mammal in need of such treatment, comprising the step of administering to the mammal a therapeutically effective amount of a compound of Formula I, or a pharmaceutically acceptable salt thereof.

The present invention is further directed to a method of promoting neurorestoration in a mammal in need of such neurorestoration, comprising the step of administering to the mammal a therapeutically effective amount of a compound of Formula I, or a pharmaceutically acceptable salt thereof.

The present invention is still further directed to a method of promoting functional recovery in a mammal suffering from an injury of the brain, comprising the step of administering to the mammal a therapeutically effective amount of a compound of Formula I, or a pharmaceutically acceptable salt thereof.

The present invention is still further directed to a method of improving cognitive deficits and treating cognitive impairment in a mammal in need of such improvement or treatment, comprising the step of administering to the mammal a therapeutically effective amount of a compound of Formula I, or a pharmaceutically acceptable salt thereof.

The present invention is still further directed to a method of enhancing cognition in a mammal in need of such enhancement, comprising the step of administering to the mammal a cognition-enhancing amount of a compound of Formula I, or a pharmaceutically acceptable salt thereof.

With the foregoing and other advantages and features of the invention that will become hereinafter apparent, the nature of the invention may be more clearly understood by reference to the following detailed description of the invention and the appended claims.

DETAILED DESCRIPTION OF THE INVENTION

The present invention comprises novel selective PDE9 inhibitors of Formula (I),

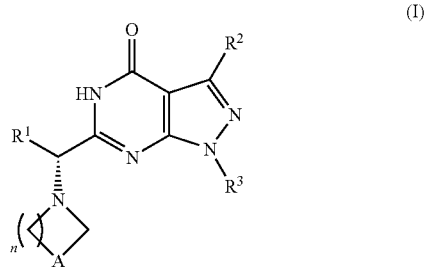

and pharmaceutically acceptable salts thereof, wherein:

$R^1$ is selected from the group consisting of (i) hydrogen, (ii) $(C_1-C_4)$alkyl, (iii) $(C_2-C_4)$alkenyl, (iv) $(C_2-C_4)$alkynyl, (v) $(C_1-C_4)$alkoxy, (vi) $(C_1-C_4)$haloalkyl, (vii) $(C_3-C_6)$cycloalkyl, optionally substituted with one to three substituents, the substituents being independently selected from the group consisting of $(C_1-C_4)$alkyl, $(C_1-C_4)$alkoxy, halo, $(C_1-C_4)$haloalkyl, $(C_1-C_4)$haloalkoxy, cyano, carboxy, and carbamoyl, (viii) 4 to 10 member heterocycloalkyl, optionally substituted with one to three substituents, the substituents being independently selected from the group consisting of $(C_1-C_4)$alkyl, $(C_1-C_4)$alkoxy, halo, $(C_1-C_4)$haloalkyl, $(C_1-C_4)$haloalkoxy, cyano, carboxy, and carbamoyl, (ix) aryl, optionally substituted with one to three substituents, the substituents being independently selected from the group consisting of $(C_1-C_4)$alkyl, $(C_1-C_4)$alkoxy, halo, $(C_1-C_4)$haloalkyl, $(C_1-C_4)$haloalkoxy, cyano, carboxy, and carbamoyl, and (x) heteroaryl, optionally substituted with one to three substituents, the substituents being independently selected from the group consisting of $(C_1-C_4)$alkyl, $(C_1-C_4)$alkoxy, halo, $(C_1-C_4)$haloalkyl, $(C_1-C_4)$haloalkoxy, cyano, carboxy, and carbamoyl;

$R^2$ is selected from the group consisting of hydrogen, $(C_1-C_4)$alkyl, $(C_1-C_4)$haloalkyl, cyano, and $(C_3-C_6)$cycloalkyl;

$R^3$ is selected from the group consisting of $(C_1-C_6)$alkyl, $(C_2-C_6)$alkenyl, $(C_2-C_6)$alkynyl, $(C_3-C_8)$cycloalkyl, heterocycloalkyl, aryl, and heteroaryl, each of which optionally may be substituted with one to three substituents, the substituents being independently selected from the group consisting of $(C_1-C_4)$alkyl, $(C_1-C_4)$alkoxy, halo, and $(C_1-C_4)$haloalkyl;

n is 1 or 2;

A is $-CR^4R^5-$ or $-CHR^a-CHR^b-$;

$R^4$ is selected from the group consisting of (i) hydrogen, (ii) $(C_1-C_7)$alkyl, (iii) $(C_3-C_8)$cycloalkyl, (iv) 4 to 10 member heterocycloalkyl, (v) aryl, optionally substituted with one to three substituents, the substituents being independently selected from the group consisting of $(C_1-C_4)$alkyl, $(C_1-C_4)$alkoxy, halo, $(C_1-C_4)$haloalkyl, $(C_1-C_4)$haloalkoxy, $(C_3-C_6)$cycloalkyl, cyano, carboxy, and carbamoyl, (vi) heteroaryl, optionally substituted with one to three substituents, the substituents being independently selected from the group consisting of $(C_1-C_4)$alkyl, $(C_1-C_4)$alkoxy, halo, $(C_1-C_4)$haloalkyl, $(C_1-C_4)$haloalkoxy, $(C_3-C_6)$cycloalkyl, cyano, carboxy, and carbamoyl, and (vii) $LR^6$, wherein:

L is selected from the group consisting of $-CH_2-$, $-NR^7-$, and $-O-$;

$R^6$ is aryl, heteroaryl, $(C_1-C_8)$alkyl, $(C_3-C_8)$cycloalkyl, 4 to 10 member heterocycloalkyl, or $(C_1-C_8)$alkoxy, each of which optionally may be substituted with one to three substituents, the substituents being independently selected from the group consisting of $(C_1-C_4)$alkyl, $(C_1-C_4)$alkoxy, halo, $(C_1-C_4)$haloalkyl, $(C_1-C_4)$haloalkoxy, $(C_3-C_6)$cycloalkyl, cyano, carboxy, and carbamoyl; and $R^7$ is hydrogen, methyl or ethyl;

$R^5$ is selected from the group consisting of hydrogen, hydroxyl, $(C_1-C_4)$alkoxy, halogen, and $(C_1-C_6)$alkyl; or $R^4$ and $R^5$, together with the carbon to which they are attached, form a cycloalkyl or heterocycloalkyl ring that optionally incorporates an oxo group and is optionally substituted with $(C_1-C_8)$alkyl, $(C_3-C_8)$cycloalkyl, halo, $(C_1-C_8)$alkoxy, or $(C_1-C_3)$haloalkyl;

$R^a$ is $(C_1-C_4)$alkoxy or $R^8-O-C(O)-$, wherein $R^8$ is $(C_1-C_4)$alkyl; and $R^b$ is aryl, heteroaryl, or heterocycloalkyl, optionally substituted with halo, $(C_1-C_8)$alkyl, $(C_3-C_8)$cycloalkyl, $(C_1-C_8)$alkoxy, or $(C_1-C_3)$haloalkyl; or $R^a$ and $R^b$, together with the carbons to which they are attached, form a cycloalkyl or heterocycloalkyl ring that optionally incorporates an oxo group and is optionally substituted with $(C_1-C_8)$alkyl, $(C_3-C_8)$cycloalkyl, halo, $(C_1-C_8)$alkoxy, or $(C_1-C_3)$haloalkyl.

In one embodiment of the compounds of formula I, $R^1$ is selected from the group consisting of $(C_1-C_4)$alkyl, $(C_3-C_6)$cycloalkyl, $(C_1-C_4)$haloalkyl, optionally substituted 4 to 10 member heterocycloalkyl, optionally substituted aryl, and optionally substituted heteroaryl.

In another embodiment, $R^2$ is selected from the group consisting of hydrogen, $(C_1-C_4)$alkyl, $(C_1-C_4)$haloalkyl, cyano, and cyclopropyl.

In another embodiment, $R^4$ is selected from the group consisting of (i) hydrogen, (ii) aryl, optionally substituted with one to three substituents, the substituents being independently selected from the group consisting of $(C_1-C_4)$alkyl, $(C_1-C_4)$alkoxy, halo, $(C_1-C_4)$haloalkyl, $(C_1-C_4)$haloalkoxy, $(C_3-C_8)$cycloalkyl, cyano, carboxy, and carbamoyl, (iii) heteroaryl, optionally substituted with one to three substituents, the substituents being independently selected from the group consisting of $(C_1-C_4)$alkyl, $(C_1-C_4)$alkoxy, halo, $C_1-C_4$)haloalkyl, $(C_1-C_4)$haloalkoxy, $(C_3-C_6)$cycloalkyl, cyano, carboxy, and carbamoyl, and (iv) $LR^6$, wherein L is selected from the group consisting of $-CH_2-$, $-NR^7-$, and $-O-$; and $R^6$ is aryl or heteroaryl, each of which optionally may be substituted with one to three substituents, the substituents being independently selected from the group consisting of $(C_1-C_4)$alkyl, $(C_1-C_4)$alkoxy, halo, $(C_1-C_4)$haloalkyl, $(C_1-C_4)$haloalkoxy, $(C_3-C_6)$cycloalkyl, cyano, carboxy, and carbamoyl.

In another embodiment, $R^4$ is as described above, and $R^5$ is selected from the group consisting of hydrogen, hydroxyl, $(C_1-C_4)$alkoxy, halo, and $(C_1-C_6)$alkyl; or $R^4$ and $R^5$, together with the carbon to which they are attached, form a cyclic ketone.

In another embodiment $R^a$ is as described above, and $R^b$ is aryl or heteroaryl, optionally substituted with halo, $(C_1-C_3)$alkyl, or $(C_1-C_3)$haloalkyl; or $R^a$ and $R^b$, together with the carbons to which they are attached, form a cycloalkyl or heterocycloalkyl ring that optionally incorporates an oxo group and is optionally substituted with $(C_1-C_8)$alkyl, $(C_3-C_8)$cycloalkyl, halo, $(C_1-C_8)$alkoxy, or $(C_1-C_3)$haloalkyl.

Another embodiment of the compounds of formula I includes those compounds wherein $R^1$ is $(C_1-C_4)$alkyl, $(C_3-C_6)$cycloalkyl, or phenyl; $R^2$ is hydrogen; $R^3$ is selected from the group consisting of isopropyl, cyclobutyl, cyclopentyl, tetrahydrofuranyl, and tetrahydropyranyl; A is $CR^4R^5$; and L is $-CH_2-$ or $-O-$.

In other specific embodiments, the invention also relates to the compounds described as Examples 1-175 in the Examples section of the subject application, and pharmaceutically acceptable salts thereof.

The compounds of the invention have been surprisingly found to show pharmacological activity, including selective inhibition of PDE9, that makes them suitable for the treatment, prevention and/or control of conditions that may be regulated or normalized by inhibition of PDE9.

The compounds and intermediates of the present invention may be named according to either the IUPAC (International Union for Pure and Applied Chemistry) or CAS (Chemical Abstracts Service, Columbus, Ohio) nomenclature systems.

Definitions

Certain terms used herein are generally defined as follows:

The carbon atom content of the various hydrocarbon-containing moieties herein may be indicated by a prefix designating the minimum and maximum number of carbon atoms in the moiety. Thus, for example, $(C_1-C_6)$alkyl refers to an alkyl group of one to six carbon atoms inclusive.

The term "alkoxy" refers to a straight or branched, monovalent, saturated aliphatic hydrocarbon radical bonded to an oxygen atom that is attached to a core structure. Examples of alkoxy groups include methoxy, ethoxy, propoxy, isopropoxy, butoxy, isobutoxy, tert-butoxy, pentoxy, and the like.

The term "alkyl" means a saturated monovalent straight or branched aliphatic hydrocarbon radical. Examples of alkyl groups include methyl, ethyl, propyl, isopropyl, butyl, isobutyl, tent-butyl, sec-butyl, pentyl, isopentyl, neopentyl, hexyl, isohexyl, and the like.

The term "alkenyl" means a partially unsaturated straight or branched aliphatic hydrocarbon radical having one or more double bonds. Examples of alkenyl groups include ethenyl (also known as "vinyl"), allyl, 1-propenyl, isopropenyl, n-butenyl, n-pentenyl, and the like. The term "alkenyl" embraces radicals having "cis" and "trans" orientations, or alternatively, "Z" and "E" orientations.

The term "alkynyl" means a partially unsaturated straight or branched aliphatic hydrocarbon radical having one or more triple bonds. Examples of alkynyl groups include 1-propynyl, 2-propynyl (also known as "propargyl"), 1-butynyl, 2-butynyl, 1-pentynyl, and the like.

The term "aryl" denotes a monocyclic or polycyclic aromatic ring system, for example, anthracenyl, benzyl, fluorenyl, indenyl, naphthyl, phenanthrenyl, phenyl and the like. The term "aryl" is also intended to include the partially hydrogenated derivatives of such ring systems, e.g. 1,2,3,4-tetrahydronaphthyl.

The term "aryloxy" denotes an aryl radical bonded to an oxygen atom that is attached to a core structure, such as benzyloxy.

The terms "carbamoyl" and "carbamyl" denote an amino group (—NR'R") bonded to a carbonyl group (C=O) that is attached to a core structure.

The term "cycloalkyl" denotes a saturated monocyclic or bicyclic cycloalkyl group. Examples of cycloalkyl groups include cyclopropyl, cyclobutyl, cyclopentyl, cyclohexyl, cycloheptyl, cyclooctyl, and the like.

The terms "halogen" and "halo" represent chlorine, bromine, fluorine and iodine atoms and radicals.

The term "haloalkyl" refers to an alkyl or cycloalkyl substituent wherein at least one hydrogen radical is replaced with a halogen radical. Where more than one hydrogen is replaced with halogen, the halogens may be the same or different. Examples of haloalkyl radicals include trifluoromethyl, 2,2,2-trifluoroethyl, 4,4,4-trifluorobutyl, 4,4-difluorocyclohexyl, chloromethyl, dichloromethyl, trichloromethyl, 1-bromoethyl, and the like.

The term "haloalkoxy" refers to an alkoxy radical in which at least one hydrogen radical is replaced with a halogen radical. Where more than one hydrogen is replaced with halogen, the halogens may be the same or different. Examples of haloalkoxy radicals include difluoromethoxy, trifluoromethoxy, 2,2,2-trifluoroethoxy, chloromethoxy, bromomethoxy, and the like.

The term "heteroaryl" as used herein includes heterocyclic unsaturated ring systems containing one or more heteroatoms such as nitrogen, oxygen, and sulfur. If the heteroaryl group contains more than one heteroatom, the heteroatoms may be the same or different. The heteroaryl radicals may be bonded via a carbon atom or a heteroatom. The term "heteroaryl" is also intended to include the partially hydrogenated derivatives of such ring systems. Examples of heteroaryl groups include furanyl (also known as "furyl"), imidazolinyl, imidazolyl (also known as "1,3-diazolyl"), indolyl, oxadiazolyl, oxazinyl, oxazolyl, isoxazolyl, pyranyl, pyrazinyl (also known as "1,4-diazinyl"), pyrazolyl (also known as "1,2-diazolyl"), pyrazolinyl, pyrazyl, pyridazinyl (also known as "1,2-diazinyl"), pyridyl (also known as pyridinyl), pyrimidinyl (also known as "1,3-diazinyl" and "pyrimidyl"), pyrrolyl, thiadiazinyl, thiadiazolyl, thiatriazolyl, thiazolyl, isothiazolyl, thienyl, thiofuranyl (also known as "thiophenyl"), thiopyranyl, triazinyl, triazolyl, and the like.

The term "heteroaryl" also embraces radicals in which 2 or 3 rings are fused together, wherein at least on such ring contains a heteroatom as a ring atom, including radicals wherein (a) a heterocycloalkyl (or heterocyclic ketone) ring is fused with an aryl or heteroaryl ring, or (b) a cycloalkyl (or cyclic ketone) ring is fused with a heteroaryl ring. Examples of 2-fused ring heteroaryls include benzodioxinyl, dihydrobenzodioxinyl, benzofuranyl, dihydrobenzofuranyl, isobenzofuranyl, benzimidazolyl, benzothiadiazolyl, tetrahydrobenzothiadiazolyl, benzothiazolyl, benzothienyl (also known as "benzothiophenyl," "thionaphthenyl," and "benzothiofuranyl"), benzoxazinyl, dihydrobenzoxazinyl, benzoxazolyl, chromanyl, isochromanyl, chromenyl, cinnolinyl (also known as "1,2-benzodiazinyl"), imidazopyridinyl (e.g. imidazo[1,2-a]pyridinyl or imidazo[4,5-d]pyridinyl), indazolyl, indolinyl, isoindolinyl, indolizinyl, indolyl, isoindolyl, naphthyridinyl, oxathiolopyrrolyl, pteridinyl, pthalazinyl, purinyl (also known as "imidazo[4,5-d]pyrimidinyl"), pyranopyrrolyl, pyrazoloazepinyl, tetrahydropyrazoloazepinyl (e.g. tetrahydropyrazolo[1,5-a]azepinyl), pyrazolopyridinyl, tetrahydropyrazolopyridinyl (e.g. tetrahydropyrazolo[1,5-a]pyridinyl), pyrazolopyrimidinyl (e.g. pyrazolo[3,4-d]pyrimidinyl), pyridopyrazinyl (e.g. pyrido[2,3-b]pyrazinyl), pyridopyridinyl, pyrrolopyrazolyl, dihydropyrrolopyrazolyl (e.g. dihydropyrrolo[1,2-b]pyrazolyl), quinazolinyl (also known as "1,3-benzodiazinyl"), quinolinyl (also known as "1-benzazinyl"), isoquinolinyl (also known as "2-benzazinyl"), quinolizinyl, quinolyl, isoquinolyl, quinoxalinyl, dithianaphthalenyl, thienofuranyl (e.g. thieno[3,2-b]furanyl), and the like.

Examples of 3-fused ring heteroaryls include acridinyl, diazaanthryl, triazaphenanthrene, carbazdyl, carbolinyl, furocinnolinyl, perimidinyl, phenanthridinyl, phenanthrolinyl, phenazinyl, phenothiazinyl, phenoxathiinyl, phenoxazinyl, thianthrenyl, xanthenyl, and the like.

The term "heterocycloalkyl" denotes a saturated monocyclic or polycyclic cycloalkyl group, in which at least one of the carbon atoms is replaced with a heteroatom such as nitrogen, oxygen or sulfur. If the heterocycle contains more than one heteroatom, the heteroatoms may be the same or different. The heterocycloalkyl radicals may be bonded via a carbon atom or a heteroatom. Preferably, the heterocycloalkyl radical has 4 to 10 members. Examples of heterocycloalkyl groups include azetidinyl, dioxacyclohexyl, 1,3-dioxolanyl, imidazolidinyl, morpholinyl, piperazinyl, piperidinyl, pyrazolidinyl, pyrrolidinyl, tetrahydrofuranyl, tetrahydropyranyl, tetrahydrothiopyranyl, thiazanyl, and the like.

A cyclic group may be bonded to another group in more than one way. If no particular bonding arrangement is specified, then all possible arrangements are intended. For example, the term "pyridyl" includes 2-, 3- or 4-pyridyl (2-, 3-, or 4-pyridinyl).

The term "mammal" means animals including, for example, dogs, cats, cows, sheep, goats, horses and humans. Preferred mammals include humans.

The term "oxo" means a carbonyl (C=O) group formed by the combination of a carbon atom and an oxygen atom.

The term "patient" includes both human and non-human patients.

The phrase "pharmaceutically acceptable" indicates that the designated carrier, vehicle, diluent, and/or salt is generally chemically and/or physically compatible with the other ingredients comprising the formulation, and physiologically compatible with the recipient thereof.

The term "salts" refers to both organic and inorganic salts of a compound of Formula (I). Such salts can be prepared in situ during the final isolation and purification of a compound, or by separately reacting a compound, prodrug or stereoisomer of Formula (I) with a suitable organic or inorganic acid or base and isolating the salt thus formed. Representative anionic salts include bromide, chloride, iodide, sulfate, bisulfate, nitrate, acetate, trifluoroacetate, oxalate, besylate, palmitate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthoate, naphthalate, mesylate, glucoheptonate, lactobionate and laurylsulphonate salts and the like. Representative cationic salts include sodium, potassium, calcium, and magnesium salts and the like. See generally, e.g., Berge, et al., *J. Pharm. Sci.*, 66, 1-19 (1977).

A salt of a compound of Formula (I) may be readily prepared by mixing together solutions of a compound of Formula (I) and the desired acid or base, as appropriate. The salt may precipitate from solution and be collected by filtration or may be recovered by evaporation of the solvent.

The term "radical" denotes a group of atoms that behaves as a single reactant in a chemical reaction, e.g., an organic radical is a group of atoms that imparts characteristic properties to a compound containing it, or which remains unchanged during a series of reactions or transformations.

The phrase "reaction-inert solvent" or "inert solvent" refers to a solvent, or mixture of solvents, that does not interact with starting materials, reagents, intermediates or products in a manner that adversely affects their desired properties.

The terms "treat," "treating," "treated" or "treatment" as used herein includes preventative (e.g., prophylactic), palliative or curative uses or results.

The compounds of Formula (I) may contain asymmetric or chiral centers and, therefore, exist in different stereoisomeric forms. Those skilled in the art will appreciate that, unless otherwise specified, all stereoisomers (e.g., enantiomers and diastereoisomers, and racemic mixtures thereof) of the novel compounds and intermediates described, illustrated and/or discussed herein are within the scope of the claimed invention. In addition, unless otherwise specified, the present invention embraces all geometric and positional isomers.

Diastereomeric mixtures can be separated into their individual diastereomers on the basis of their physical chemical differences by methods well-known to those of ordinary skill in the art, such as by chromatography and/or fractional crystallization. Enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. Additional methods include resolution of racemic mixtures using chiral salts, as well as chiral chromatography.

Those skilled in the art will further recognize that the compounds of Formula (I) can exist in crystalline form as hydrates wherein molecules of water are incorporated within the crystal structure thereof and as solvates wherein molecules of a solvent are incorporated therein. All such hydrate and solvate forms are considered part of this invention.

Practitioners will appreciate that certain compounds of Formula (I) may exist as tautomeric isomers, i.e., that equilibrium exists between two isomers which are in rapid equilibrium with each other. A common example of tautomerism is keto-enol tautomerism, i.e.,

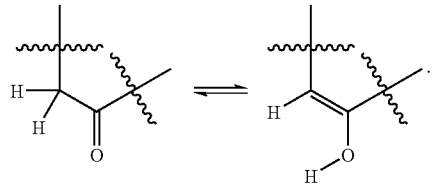

The degree to which one tautomer is present over the other depends upon various factors, including substitution pattern and solvent type. Other examples in accordance with the present invention will be recognized by those skilled in the art. All tautomeric forms of Formula (I) are included within the scope of the invention unless otherwise specified.

The present invention also embraces isotopically-labeled compounds of Formula (I) that are identical to those recited herein, but for the fact that one or more atoms are replaced by an atom having an atomic mass or mass number different from the atomic mass or mass number usually found in nature. Examples of isotopes that can be incorporated into compounds of Formula (I) include isotopes of hydrogen, carbon, nitrogen, oxygen, sulfur, phosphorus, fluorine, and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. The compounds of Formula (I), and pharmaceutically acceptable salts thereof, that contain the aforementioned isotopes and/or other isotopes of the other atoms are within the scope of the instant invention.

Certain isotopically-labeled compounds of Formula (I), for example those into which radioactive isotopes such as $^{3}H$ and $^{14}C$ are incorporated, are useful in drug and/or substrate tissue distribution assays. Tritiated, i.e. $^{3}H$, and $^{14}C$ isotopes are particularly preferred for their ease of preparation and detectability. Furthermore, substitution with heavier isotopes such as deuterium, i.e. $^{2}H$, may afford certain therapeutic advantages resulting from greater metabolic stability, for example, increased in vivo half-life, or reduced dosage requirements and, hence, may be preferred in some circumstances. Isotopically-labeled compounds of Formula (I), and pharmaceutically acceptable salts thereof, can be generally prepared by carrying out analogous procedures to those disclosed in the Schemes and/or in the Examples below, by substituting a readily available isotopically-labeled reagent for a non-isotopically labeled reagent.

The invention also includes pharmaceutical compositions comprising an amount of a compound of Formula (I), or a pharmaceutically acceptable salt of the compound, and optionally a pharmaceutically acceptable vehicle, carrier or diluent. In a preferred embodiment, the pharmaceutical composition is of an amount effective at inhibiting the enzyme PDE9 in a mammal. In another preferred embodiment, the mammal is a human.

The present invention includes the use of a combination of a PDE9 inhibitor compound as provided in Formula (I) and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula (I) or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of Formula (I), depending on the disease, disorder, or condition to be treated. Pharmaceutically active agents that may be used in combination with the compositions of the present invention include, without limitation:

(i) acetylcholinesterase inhibitors, such as donepezil hydrochloride (ARICEPT, MEMAC), physostigmine salicylate (ANTILIRIUM), physostigmine sulfate (ESERINE), metrifonate, neostigmine, ganstigmine, pyridostigmine (MESTINON), ambenonium (MYTELASE), demarcarium, Debio 9902 (also known as ZT-1; Debiopharm), rivastigmine (EXELON), ladostigil, NP-0361, galantamine hydrobromide (RAZADYNE, RIMINYL, NIVALIN), tacrine (COGNEX), tolserine, velnacrine maleate, memoquin, huperzine A (HUP-A; NeuroHitech), phenserine, and edrophonium (ENLON, TENSILON);

(ii) amyloid-β (or fragments thereof), such as Aβ$_{1-15}$ conjugated to pan HLA, DR-binding epitope (PADRE), ACC-001 (Elan/Wyeth), ACI-01, ACI-24, AN-1792, Affitope AD-01, CAD106, and V-950;

(iii) antibodies to amyloid-β (or fragments thereof), such as bapineuzumab (also known as AAB-001), AAB-002 (Wyeth/Elan), ACI-01-Ab7, BAN-2401, intravenous Ig (GAMMAGARD), LY2062430 (humanized m266; Lilly), PF-04360365 (also known as RN-1219; Pfizer), RN-6G (Pfizer), R1450 (Roche), ACU-5A5, huC091, and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(iv) amyloid-lowering or -inhibiting agents (including those that reduce amyloid production, accumulation and fibrillization) such as colostrinin, bisnorcymserine (also known as BNC), NIC5-15 (Humanetics), E-2012 (Eisai), pioglitazone, clioquinol (also known as PBT1), PBT2 (Prana Biotechnology), flurbiprofen (ANSAID, FROBEN) and its R-enantiomer tarenflurbil (FLURIZAN), nitroflurbiprofen, fenoprofen (FENOPRON, NALFON), ibuprofen (ADVIL, MOTRIN, NUROFEN), ibuprofen lysinate, meclofenamic acid, meclofenamate sodium (MECLOMEN), indomethacin (INDOCIN), diclofenac sodium (VOLTAREN), diclofenac potassium, sulindac (CLINORIL), sulindac sulfide, diflunisal (DOLOBID), naproxen (NAPROSYN), naproxen sodium (ANAPROX, ALEVE), ARC031 (Archer Pharmaceuticals), CAD-106 (Cytos), LY450139 (Lilly), insulin-degrading enzyme (also known as insulysin), the gingko biloba extract EGb-761 (ROKAN, TEBONIN), tramiprosate (CEREBRIL, ALZHEMED), eprodisate (FIBRILLEX, KIACTA), compound W (3,5-bis(4-nitrophenoxy)benzoic acid), NGX-96992, neprilysin (also known as neutral endopeptidase (NEP)), scyllo-inositol (also known as scyllitol), atorvastatin (LIPITOR), simvastatin (ZOCOR), KLVFF-(EEX)3, SKF-74652, ibutamoren mesylate, and RAGE (receptor for advanced glycation end-products) inhibitors, such as TTP488 (also known as PF-4494700; Transtech) and TTP4000 (Transtech), and those disclosed in U.S. Pat. No. 7,285,293, including PTI-777;

(v) alpha-adrenergic receptor agonists, such as clonidine (CATAPRES), metaraminol (ARAMINE), methyldopa (ALDOMET, DOPAMET, NOVOMEDOPA), tizanidine (ZANAFLEX), phenylephrine (also known as neosynephrine), methoxamine, cirazoline, guanfacine (INTUNIV), lofexidine, xylazine, modafinil (PROVIGIL), adrafinil, and armodafinil (NUVIGIL);

(vi) beta-adrenergic, receptor blocking agents (beta blockers), such as carteolol, esmolol (BREVIBLOC), labetalol (NORMODYNE, TRANDATE), oxprenolol (LARACOR, TRASACOR), pindolol (VISKEN), propanolol (INDERAL), sotalol (BETAPACE, SOTALEX, SOTACOR), timolol (BLOCADREN, TIMOPTIC), acebutolol (SECTRAL, PRENT), nadolol (CORGARD), metoprolol tartrate (LOPRESSOR), metoprolol succinate (TOPROL-XL), atenolol (TENORMIN), butoxamine, and SR 59230A (Sanofi);

(vii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE, tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(viii) anticonvulsants, such as carbamazepine (TEGRETOL, CARBATROL), oxcarbazepine (TRILEPTAL), phenyloin sodium (PHENYTEK), fosphenyloin (CEREBYX, PRODILANTIN), divalproex sodium (DEPAKOTE), gabapentin (NEURONTIN), pregabalin (LYRICA), topiramate (TOPAMAX), valproic acid (DEPAKENE), valproate sodium (DEPACON), 1-benzyl-5-bromouracil, progabide, beclamide, zonisamide (TRERIEF, EXCEGRAN), CP-465022, retigabine, talampanel, and primidone (MYSOLINE);

(ix) antipsychotics, such as lurasidone (also known as SM-13496; Dainippon Sumitomo), aripiprazole (ABILIFY), chlorpromazine (THORAZINE), haloperidol (HALDOL), iloperidone (FANAPTA), flupentixol decanoate (DEPIXOL, FLUANXOL), reserpine (SAPLESS), pimozide (ORAP), fluphenazine decanoate, fluphenazine hydrochloride, prochlorperazine (COMPRO), asenapine (SAPHRIS), abaperidone, loxapine (LOXITANE), mesoridazine, molindone (MOBAN), perphenazine, thioridazine, thiothixine, trifluoperazine (STELAZINE), clozapine (CLOZARIL), norclozapine (ACP-104), risperidone (RISPERDAL), paliperidone (INVEGA), melperone, olanzapine (ZYPREXA), quetiapine (SEROQUEL), sertindole, sulpiride (MERESA, DOGMATYL, SULPITIL), talnetant, amisulpride, ziprasidone (GEODON), blonanserin (LONASEN), ACP-103 (Acadia Pharmaceuticals), and bifeprunox;

(x) calcium channel blockers such as nilvadipine (ESCOR, NIVADIL), diperdipine, amlodipine (NORVASC, ISTIN, AMLODIN), felodipine (PLENDIL), nicardipine (CARDENE), nifedipine (ADALAT, PROCARDIA), MEM 1003 and its parent compound nimodipine (NIMOTOP), nisoldipine (SULAR), nitrendipine, lacidipine (LACIPIL, MOTENS), lercanidipine (ZANIDIP), lifarizine, diltiazem (CARDIZEM), verapamil (CALAN, VERELAN), AR-R 18565 (AstraZeneca), and enecadin;

(xi) catechol O-methyltransferase (COMT) inhibitors, such as tolcapone (TASMAR), entacapone (COMTAN), and tropolone;

(xii) central nervous system stimulants, such as caffeine, phenmetrazine, phendimetrazine, pemoline, fencamfamine (GLUCOENERGAN, REACTIVAN), fenethylline (CAPTAGON), pipradol (MERETRAN), deanol (also known as dimethylaminoethanol), methylphenidate (DAYTRANA), methylphenidate hydrochloride (RITALIN), dexmethylphenidate (FOCALIN), amphetamine (alone or in combination with other CNS stimulants, e.g. ADDERALL (amphetamine aspartate, amphetamine sulfate, dextroamphetamine saccharate, and dextroamphetamine sulfate)), dextroamphetamine sulfate (DEXEDRINE, DEXTROSTAT), methamphetamine (DESOXYN), lisdexamfetamine (VYVANSE), and benzphetamine (DIDREX);

(xiii) corticosteroids, such as prednisone (STERAPRED, DELTASONE), prednisolone (PRELONE), predisolone acetate (OMNIPRED, PRED MILD, PRED FORTE), prednisolone sodium phosphate (ORAPRED ODT), methylprednisolone (MEDROL); methylprednisolone acetate (DEPO-MEDROL), and methylprednisolone sodium succinate (A-METHAPRED, SOLU-MEDROL);

(xiv) dopamine receptor agonists, such as apomorphine (APOKYN), bromocriptine (PARLODEL), cabergoline (DOSTINEX), dihydrexidine, dihydroergocryptine, fenoldopam (CORLOPAM), lisuride (DOPERGIN), pergolide (PERMAX), piribedil (TRIVASTAL, TRASTAL), pramipexole MIRAPEX), quinpirole, ropinirole (REQUIP), rotigotine (NEUPRO), SKF-82958 (GlaxoSmithKline), and sarizotan;

(xv) dopamine receptor antagonists, such as tetrabenazine (NITOMAN, XENAZINE), 7-hydroxyamoxapine, droperidol (INAPSINE, DRIDOL, DROPLETAN), domperidone (MOTILIUM), L-741742, L-745870, raclopride, SB-277011A, SCH-23390, ecopipam, SKF-83566, and metoclopramide (REGLAN);

(xvi) dopamine reuptake inhibitors such as nomifensine maleate (MERITAL), vanoxerine (also known as GBR-12909) and its decanoate ester DBL-583, and aminetine;

(xvii) gamma-amino-butyric acid (GABA) receptor agonists, such as baclofen (LIORESAL, KEMSTRO), siclofen, pentobarbital (NEMBUTAL), progabide (GABRENE), and clomethiazole;

(xviii) histamine 3 (H3) antagonists such as ciproxifan and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600;

(xix) immunomodulators such as glatiramer acetate (also known as copolymer-1; COPAXONE), MBP-8298 (synthetic myelin basic protein peptide), dimethyl fumarate, fingolimod (also known as FTY720), roquinimex (LINOMIDE), laquinimod (also known as ABR-215062 and SAIK-MS), ABT-874 (human anti-IL-12 antibody; Abbott), rituximab (RITUXAN), alemtuzumab (CAMPATH), daclizumab (ZENAPAX), and natalizumab (TYSABRI);

(xx) immunosuppressants such as methotrexate (TREXALL, RHEUMATREX), mitoxantrone (NOVANTRONE), mycophenolate mofetil (CELLCEPT), mycophenolate sodium (MYFORTIC), azathioprine (AZASAN, IMURAN), mercaptopurine (PURI-NETHOL), cyclophosphamide (NEOSAR, CYTOXAN), chlorambucil (LEUKERAN), cladribine (LEUSTATIN, MYLINAX), alpha-fetoprotein, etanercept (ENBREL), and 4-benzyloxy-5-((5-undecyl-2H-pyrrol-2-ylidene)methyl)-2,2'-bi-1H-pyrrole (also known as PNU-156804);

(xxi) interferons, including interferon beta-1a (AVONEX, REBIF) and interferon beta-1b (BETAFERON, BETAFERON);

(xxii) levodopa (or its methyl or ethyl ester), alone or in combination with a DOPA decarboxylase inhibitor (e.g. carbidopa (SINEMET, CARBILEV, PARCOPA), benserazide (MADOPAR), α-methyldopa, monofluoromethyldopa, difluoromethyldopa, brocresine, or m-hydroxybenzylhydrazine);

(xxiii) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), LY-233536 and LY-235959 (both Lilly), methadone, (DOLOPHINE), neramexane, perzinfotel, phencyclidine, tianeptine (STABLON), dizocilpine (also known as MK-801), EAB-318 (Wyeth), ibogaine, voacangine, tiletamine, riluzole (RILUTEK), aptiganel (CERESOTAT), gavestinel, and remacimide;

(xxiv) monoamine oxidase (MAO) inhibitors, such as selegiline (EMSAM), selegiline hydrochloride (I-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xxv) muscarinic receptor (particularly M1 subtype) agonists, such as bethanechol chloride (DUVOID, URECHOLINE), itameline, pilocarpine (SALAGEN), NGX267, arecoline, L-687306 (Merck), L-689660 (Merck), furtrethonium iodide (FURAMON, FURANOL), furtrethonium benzensulfonate, furtrethonium p-toluenesulfonate, McN-A-343, oxotremorine, sabcomeline, AC-90222 (Acadia Pharmaceuticals), and carbachol (CARBASTAT, MIOSTAT, CARBOPTIC);

(xxvi) neuroprotective drugs such as 2,3,4,9-tetrahydro-1H-carbazol-3-one oxime, desmoteplase, anatibant, astaxanthin, neuropeptide NAP (e.g. AL-108 and AL-208; both Allon Therapeutics), neurostrol, perampenel, ispronicline, bis(4-β-

D-glucopyranosyloxybenzyl)-2-β-D-glucopyranosyl-2-isobutyltartrate (also known as dactylorhin B or DHB), formobactin, xaliproden (XAPRILA), lactacystin, dimeboline hydrochloride (DIMEBON), disufenton (CEROVIVE), arundic acid (ONO-2506, PROGLIA, CEREACT), citicoline (also known as cytidine 5'-diphosphocholine), edaravone (RADICUT), AEOL-10113 and AEOL-10150 (both Aeolus Pharmaceuticals), AGY-94806 (also known as SA-450 and Msc-1), granulocyte-colony stimulating factor (also known as AX-200), BAY-38-7271 (also known as KN-387271; Bayer AG), ancrod (VIPRINEX, ARWIN), DP-b99 (D-Pharm Ltd), HF-0220 (17-β-hydroxyepiandrosterone; Newron Pharmaceuticals), HF-0420 (also known as oligotropin), pyridoxal 5'-phosphate (also known as MC-1), microplasmin, S-18986, piclozotan, NP031112, tacrolimus, L-seryl-L-methionyl-L-alanyl-L-lysyl-L-glutamyl-glycyl-L-valine, AC-184897 (Acadia Pharmaceuticals), ADNF-14 (National Institutes of Health), stilbazulenyl nitrone, SUN-N8075 (Daiichi Suntory Biomedical Research), and zonampanel;

(xxvii) nicotinic receptor agonists, such as epibatidine, ABT-089 (Abbott), ABT-594, AZD-0328 (AstraZeneca), EVP-6124, R3487 (also known as MEM3454; Roche/Memory Pharmaceuticals), R4996 (also known as MEM63908; Roche/Memory Pharmaceuticals), TC-4959 and TC-5619 (both Targacept), and RJR-2403;

(xxviii) norepinephrine (noradrenaline) reuptake inhibitors, such as atomoxetine (STRATTERA), doxepin (APONAL, ADAPIN, SINEQUAN), nortriptyline (AVENTYL, PAMELOR, NORTRILEN), amoxapine (ASENDIN, DEMOLOX, MOXIDIL), reboxetine (EDRONAX, VESTRA), viloxazine (VIVALAN), maprotiline (DEPRILEPT, LUDIOMIL, PSYMION), bupropion (WELLBUTRIN), and radaxafine;

(xxix) other PDE9 inhibitors, such as BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008);

(xxx) other phosphodiesterase (PDE) inhibitors, including (a) PDE1 inhibitors (e.g. vinpocetine (CAVINTON, CERACTIN, INTELECTOL) and those disclosed in U.S. Pat. No. 6,235,742, (b) PDE2 inhibitors (e.g. erythro-9-(2-hydroxy-3-nonyl)adenine (EHNA), BAY 60-7550, and those disclosed in U.S. Pat. No. 6,174,884), (c) PDE4 inhibitors (e.g. rolipram, Ro 20-1724, ibudilast (KETAS), piclamilast (also known as RP73401), CDP840, cilomilast (ARIFLO), roflumilast, tofimilast, oglemilast (also known as GRC 3886), tetomilast (also known as OPC-6535), lirimifast, theophylline (UNIPHYL, THEOLAIR), arofylline (also known as LAS-31025), doxofylline, RPR-122818, or mesembrine), and (d) PDE5 inhibitors (e.g. sildenafil (VIAGRA, REVATIO), tadalafil (CIALIS), vardenafil (LEVITRA, VIVANZA), udenafil, avanafil, dipyridamole (PERSANTINE), E-4010, E-4021, E-8010, zaprinast, PF-489791 (Pfizer), UK-357903 (Pfizer), DA-8159, and those disclosed in International Patent Applications WO2002/020521, WO2005/049616, WO2006/120552, WO2006/126081, WO2006/126082, WO2006/126083, and WO2007/122466);

(xxxi) quinolines, such as quinine (including its hydrochloride, dihydrochloride, sulfate, bisulfate and gluconate salts), chloroquine, sontoquine, hydroxychloroquine (PLAQUENIL), mefloquine (LARIAM), and amodiaquine (CAMOQUIN, FLAVOQUINE);

(xxxii) β-secretase inhibitors, such as WY-25105, (+)-phenserine tartrate (POSIPHEN), LSN-2434074 (also known as LY-2434074), PNU-33312, KMI-574, SCH-745966, Ac-rER ($N^2$-acetyl-D-arginyl-L-arginine), loxistatin (also known as E64d), and CA074Me;

(xxxiii) γ-secretase inhibitors, such as LY-411575 (Lilly), LY-685458 (Lilly), ELAN-G, ELAN-Z, 4-chloro-N-[2-ethyl-1-(S)-(hydroxymethyl)butyl]benzenesulfonamide;

(xxxiv) serotonin (5-hydroxytryptamine) 1A (5-$HT_{1A}$) receptor antagonists, such as spiperone, levo-pindolol, BMY 7378, NAD-299, S(−)-UH-301, NAN 190, WAY 100635, lecozotan (also known as SRA-333; Wyeth);

(xxxv) serotonin (5-hydroxytryptamine) 4 (5-$HT_4$) receptor agonists, such as PRX-03140 (Epix);

(xxxvi) serotonin (5-hydroxytryptamine) 6 (5-$HT_6$) receptor antagonists, such as mianserin (TORVOL, BOLVIDON, NORVAL), methiothepin (also known as metitepine), ritanserin, ALX-1161, ALX-1175, MS-245, LY-483518 (also known as SGS518; Lilly), MS-245, Ro 04-6790, RO 43-68544, Ro 63-0563, RO 65-7199, Ro 65-7674, SB-399885, SB-214111, SB-258510, SB-271046, SB-357134, SB-699929, SB-271046, SB-742457 (GlaxoSmithKline), Lu AE58054 (Lundbeck A/S), and PRX-07034 (Epix);

(xxxvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, and tesofensine;

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline, idebenone, PYM50028 (COGANE; Phytopharm), and AIT-082 (NEOTROFIN); and the like.

The invention also includes methods of inhibiting PDE9 in a mammal comprising administering to the mammal in need of such inhibition a PDE9 inhibiting amount of: (a) a compound of Formula (I), or a pharmaceutically acceptable salt thereof; or (b) a pharmaceutical composition comprising a compound of Formula (I), or a pharmaceutically acceptable salt thereof, in a pharmaceutically acceptable vehicle, carrier or diluent; either alone or in combination with a second agent as described above.

The invention also includes methods of treating conditions mediated by PDE9 inhibition in a mammal comprising administering to the mammal in need of such treatment a therapeutically effective amount of: (a) a compound of Formula (I), or a pharmaceutically acceptable salt thereof; or (b) a pharmaceutical composition comprising a compound of Formula (I), or a pharmaceutically acceptable salt thereof, in a pharmaceutically acceptable vehicle, carrier or diluent; either alone or in combination with a second agent described above.

Conditions that may be treated, controlled or prevented by the methods of the present invention include diseases and disorders associated with neurodegeneration such as: Alexander disease, Alper's disease, Alzheimer's disease, amyotrophic lateral sclerosis (ALS; also known as Lou Gehrig's disease or motor neuron disease), ataxia-telangiectasia, Batten disease (also known as Spielmeyer-Vogt-Sjogren-Batten disease), Binswanger's dementia (subcortical arteriosclerotic encephalopathy), bipolar disorders, bovine spongiform encephalopathy (BSE), Canavan disease, chemotherapy-induced dementia, Cockayne syndrome, corticobasal degeneration, Creutzfeldt-Jakob disease, depression, Down syndrome, frontotemporal lobar degeneration (including frontotemporal dementia, semantic dementia, and progressive nonfluent aphasia), Gerstmann-Straüssler-Scheinker disease, glaucoma, Huntington's disease (chorea), HIV-associated dementia, hyperkinesias, Kennedy's disease, Korsakoffs syndrome (amnesic-confabulatory syndrome), Krabbe's disease, Lewy body dementia, logopenic progressive aphasia, Machado-Joseph disease (spinocerebellar ataxia type 3), multiple sclerosis, multiple system atrophy (olivopontocerebellar atrophy), myasthenia gravis, Parkinson's disease, Pelizaeus-Merzbacher disease, Pick's disease, pre-senile dementia (mild cognitive impairment), primary lateral sclerosis, primary progressive aphasia, radiation-induced dementia, Refsum's disease (phytanic acid storage disease), Sandhoff disease, Schilder's disease, schizophrenia, semantic dementia, senile dementia, Shy-Drager syndrome, spinocerebellar ataxias, spinal muscular atrophies, Steele-Richardson-Olszewski disease (progressive supranuclear palsy), tabes dorsalis, tardive dyskinesia, vascular amyloidosis, and vascular dementia (multi-infarct dementia).

Preferably the neurodegenerative disease or disorder is Alzheimer's disease.

Other conditions and disorders associated with PDE9 that may be treated or controlled by the methods of the present invention include disorders of the urogenital system such as sexual dysfunction, attention deficit disorder (ADD), attention deficit hyperactivity disorder (ADHD), diabetes, cardiovascular disorders or diseases such as systemic hypertension, pulmonary hypertension, congestive heart failure, coronary artery disease, atherosclerosis, stroke, thrombosis, conditions of reduced blood vessel patency (e.g. post-percutaneous transluminal coronary angioplasty), peripheral vascular disease, renal disease, angina (including stable, unstable, and variant (Prinzmetal) angina), and any condition where improved blood flow leads to improved end organ function.

The present invention also relates to methods for promoting neurorestoration and functional recovery in patients suffering from traumatic or non-traumatic injury to the brain, spinal cord or peripheral nerves. Traumatic brain injuries include both closed head injuries (in which the skull is not broken) and open, or penetrating, head injuries (in which an object pierces the skull and breaches the dura mater), wherein sudden trauma (e.g., accidents, falls, assaults) causes damage to the brain tissue by tearing, stretching, bruising, or swelling. Causes of non-traumatic brain injuries include aneurysm, stroke, meningitis, oxygen deprivation due to anoxia, hypoxia, or ischemia, brain tumor, infection (e.g. encephalitis), poisoning, substance abuse, and the like. The present invention is useful for the treatment of cognitive impairment and cognitive dysfunction resulting from brain injuries as well as from neurodegenerative diseases and disorders.

The present invention also relates to methods for preventing the above-described conditions in a mammal, including human, comprising the steps of administering to the mammal an amount of: (a) a compound of Formula (I), or a pharmaceutically acceptable salt thereof; or (b) a pharmaceutical composition comprising a compound of Formula (I), or a pharmaceutically acceptable salt thereof, in a pharmaceutically acceptable vehicle, carrier or diluent; either alone or in combination with a second agent as described above, as part of an appropriate dosage regimen designed to prevent said condition.

The present invention also relates to methods for enhancing cognition and for improving cognitive deficits, including deficits in perception, concentration, learning, memory, communication, reasoning, and problem-solving.

The appropriate dosage regimen, the amount of each dose administered and the intervals between doses of the compound will depend upon, among other considerations, the compound of Formula (I) of this invention being used, the type of pharmaceutical composition being used, the characteristics of the subject being treated and the type and severity of the conditions to be treated. In general, an effective dose for compounds of Formula (I) or pharmaceutically acceptable salts thereof, is in the range of about 0.1 mg to about 3,500 mg per day. For a normal adult human having a body mass of about 70 kg, a dosage in the range of about 0.01 mg to about 50 mg per kg body mass is typically sufficient, and preferably about 0.2 to 2.5 mg per kg, in single or divided doses daily. Administration may be in single (e.g. once daily) or multiple doses or via constant infusion.

Some variability in the general dosage range may be required depending upon the age and mass of the subject being treated, the intended route of administration, the particular compound being administered, and the like. The determination of dosage ranges and optimal dosages for a particular mammalian subject is within the ability of a skilled person having benefit of the instant disclosure.

The compounds of Formula (I) may be administered by a variety of conventional routes of administration, including oral, buccal, sublingual, ocular, topical (e.g. transdermal), parenteral (e.g. intravenous, intramuscular, or subcutaneous), rectal, intracisternal, intravaginal, intraperitoneal, intravesical, local (e.g. powder, ointment, or drop), nasal and/or inhalation dosage forms or using a "flash" formulation, i.e., allowing the medication to dissolve in the mouth without the need to use water. As will be recognized by one of skill in the art, the appropriate dosage regimen, the amount of each dose administered and the intervals between doses of the compound will depend upon the compound of Formula (I), or the prodrug thereof, being used, the type of pharmaceutical compositions being used, the characteristics of the subject being treated, and/or the severity of the conditions being treated.

Methods of preparing various pharmaceutical compositions with amounts of active ingredients are known, or will be apparent in light of this disclosure, to those skilled in this art. See, for example, Remington's Pharmaceutical Sciences, Mack Publishing Co., Easton, Pa., 19th Ed. (1995).

Suitable pharmaceutical carriers, vehicles and diluents for such compositions include inert solid diluents or fillers, sterile aqueous solutions and various organic solvents. The pharmaceutical compositions formed by combining a compound of this invention and pharmaceutically acceptable carriers, vehicles or diluents are readily administered in a variety of dosage forms such as tablets, powders, lozenges, syrups, injectable solutions and the like.

Solid dosage forms for oral administration include capsules, tablets, powders, and granules. In such solid dosage forms, the active compound is admixed with at least one inert conventional pharmaceutical excipient (or carrier) such as sodium citrate, calcium carbonate, or dicalcium phosphate, or (a) fillers or extenders, such as for example, starches, lactose, sucrose, mannitol and silicic acid; (b) binders, such as for example, carboxymethylcellulose, alginates, gelatin, polyvinylpyrrolidone, sucrose and acacia; (c) humectants, such as for example, glycerol; (d) disintegrating agents, such as for example, agar-agar, calcium carbonate, potato or tapioca starch, alginic acid, certain complex silicates, and sodium carbonate; (e) solution retarders, such as for example, paraffin; (f) absorption accelerators, such as for example, quaternary ammonium compounds; (g) wetting agents, such as for example, cetyl alcohol and glycerol monostearate; (h) adsorbents, such as for example, kaolin and bentonite; and/or (i) lubricants, such as for example, talc, calcium stearate, magnesium stearate, solid polyethylene glycols, sodium lauryl sulfate or mixtures thereof. In the case of capsules and tablets, the dosage forms may further comprise buffering agents.

Solid dosage forms may be formulated as modified release and pulsatile release dosage forms containing excipients such as those detailed above for immediate release dosage forms together with additional excipients that act as release rate modifiers, these being coated on and/or included in the body of the device. Release rate modifiers include, but are not limited to, hydroxypropylmethyl cellulose, methyl cellulose, sodium carboxymethylcellulose, ethyl cellulose, cellulose acetate, polyethylene oxide, xanthan gum, ammoniomethacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients.

The pharmaceutical compositions of the invention may further comprise fast dispersing or dissolving dosage formulations (FDDFs). The terms dispersing or dissolving as used herein to describe FDDFs are dependent upon the solubility of the drug substance used i.e., where the drug substance is insoluble, a fast dispersing dosage form may be prepared, and where the drug substance is soluble, a fast dissolving dosage form may be prepared.

Solid compositions of a similar type may also be employed as fillers in soft or hard filled gelatin capsules using such excipients as lactose or milk sugar, as well as high molecular weight polyethylene glycols and the like.

Solid dosage forms such as tablets, dragees, capsules, and granules can be prepared with coatings and shells, such as enteric coatings and others well-known to one of ordinary skill in the art. They may also comprise opacifying agents, and can also be of such composition that they release the active compound(s) in a delayed, sustained or controlled manner. Examples of embedding compositions that can be employed are polymeric substances and waxes. The active compound(s) can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethanol, isopropanol, ethyl carbonate, benzyl benzoate, propylene glycol, 1,3-butylene glycol, oils (in particular, cottonseed oil, groundnut oil, corn germ oil, olive oil, castor oil, and sesame seed oil), glycerol, tetrahydrofurfuryl alcohol, polyethylene glycols and fatty acid esters of sorbitan, or mixtures of these substances, and the like.

In addition to the active compound(s), the pharmaceutical composition may further include suspending agents, such as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like. Sweeteners, flavoring, and perfuming agents may also be included.

The pharmaceutical compositions of the invention may further comprise adjuvants, such as preserving, wetting, emulsifying and dispersing agents. Prevention of microorganism contamination of the instant compositions can be accomplished with various antibacterial and antifungal agents, for example, parabens, chlorobutanol, phenol, sorbic acid and the like. It may also be desirable to include isotonic agents, for example, sugars, sodium chloride and the like. Prolonged absorption of injectable pharmaceutical compositions may be affected by the use of agents capable of delaying absorption, for example, aluminum monostearate and gelatin.

For parenteral administration, solutions in sesame or peanut oil, aqueous propylene glycol, or in sterile aqueous solutions may be employed. Such aqueous solutions should be suitably buffered if necessary and the liquid diluent first rendered isotonic with sufficient saline or glucose. These aqueous solutions are especially suitable for intravenous, intramuscular, subcutaneous and intraperitoneal administration. In this connection, the sterile aqueous media employed are all readily available by standard techniques known to those skilled in the art.

For intranasal administration or administration by inhalation, the compounds of Formula (I) are conveniently delivered in the form of a solution or suspension from a pump spray container that is squeezed or pumped by the patient or as an aerosol spray presentation from a pressurized container or a nebulizer, with the use of a suitable propellant, e.g., carbon dioxide dichlorodifluoromethane, trichlorofluoromethane, dichlorotetrafluoroethane, or other suitable gas. In the case of a pressurized aerosol, the dosage unit may be determined by providing a valve to deliver a metered amount. The pressurized container or nebulizer may contain a solution or suspension of a compound of this invention. Capsules and cartridges (made, for example, from gelatin) for use in an inhaler or insufflator may be formulated containing a powder mix of a compound or compounds of the invention and a suitable powder base such as lactose or starch.

Pharmaceutical compositions of the present invention may also be configured for treatments in veterinary use, where a compound of the present invention, or a veterinarily acceptable salt thereof, or veterinarily acceptable solvate or prodrug thereof, is administered as a suitably acceptable formulation in accordance with normal veterinary practice and the veterinary practitioner will determine the dosing regimen and route of administration which will be most appropriate for a particular animal.

In general, the compounds of Formula (I), and pharmaceutically acceptable salts thereof, may be prepared according to the exemplary routes disclosed in the Schemes and Examples below, as well as by other conventional preparative procedures known, or apparent in light of the instant disclosure, to one of ordinary skill in the art. These processes form further aspects of the invention.

Some of the starting compounds for the reactions described in the Schemes and Examples are prepared as illustrated herein. All other starting compounds may be obtained from general commercial sources, such as Sigma-Aldrich Corp., St. Louis, Mo.

Unless indicated otherwise, the following experimental abbreviations have the meanings indicated in Table 1:

μL—microliter
br d—broad doublet
br m—broad multiplet
BOC—t-butoxycarbonyl
br s—broad singlet
CDCl$_3$—deuterated chloroform CD₃OD—deuterated methanol
dd—doublet of doublets
DMF—dimethylformamide
DMSO—dimethyl sulfoxide
dt—doublet of triplets
EtOAc—ethyl acetate
EtOH—ethanol
h (e.g., 1 h, 2 h)—hour(s)
H (e.g., 1H, 2H)—hydrogen(s)
Hz—hertz
IPA—isopropyl alcohol
J—spin-spin coupling constant
LC—liquid chromatography
m—multiplet
MHz—megahertz
min(s)—minute(s)
MeOH—methanol
mg—milligram
mL—milliliter
mmol—millimoles
MS—mass spectroscopy
mw—molecular weight
NMR—nuclear magnetic resonance
PMSF—phenylmethanesulfonyl fluoride
ppm—parts per million
psi—pounds per square inch
s—singlet
SPA—scintillation proximity assay
t—triplet
temp—temperature
THF—tetrahydrofuran
Tris—tris(hydroxymethyl)aminomethane The methods disclosed in the instant Schemes and Examples are intended for purposes of exemplifying the instant invention only and are not to be construed as limitations thereon.

Experimental Procedures

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally Sure-Seal™ products from the Aldrich Chemical Co., Milwaukee, Wis.). Mass spectrometry data is reported from either liquid chromatography-mass spectrometry (LCMS) or atmospheric pressure chemical ionization (APCI) instrumentation. Chemical shifts for nuclear magnetic resonance (NMR) data are expressed in parts per million (ppm, δ) referenced to residual peaks from the deuterated solvents employed, or to tetramethylsilane standard.

EXAMPLE 1

6-{(1R)-1-[3-(4-Methylpyridin-2-yl)azetidin-1-yl]ethyl}-1-(tetrahydro-2H-pyran-4-yl)-1,5-dihydro-4H-pyrazolo[3,4-d]pyrimidin-4-one

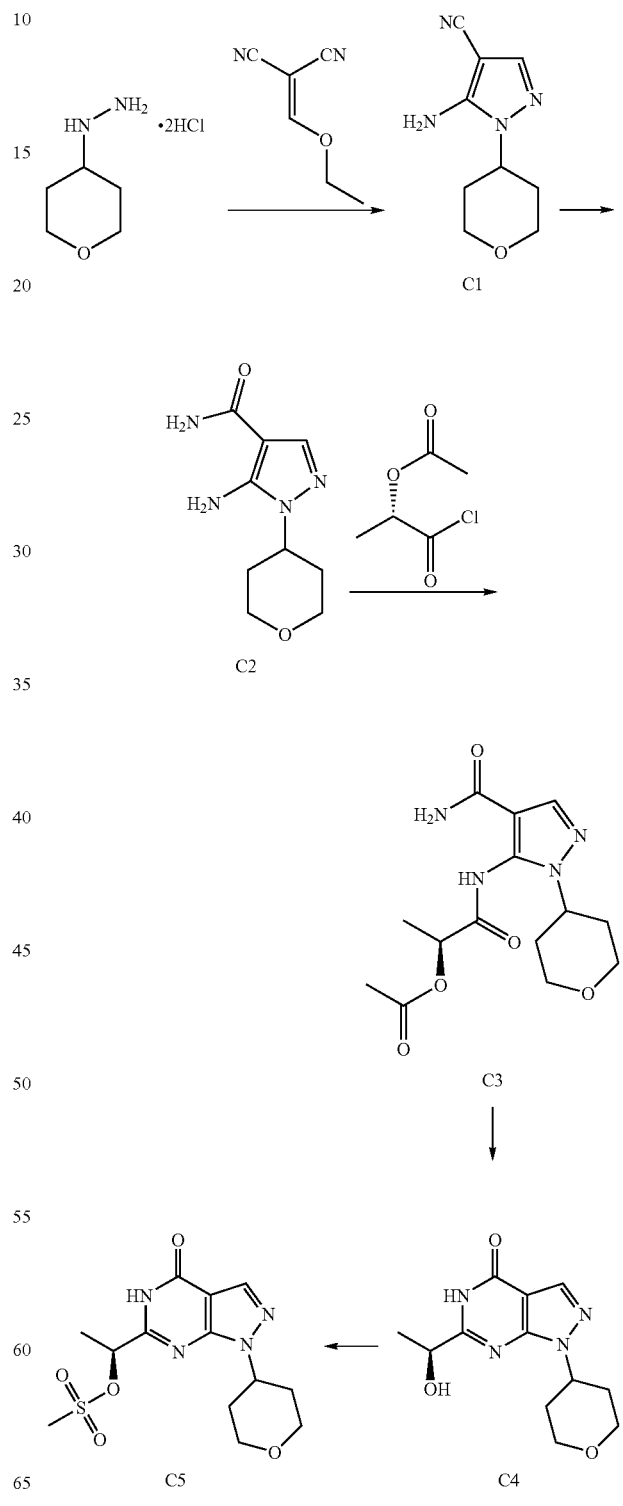

21
-continued

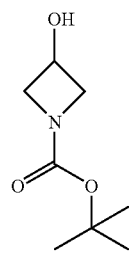

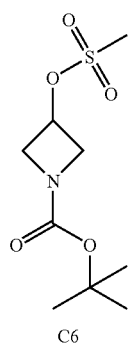

C6

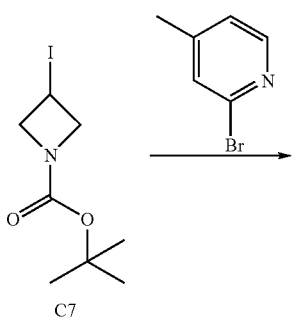

C7

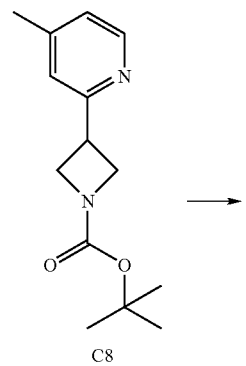

C8

22
-continued

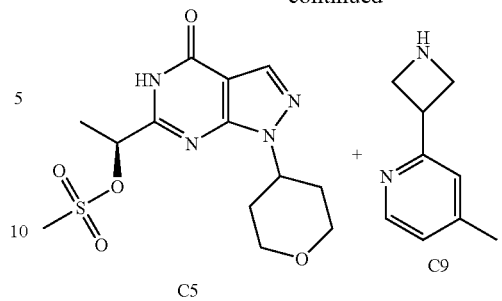

C5

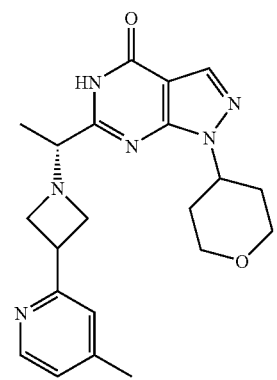

1

Step 1 Preparation of (1S)-1-[4-oxo-1-(tetrahydro-2H-pyran-4-yl)-4,5-dihydro-1H-pyrazolo[3,4-d]pyrimidin-6-yl]ethyl methanesulfonate (C5)

A. Preparation of 5-amino-1-(tetrahydro-2H-pyran-4-yl)-1H-pyrazole-4-carbonitrile (C1). To a solution of tetrahydro-2H-pyran-4-ylhydrazine dihydrochloride (See R. R. Ranatunge et al., *J. Med. Chem.* 2004, 47, 2180-2193) (43 g, 228 mmol) in EtOH (300 mL) was slowly added sodium ethoxide (32.6 g, 479 mmol), and the resulting mixture was stirred at room temp for 1 h. The reaction mixture was then transferred into a solution of (ethoxymethylene)malononitrile (27.8 g, 228 mmol) in EtOH (300 mL). After being stirred at room temp for 30 mins, the reaction was heated at reflux for 2 h. It was then cooled to room temp and concentrated in vacuo to afford C1 as an orange solid, which was used in the next step without purification.

B. Preparation of 5-amino-1-(tetrahydro-2H-pyran-4-yl)-1H-pyrazole-4-carboxamide (C2). A solution of C1 (≦228 mmol) in EtOH (300 mL) was treated with 35% aqueous hydrogen peroxide (100 mL) followed by concentrated aqueous ammonia solution (300 mL). The reaction mixture was stirred for 48 h at room temp, then quenched with saturated aqueous sodium thiosulfate solution (800 mL). Removal of most of the EtOH in vacuo provided a solid that was isolated by filtration and washed with water (2×200 mL) and diethyl ether (2×150 mL) to provide C2 as a solid. Yield: 31 g, 147 mmol, 64% for 2 steps. MS (APCI) m/z 211.2 (M+1). $^1$H NMR (300 MHz, DMSO-$d_6$) δ 1.70 (m, 2H), 1.93 (m, 2H), 3.40 (m, 2H), 3.95 (dd, J=11.1, 3.2 Hz, 2H), 4.26 (m, 1H), 6.24 (m, 2H), 6.67 (br s, 1H), 7.20 (br s, 1H), 7.66 (s, 1H).

C. Preparation of (1S)-2-{[4-carbamoyl-1-(tetrahydro-2H-pyran-4-yl)-1H-pyrazol-5-yl]amino}-1-methyl-2-oxoethyl acetate (C3). (1S)-2-Chloro-1-methyl-2-oxoethyl acetate (30 g, 199 mmol) was added to a suspension of C2 (38.1 g, 181 mmol) in dry dioxane (1000 mL). The mixture was heated at reflux for 2 h, then concentrated in vacuo to provide C3, which was used in the next step without purification.

D. Preparation of 6-[(1S)-1-hydroxyethyl]-1-(tetrahydro-2H-pyran-4-yl)-1,5-dihydro-4H-pyrazolo[3,4-d]pyrimidin-4-one (C4); A suspension of C3 (≦181 mmol) in water (700 mL) was treated with anhydrous potassium carbonate (100 g). The mixture was heated at 45° C. for about 18 h, then neutralized with acetic acid and extracted with chloroform (4×1 L). The combined organic layers were washed with saturated aqueous sodium chloride solution and dried over sodium sulfate. Filtration and removal of solvents in vacuo provided C4 as an off-white solid. Yield: 43.1 g, 163 mmol, 90% over 2 steps. LCMS m/z 265.2 (M+1). $^1$H NMR (400 MHz, CDCl$_3$) δ 1.67 (d, J=6.6 Hz, 3H), 1.92 (br d, J=13 Hz, 2H), 2.39 (m, 2H), 3.62 (br dd, apparent br t, J=12, 12 Hz, 2H), 4.15 (br dd, J=11.7, 4 Hz, 2H), 4.84 (tt, J=11.6, 4.3 Hz, 1H), 4.90 (q, J=6.7 Hz, 1H), 8.08 (s, 1H), 10.65 (br s, 1H).

E. Preparation of compound C5. A solution of C4 (20.0 g, 75.7 mmol) in dichloromethane (400 mL) was treated with triethylamine (15.8 mL, 113 mmol), cooled to 0° C. and stirred for 30 mins. Methanesulfonyl chloride (99%, 5.92 mL, 75.7 mmol) was added drop-wise to the cold reaction, which was allowed to warm to room temp over the next 18 h. Solvents were removed in vacuo, and the residue was purified by silica gel chromatography (Gradient: 0% to 5% MeOH in dichloromethane). Rechromatography of mixed fractions provided additional product, to afford C5 as a solid. Total yield: 10.6 g, 31.0 mmol, 41%. LCMS m/z 341.1 (M−1). $^1$H NMR (400 MHz, CDCl$_3$) δ 1.86 (d, J=6.6 Hz, 3H), 1.93 (br d, J=12 Hz, 2H), 2.39 (m, 2H), 3.23 (s, 3H), 3.61 (ddd, apparent td, J=12, 12, 2.1 Hz, 2H), 4.16 (br dd, J=11.4, 3.5 Hz, 2H), 4.86 (tt, J=11.7, 4.2 Hz, 1H), 5.70 (q, J=6.7 Hz, 1H), 8.08 (s, 1H).

Step 2 Preparation of 2-azetidin-3-yl-4-methylpyridine (C9)

A. Preparation of tert-butyl 3-[(methylsulfonyl)oxy]azetidine-1-carboxylate (C6). A solution of tert-butyl 3-hydroxyazetidine-1-carboxylate (97%, 5.0 g, 28 mmol) in dichloromethane (50 mL) was treated with triethylamine (7.8 mL, 56 mmol) and cooled to 0° C. A solution of methanesulfonyl chloride (2.28 mL, 29.3 mmol) in dichloromethane was added drop-wise to the cold reaction, which was maintained at 0° C. for 2 h, then allowed to warm to room temp over the next 18 h. Solvents were removed in vacuo and the residue was taken up in ether and filtered: The filtrate was concentrated in vacuo, and the residue purified via silica gel chromatography (Eluant: 5:1 heptane:EtOAc, then 2:1 heptane:EtOAc) to provide C6 as a solid. Yield: 6.5 g, 26.0 mmol, 93%. LCMS m/z 503.1 (2M+1). $^1$H NMR (400 MHz, CDCl$_3$) δ 1.44 (s, 9H), 3.06 (s, 3H), 4.09 (ddd, J=10.4, 4.2, 1.2, 2H), 4.27 (ddd, J=10.4, 6.6, 1.2 Hz, 2H), 5.19 (tt, J=6.6, 4.2 Hz, 1H). $^{13}$C NMR (100 MHz, CDCl$_3$) δ28.23, 38.33, 56.45 (br), 67.25, 80.29, 155.80.

B. Preparation of tert-butyl 3-iodoazetidine-1-carboxylate (C7). Potassium iodide (12.9 g, 77.7 mmol) and C6 (6.5 g, 26.0 mmol) were combined in DMF (40 mL). The reaction mixture was stirred at 110° C. for 16 h, then concentrated in vacuo, diluted with water, and extracted with EtOAc. The combined organic layers were washed with water, then washed with saturated aqueous sodium chloride solution and dried over magnesium sulfate. Filtration and removal of solvent in vacuo gave a residue, which was purified by silica gel chromatography (Eluant: 4:1 heptane:EtOAc) to afford C7 as a solid. Yield: 6.2 g, 21.9 mmol, 84%. LCMS m/z 284.0 (M+1). $^1$H NMR (400 MHz, CDCl$_3$) δ 1.43 (s, 9H), 4.28 (m, 2H), 4.46 (m, 1H), 4.64 (m, 2H). $^{13}$C NMR (100 MHz, CDCl$_3$) δ 2.57, 28.27, 61.49, 80.09, 155.52.

C. Preparation of tert-butyl 3-(4-methylpyridin-2-yl)azetidine-1-carboxylate (C8). 1,2-Dibromoethane (98%, 0.031 mL, 0.35 mmol) was added to a suspension of zinc dust (98%, 354 mg, 5.3 mmol) in THF (15 mL), and the reaction mixture was heated to reflux for 1 h. After cooling to room temp, the reaction mixture was treated with trimethylsilyl chloride (99%, 0.045 mL, 0.35 mmol) and stirred for 1 h. At this point, a solution of C7 (1.0 g, 3.53 mmol) in THF (5 mL) was added drop-wise. The reaction was stirred for 1 h at 60° C. and cooled to room temp. 2-Bromo-4-methylpyridine (97%, 0.486 mL, 4.2 mmol) and tetrakis(triphenylphosphine)palladium(0) (99%, 82.9 mg, 0.071 mmol) were added, and the mixture was heated at reflux for 1 h, then stirred at room temp for about 18 h. The reaction was filtered through Celite (diatomaceous earth), and the filtrate was concentrated, then treated with EtOAc and saturated aqueous sodium carbonate solution. The resulting precipitate was removed by filtration and the filter cake was washed with EtOAc. The combined filtrates were washed with saturated aqueous sodium chloride solution, dried over magnesium sulfate, filtered and concentrated in vacuo. Purification by silica gel chromatography (Gradient: 1:4 to 1:1 EtOAc: heptane) provided C8 as a solid. Yield: 245 mg, 0.987 mmol, 28%. LCMS m/z 249.2 (M+1). $^1$H NMR (400 MHz, CDCl$_3$) δ 1.44 (s, 9H), 2.33 (s, 3H), 3.82 (tt, J=8.9, 6.0 Hz, 1H), 4.13 (m, 2H), 4.28 (dd, apparent t, J=8.7, 8.7 Hz, 2H), 6.98 (d, J=5.0 Hz, 1H), 7.05 (s, 1H), 8.43 (d, J=5.0 Hz, 1H). $^{13}$C NMR (100 MHz, CDCl$_3$) δ 20.96, 28.36, 34.90, 54.6 (v br), 79.30, 122.46, 122.88, 147.67, 149.30, 156.38, 160.64.

D. Preparation of compound C9. Compound C8 (124 mg, 0.50 mmol)) was mixed with dichloromethane (2 mL) and treated with trifluoroacetic acid (1 mL). The reaction mixture was stirred at room temp for about 18 h, then concentrated in vacuo to afford compound C9, which was used in the next step without purification, assuming quantitative conversion. LCMS m/z 149.1 (M+1).

Step 3. Synthesis of title compound 1. Compound C5 (114 mg, 0.333 mmol) and compound C9 (74.1 mg, 0.50 mmol) were combined in acetonitrile (2 mL) and toluene (2 mL), and treated with triethylamine (0.116 mL, 0.83 mmol). The reaction mixture was heated to 90° C. for 5 h, then cooled and concentrated in vacuo. The residue was purified via silica gel chromatography (Eluant: 100:1 chloroform: MeOH) to provide compound 1 as a solid. Yield: 92 mg, 0.23 mmol, 69%. LCMS m/z 395.1 (M+1). $^1$H NMR (400 MHz, CDCl$_3$) δ 1.33 (d, J=6.8 Hz, 3H), 1.91 (m, 2H), 2.34 (s, 3H), 2.37 (m, 2H), 3.44 (dd, apparent t, J=7, 7 Hz, 1H), 3.60 (m, 4H), 3.77 (m, 3H), 4.14 (br d, J=11.6 Hz, 2H), 4.83 (tt, J=11.6, 4.2 Hz, 1H), 6.99 (d, J=5.0 Hz, 1H), 7.03 (s, 1H), 8.06 (s, 1H), 8.44 (d, J=5.0 Hz, 1H).

EXAMPLE 2

6-[Cyclopropyl(3-phenoxyazetidin-1-yl)methyl]-1-(tetrahydro-2H-pyran-4-yl)-1,5-dihydro-4H-pyrazolo[3,4-d]pyrimidin-4-one

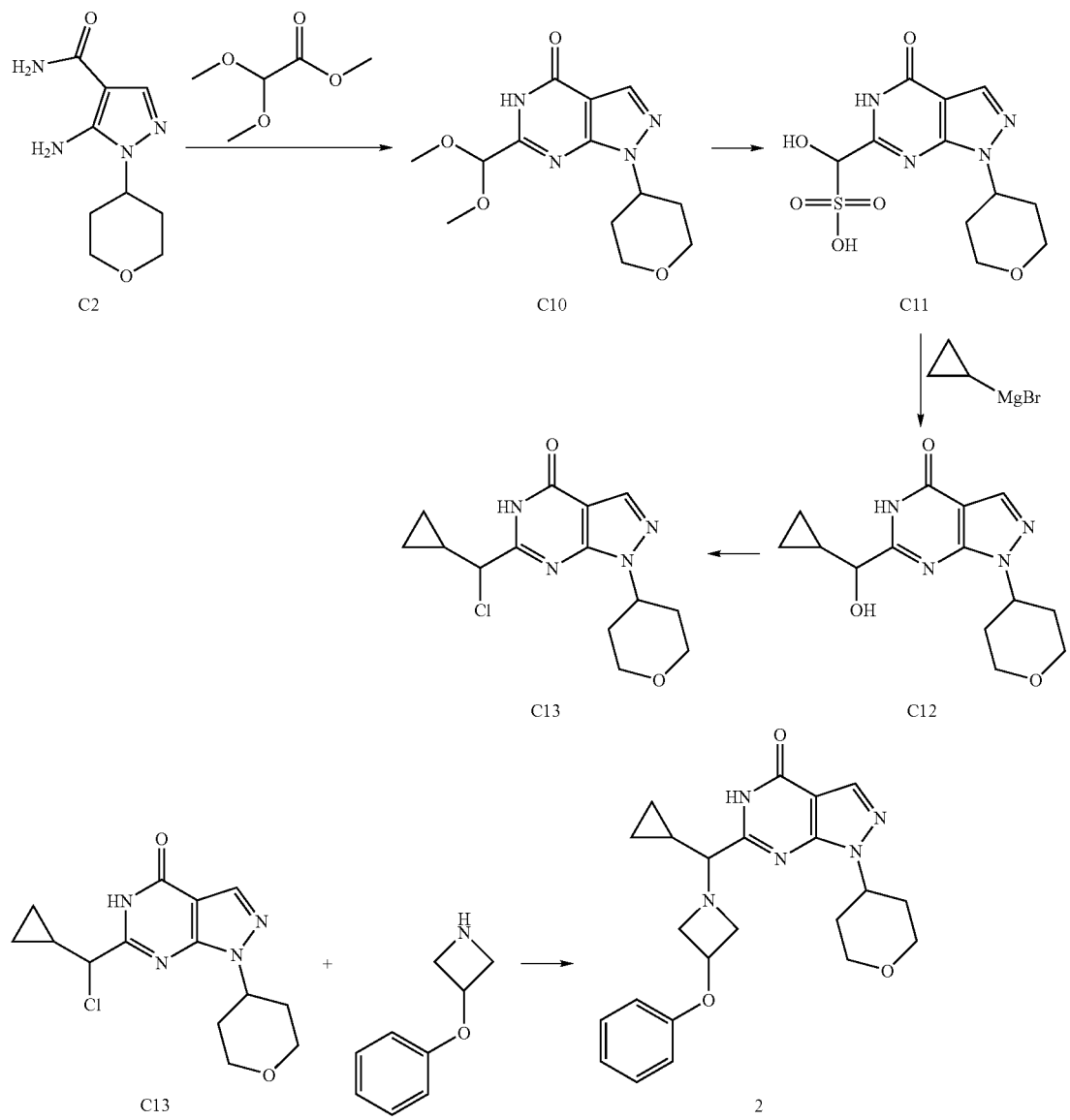

Step 1. Preparation of 6-[chloro(cyclopropyl)methyl]-1-(tetrahydro-2H-pyran-4-yl)-1,5-dihydro-4H-pyrazolo[3,4-d]pyrimidin-4-one (C13)

A. Preparation of 6-(dimethoxymethyl)-1-(tetrahydro-2'-1-pyran-4-yl)-1,5-dihydro-4H-pyrazolo[3,4-d]pyrimidin-4-one (C10). Methyl dimethoxyacetate (19.9 g, 148 mmol) and compound C2 (15.6 g, 74.2 mmol) were combined with molecular sieves (16 g), and the mixture was treated with a solution of potassium t-butoxide in THF (1.0M, 150 mL, 150 mmol). The reaction mixture was heated to reflux for about 18 h; it was then filtered, and the collected solid was rinsed with additional THF. The combined filtrates were neutralized with acetic acid and concentrated in vacuo. The residue was purified by silica gel chromatography (Eluant: 5% MeOH in chloroform) to afford C10 as a white solid. Yield: 9.8 g, 33 mmol, 44%. MS (APCI) m/z 295.2 (M+1). $^1$H NMR (300 MHz, CDCl$_3$) δ 1.91 (br d, J=10.5 Hz, 2H), 2.38 (m, 2H), 3.48 (s, 6H), 3.60 (dd, J=11, 12, 2H), 4.14 (br d, J=11 Hz, 2H), 4.90 (m, 1H), 5.22 (s, 1H), 8.10 (s, 1H), 9.52 (br s, 1H).

B. Preparation of hydroxy[4-oxo-1-(tetrahydro-2H-pyran-4-yl)-4,5-dihydro-1H-pyrazolo[3,4-d]pyrimidin-6-yl]methanesulfonic acid (C11). Compound C10 (1.0 g, 3.4 mmol) was combined with aqueous hydrochloric acid (1N, 10 mL) and THF (10 mL), and treated with para-toluenesulfonic acid monohydrate (646 mg, 3.40 mmol). The reaction mixture was heated to 67° C. for 16 h, during which time it became a light yellow solution. This was cooled to room temperature and adjusted to pH 7 with 1N aqueous sodium hydroxide. Sodium bisulfite (707 mg, 6.79 mmol) was added, and the reaction was allowed to stir for 1 h at room temp. Removal of solvents in vacuo was followed by three azeotropes with EtOH, to provide crude C11 as an off-white solid, which still contained excess sodium bisulfite and an equivalent of para-toluenesulfonic acid, sodium salt. This crude material was used in the next reaction. Recovery: 2.9 g, assumed quantitative. $^1$H NMR (400 MHz, CDCl$_3$), product peaks only: δ 1.84 (m, 2H), 2.11 (m, 2H), 3.54 (br dd, apparent t, J=12, 12 Hz, 2H), 3.98 (br dd, J=11.3, 4 Hz, 2H), 4.38 (br s, 1H), 4.88 (m, 1H), 4.93 (br s, 1H), 6.78 (br s, 1H), 8.08 (s, 1H).

C. Preparation of 6-[cyclopropyl(hydroxy)methyl]-1-(tetrahydro-2H-pyran-4-yl)-1,5-dihydro-4H-pyrazolo[3,4-d]pyrimidin-4-one (C12). Crude C11 (1.45 g, ≦1.7 mmol) from the previous step was slurried in THF (10 mL) and treated portion-wise with a solution of cyclopropylmagnesium bromide in THF (0.50M, 33.9 mL, 17 mmol). A slight exotherm was observed, and the reaction became yellow; it was heated to reflux for 16 h, then cooled to room temperature and quenched with an aqueous solution of ammonium chloride (3M, 20 mL) {Caution: exothermic and gas evolution}. The mixture was allowed to stir for 1 h at room temp, then extracted with dichloromethane. The combined organic layers were dried over magnesium sulfate, filtered and concentrated in vacuo. The resulting residue was purified via silica gel chromatography (Gradient: dichloromethane to 2.5% MeOH in dichloromethane) to provide C12 as a light yellow solid/gum, contaminated with extraneous cyclopropyl material, as assessed by $^1$H NMR. This material was taken on to the next step. Yield: 252 mg, <0.87 mmol, <51%. LCMS m/z 289.3 (M−1). $^1$H NMR (400 MHz, CDCl$_3$), product peaks only: δ 0.56 (m, 4H), 1.24 (m, 1H), 1.90 (m, 2H), 2.36 (dddd, J=12, 12, 12, 4.6 Hz, 2H), 3.58 (dd, J=12, 12 Hz, 2H), 4.12 (br dd, J=11.7, 4 Hz, 2H), 4.17 (d, J=7.0 Hz, 1H), 4.81 (tt, J=11.6, 4.2 Hz, 1H), 8.04 (s, 1H).

D. Preparation of compound C13. A solution of C12 (252 mg, <0.87 mmol) in dichloromethane (5 mL) was treated with triethylamine (0.18 mL, 1.3 mmol) and methanesulfonyl chloride (0.08 mL, 1.0 mmol) and allowed to stir at room temperature for 16 h. The reaction was then poured into water and the mixture was extracted with dichloromethane. The combined organic layers were washed twice with water, once with 1N aqueous hydrochloric acid and once with saturated aqueous sodium bicarbonate solution, then dried over magnesium sulfate. Filtration and removal of solvent under reduced pressure provided a residue that was purified by silica gel chromatography (Gradient: dichloromethane to 1.5% MeOH in dichloromethane), to provide C13 as a light yellow gum. Yield: 100 mg, 0.32 mmol, 19% over three steps. LCMS m/z 309.3 (M+1). $^1$H NMR (400 MHz, CDCl$_3$) δ 0.68 (m, 2H), 0.79 (m, 1H), 0.93 (m, 1H), 1.74 (m, 1H), 1.95 (m, 2H), 2.40 (m, 2H), 3.62 (br dd, J=12, 12 Hz, 2H), 4.16 (br d, J=12 Hz, 2H), 4.21 (d, J=9.5 Hz, 1H), 4.86 (tt, J=11.7, 4.2 Hz, 1H), 8.12 (s, 1H), 11.00 (br s, 1H).

Step 2. Synthesis of title compound 2. Compound C13 (100 mg, 0.32 mmol), 3-phenoxyazetidine (75.6 mg, 0.407 mmol) and triethylamine (0.102 mL, 0.732 mmol) were combined in acetonitrile (3 mL) and heated to reflux for 16 h. The reaction mixture was cooled to room temperature and poured into water. The resulting mixture was extracted twice with dichloromethane, and the organic layers were washed with water, then with saturated aqueous sodium bicarbonate solution. The organic layers were dried over magnesium sulfate, filtered and concentrated in vacuo; purification via silica gel chromatography (Eluant 2.5% MeOH in dichloromethane) afforded compound 2. Yield: 27 mg, 0.064 mmol, 20%. LCMS m/z 422.3 (M+1). $^1$H NMR (400 MHz, CDCl$_3$) δ 0.46 (m, 2H), 0.58 (m, 1H), 0.77 (m, 1H), 0.86 (m, 1H), 1.93 (m, 2H), 2.39 (m, 2H), 2.63 (d, J=8.9 Hz, 1H), 3.19 (dd, J=7.6, 6.1 Hz, 1H), 3.52 (dd, J=7.9, 6.0 Hz, 1H), 3.61 (m, 2H), 3.83 (br dd, J=7, 7 Hz, 1H), 4.01 (br dd, J=7, 7 Hz, 1H), 4.15 (br dd, J=11.4, 4 Hz, 2H), 4.82 (tt, J=11.8, 4.2 Hz, 1H), 4.85 (m, 1H), 6.78 (br d, J=8.6 Hz, 2H), 6.98 (br t, J=7.4 Hz, 1H), 7.29 (dd, J=8.8, 7.4 Hz, 2H), 8.07 (s, 1H), 9.74 (br s, 1H).

EXAMPLE 3

1-Cyclobutyl-6-{(1R)-1-[3-(pyrimidin-2-yloxy)azetidin-1-yl]ethyl}-1,5-dihydro-4H-pyrazolo[3,4-d]pyrimidin-4-one

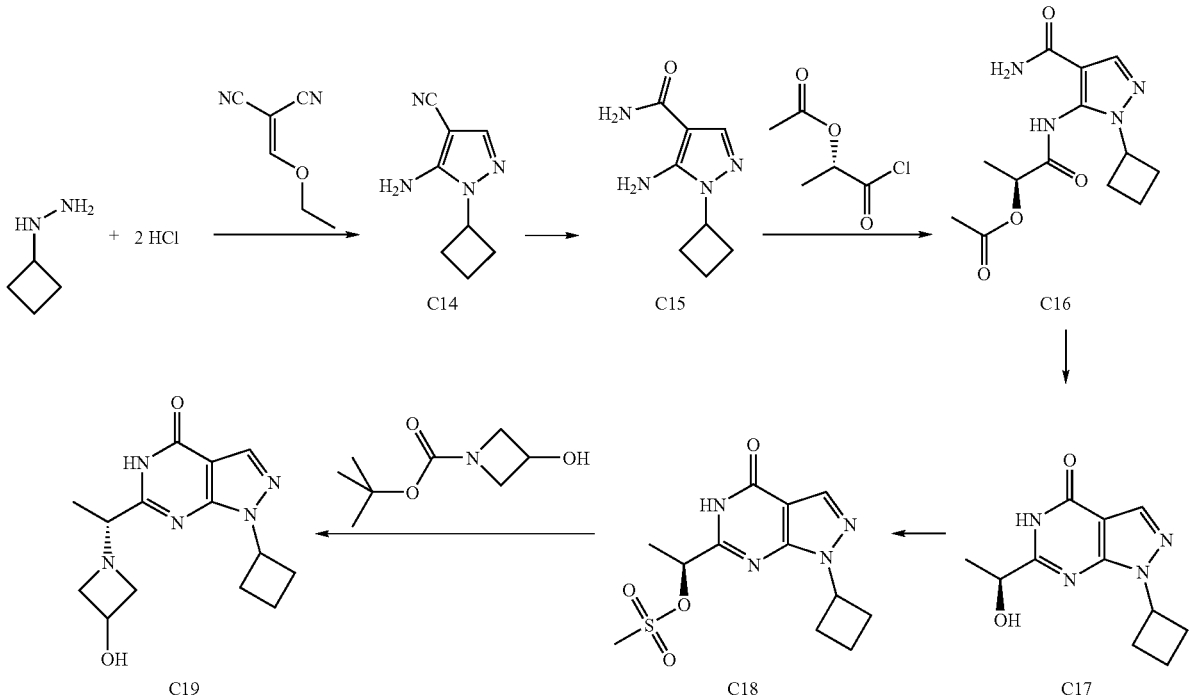

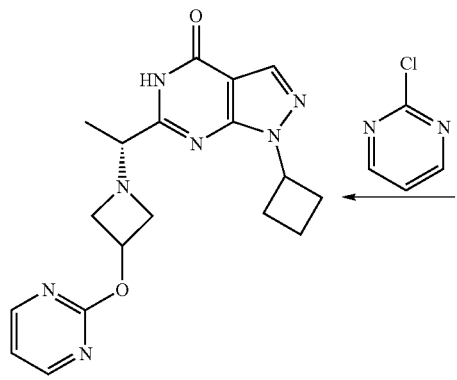

3

Step 1. Preparation of 5-amino-1-cyclobutyl-1H-pyrazole-4-carbonitrile (C14). A suspension of cyclobutylhydrazine dihydrochloride (11.63 g, 73.12 mmol) in EtOH (110 mL) was cooled in an ice bath and treated portion-wise with solid sodium ethoxide (9.95 g, 146 mmol) over 45 mins, while keeping the internal temp of the reaction mixture at approximately 0° C. The mixture was stirred in the ice bath for an additional hour, and then a solution of (ethoxymethylene)malononitrile (8.93 g, 73.1 mmol) in EtOH (70 mL) was added drop-wise over about 1.5 h, at a rate which maintained the internal temperature of the reaction mixture between 0° C. and 5° C. The reaction was then allowed to warm to room temp over about 18 h, after which it was heated at reflux for 1.5 h. After cooling to room temp, solvents were removed in vacuo, and the residue was partitioned between EtOAc and water. The aqueous layer was extracted twice with additional EtOAc, and the combined organic layers were washed with saturated aqueous sodium chloride solution, dried over sodium sulfate, and filtered. The filtrate was concentrated under reduced pressure to provide crude C14, which was used in the next step without purification. Yield: 14.1 g, >100% mass recovery. $^1$H NMR (300 MHz, CDCl$_3$) δ 1.9 (m, 2H), 2.4 (m, 2H), 2.65 (m, 2H), 4.25 (br s, 2H), 4.45 (m, 1H), 7.5 (s, 1H).

Step 2. Preparation of 5-amino-1-cyclobutyl-1H-pyrazole-4-carboxamide (C15). Crude C14 (14.1 g, ≦73.12 mmol) was cooled in an ice bath and treated with pre-cooled (ice bath) concentrated sulfuric acid (55 mL). The cooling bath was removed, and the reaction mixture agitated until a solution was obtained. After stirring at room temp for about 18 h, the reaction mixture was poured onto ice, which was itself cooled in an ice bath, and subsequently adjusted to a pH of about 11-12 by the addition of concentrated aqueous ammonium hydroxide. The resulting precipitate was collected by filtration and washed three times with water, then three times with diethyl ether, to provide C15 as a yellow solid. Yield: 6.0 g, 33 mmol, 45% over two steps. MS (APCI) m/z 181.2 (M+1). $^1$H NMR (300 MHz, DMSO-d$_6$) δ 1.73 (m, 2H), 2.27 (m, 2H), 2.44 (m, 2H), 4.68 (m, 1H), 6.15 (m, 2H), 6.6 (br s, 1H), 7.2 (br s, 1H), 7.68 (s, 1H).

Step 3. Preparation of (1S)-2-[(4-carbamoyl-1-cyclobutyl-1H-pyrazol-5-yl)amino]-1-methyl-2-oxoethyl acetate (C16). (1S)-2-Chloro-1-methyl-2-oxoethyl acetate (3.86 mL, 30.5 mmol) was slowly added to an ice-cooled suspension of C15 (5.00 g, 27.7 mmol) in dry dioxane (120 mL). The mixture was heated at 111° C. for 8 h, then cooled and stirred at room temp for about 18 h. The reaction was concentrated in vacuo to provide C16, which was used in the next step without purification.

Step 4. Preparation of 1-cyclobutyl-6-[(1S)-1-hydroxyethyl]-1,5-dihydro-4H-pyrazolo[3,4-d]pyrimidin-4-one (C17). Compound C17 was prepared according to the general procedure for the synthesis of C4 in Example 1, except that C16 was used in place of C3. Additionally, in this case the crude product was purified via silica gel chromatography (Eluant: 50:1 chloroform: MeOH), to afford C17 as a solid. Yield 5.70 g, 24.3 mmol, 87%. LCMS m/z 235.3 (M+1). $^1$H NMR (400 MHz, CDCl$_3$) δ 1.64 (d, J=6.6 Hz, 3H), 1.91 (m, 2H), 2.44 (m, 2H), 2.75 (m, 2H), 4.26 (br s, 1H), 4.89 (q, J=6.6 Hz, 1H), 5.25 (m, 1H), 8.06 (s, 1H), 11.07 (br s, 1H). $^{13}$C NMR (100 MHz, CDCl$_3$) δ 14.93, 22.42, 29.84, 50.92, 67.67, 104.42, 134.66, 151.71, 159.25, 161.48.

Step 5. Preparation of (1S)-1-(1-cyclobutyl-4-oxo-4,5-dihydro-1H-pyrazolo[3,4-d]pyrimidin-6-yl)ethyl methanesulfonate (C18). Compound C18 was prepared according to the general procedure for the synthesis of C5 in Example 1, except that C17 was used in place of C4, and the chromatographic purification was carried out with 0.5% to 1% MeOH in chloroform, rather than 0% to 5% MeOH in dichloromethane, to provide C18 as a solid. Yield: 6.0 g, 19.2 mmol, 79%. LCMS m/z 311.4 (M−1). $^1$H NMR (400 MHz, CDCl$_3$) δ 1.85 (d, J=6.6 Hz, 3H), 1.93 (m, 2H), 2.46 (m, 2H), 2.78 (m, 2H), 3.23 (s, 3H), 5.29 (m, 1H), 5.69 (q, J=6.6 Hz, 1H), 8.08 (s, 1H), 11.65 (br s, 1H). $^{13}$C NMR (100 MHz, CDCl$_3$) δ 14.93, 20.39, 29.84, 38.75, 51.07, 74.91, 104.98, 134.71, 151.07, 155.61, 159.27.

Step 6. Preparation of 1-cyclobutyl-6-[(1R)-1-(3-hydroxyazetidin-1-yl)ethyl]-1,5-dihydro-4H-pyrazolo[3,4-d]pyrimidin-4-one (C19). tert-Butyl 3-hydroxyazetidine-1-carboxylate (2.50 g, 14.4 mmol) was dissolved in dichloromethane (20 mL) and treated with trifluoroacetic acid (3.7 mL, 48 mmol); the reaction was allowed to stir at room temp for about 18 h. Solvents were removed in vacuo, and the residue was mixed with acetonitrile (20 mL) and toluene (20 mL). Finely ground potassium carbonate (13.3 g, 96 mmol) was then added, followed by compound C18 (3.0 g, 9.6 mmol), and the mixture was heated to 90° C. for 5 h. After cooling to room temp, the reaction was concentrated in vacuo, diluted with water and extracted with methylene chloride. The combined organic layers were washed with saturated aqueous sodium chloride solution, dried over magnesium sulfate, filtered and concentrated. The resulting residue was purified via silica gel chromatography (Eluant: 2% MeOH in chloroform) to provide C19 as a solid. Yield: 1.95 g, 6.74 mmol, 70%. MS (APCI) m/z 287.9 (M−1). $^1$H NMR (400 MHz, CDCl$_3$) δ 1.33 (d, J=6.8 Hz, 3H), 1.90 (m, 2H), 2.44 (m, 2H), 2.76 (m, 2H), 3.17 (br dd, J=7, 4 Hz, 1H), 3.28 (br dd, J=7, 4 Hz, 1H), 3.58 (m, 3H), 4.44 (m, 1H), 5.28 (m, 1H), 8.12 (s, 1H).

Step 7. Synthesis of title compound 3. 2-Chloropyrimidine (79.2 mg, 0.691 mmol)), potassium tert-butoxide (163 mg, 1.45 mmol) and compound C19 (200 mg, 0.691 mmol) were combined in THF (5 mL), and the mixture was heated at 70° C. for 8 h. The reaction was cooled to room temp and concentrated in vacuo; the residue was partitioned between water and dichloromethane. The organic layer was washed with saturated aqueous sodium chloride solution, dried over magnesium sulfate, filtered and concentrated in vacuo. Purification via silica gel chromatography (Eluant: 0.5% to 1% MeOH in chloroform) provided 3 as a solid. Yield: 109 mg, 0.297 mmol, 43%. LCMS m/z 368.4 (M+1). $^1$H NMR (400 MHz, CDCl$_3$) δ 1.38 (v br s, 3H), 1.91 (m, 2H), 2.45 (m, 2H), 2.76 (m, 2H), 3.32 (v br s, 1H), 3.53 (v br m, 2H), 3.97 (v br s, 2H), 5.28 (m, 2H), 6.99 (t, J=4.9 Hz, 1H), 8.07 (s, 1H), 8.51 (d, J=5.0 Hz, 2H)

EXAMPLE 4

1-Isopropyl-6-[1-(3-phenoxyazetidin-1-yl)ethyl]-1,5-dihydro-4H-pyrazolo[3,4-d]pyrimidin-4-one resulting in some warming of the reaction mixture. The reaction was allowed to stir for about 18 h at room temp. Volatiles were then removed in vacuo, and the resulting viscous yellow oil was dissolved in dichloromethane and loaded onto a short column of silica gel. The column was eluted with dichloromethane (about 300 mL), followed by a 1:1 mixture of EtOAc and hexanes (about 750 mL), and the EtOAc: hexanes eluant was concentrated under reduced pressure to provide C20 as a pale yellow solid. Yield: 12.1 g, 80.6 mmol, 81%. LCMS m/z 151.1 (M+1). $^1$H NMR (400 MHz, DMSO-d$_5$) δ 1.26 (d, J=6.6 Hz, 6H), 4.41 (septet, J=6.5 Hz, 1H), 6.52 (br s, 2H), 7.53 (s, 1H).

Step 2. Preparation of 5-amino-1-isopropyl-1H-pyrazole-4-carboxamide (C21). Compound C20 (4.0 g, 27 mmol) was combined with concentrated sulfuric acid (about 10 mL) and stirred at room temp for 2 h. The reaction was then poured onto ice, adjusted to pH 9 with concentrated aqueous ammonium hydroxide, and extracted with a mixture of dichloromethane and THF. The organic layer was dried over magnesium sulfate, filtered and concentrated in vacuo to provide C21. Yield: 3.02 g, 18.0 mmol, 67%. LCMS m/z 169.3 (M+1). $^1$H NMR (400 MHz, CD$_3$OD) δ 1.39 (d, J=6.6 Hz, 6H), 4.39 (septet, J=6.6 Hz, 1H), 7.69 (s, 1H).

Step 3. Preparation of 5-[(2-bromopropanoyl)amino]-1-isopropyl-1H-pyrazole-4-carboxamide (C22). Compound C21 (16.8 g, 100 mmol) was dissolved in a mixture of anhydrous

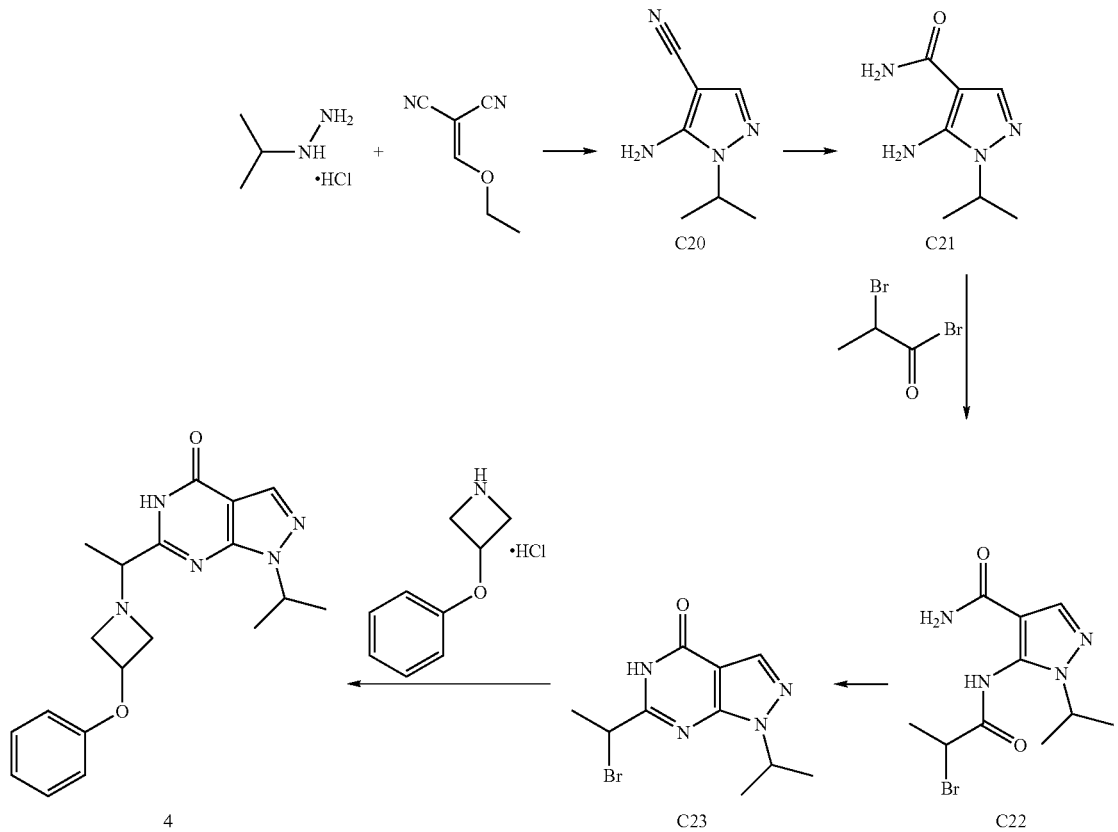

Step 1. Preparation of 5-amino-1-isopropyl-1H-pyrazole-4-carbonitrile (C20). (Ethoxymethylene)malononitrile (12.83 g, 105 mmol) and isopropylhydrazine hydrochloride (11.06 g, 100 mmol) were combined in EtOH (250 mL). Diisopropylethylamine (36.6 mL, 210 mmol) was added drop-wise, DMF (400 mL) and triethylamine (30.8 mL, 221 mmol) and cooled to 0° C. in an ice bath. 2-Bromopropanoyl bromide (43.2 g, 200 mmol) was added drop-wise, and the reaction was allowed to stir at 0° C. for 30 mins, then at room temp for 2 h. The reaction mixture was then concentrated to about one-fifth the original volume, and partitioned between EtOAc (800 mL) and 2N aqueous hydrochloric acid (800 mL). The organic layer was washed with saturated aqueous sodium bicarbonate solution (800 mL), saturated aqueous sodium chloride solution (800 mL), and dried over sodium sulfate. Filtration and removal of solvent under reduced pressure provided C22 as an orange residue, which was used in the next step without purification.

Step 4. Preparation of 6-(1-bromoethyl)-1-isopropyl-1,5-dihydro-4H-pyrazolo[3,4-d]pyrimidin-4-one (C23). para-Toluenesulfonic acid monohydrate (9.5 g, 50 mmol) was added to a suspension of crude C22 (from the previous step, ≦100 mmol) in anhydrous toluene (800 mL), the flask was equipped with a Dean-Stark trap, and the mixture was heated at reflux for 16 h. The reaction was then cooled to room temperature and diluted with EtOAc. The resulting mixture was washed with aqueous sodium bicarbonate solution and then with saturated aqueous sodium chloride solution, dried over sodium sulfate, filtered and concentrated in vacuo. The residue was purified via silica gel chromatography (Eluant: 100:1 chloroform: MeOH) to afford C23 (contaminated with a second component) as a beige solid. Yield: 11.2 g, <39.3 mmol, <39% over two steps. LCMS m/z 285.4 (M+1). $^1$H NMR (400 MHz, DMSO-$d_6$) (major component only): δ 1.45 (d, J=6.7 Hz, 3H), 1.46 (d, J=6.7 Hz, 3H), 1.99 (d, J=6.8 Hz, 3H), 4.96 (septet, J=6.6 Hz, 1H), 5.13 (q, J=6.8 Hz, 1H), 8.06 (s, 1H), 12.36 (br s, 1H).

Step 5. Synthesis of title compound 4. 3-Phenoxyazetidine hydrochloride (260 mg, 1.40 mmol), C23 (200 mg, 0.701 mmol) and potassium carbonate (290 mg, 2.1 mmol) were combined in acetonitrile (10 mL). The reaction mixture was stirred at room temperature for 2 h, then at reflux for 3 h. The reaction was concentrated in vacuo, diluted with water, and extracted with dichloromethane. The combined organic layers were washed with saturated aqueous sodium chloride solution, dried over magnesium sulfate, filtered and concentrated in vacuo. The resulting residue was chromatographed on silica gel (Eluant: 200:1 chloroform: MeOH) to provide 4. Yield: 149 mg, 0.42 mmol, 60%. MS (APCI) m/z 354.0 (M+1). $^1$H NMR (400 MHz, CDCl$_3$) δ 1.35 (d, J=6.8 Hz, 3H), 1.53 (d, J=6.6 Hz, 6H), 3.22 (br dd, J=6, 7 Hz, 1H), 3.39 (br dd, J=6.5, 6.5 Hz, 1H), 3.55 (q, J=6.6 Hz, 1H), 3.87 (m, 2H), 4.83 (m, 1H), 5.02 (septet, J=6.6 Hz, 1H), 6.77 (d, J=7.7 Hz, 2H), 6.97 (m, 1H), 7.28 (dd, J=8.5, 7.5 Hz, 2H), 8.06 (s, 1H), 9.85 (br s, 1H).

EXAMPLE 5

2-Fluoro-5-[(1-{1-[4-oxo-1-(tetrahydro-2H-pyran-4-yl)-4,5-dihydro-1H-pyrazolo[3,4-d]pyrimidin-6-yl]ethyl}azetidin-3-yl)oxy]benzonitrile

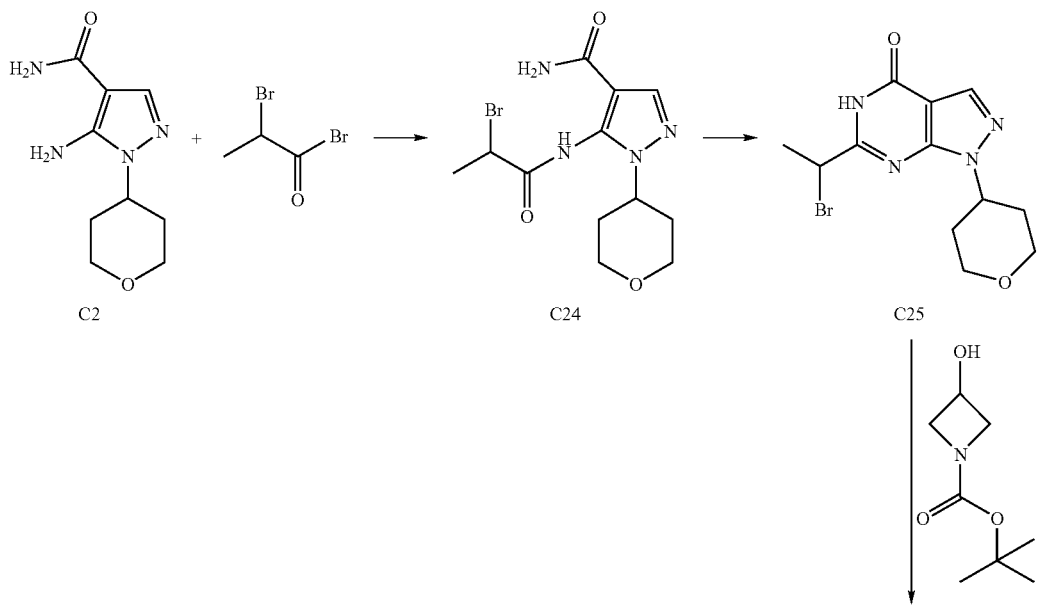

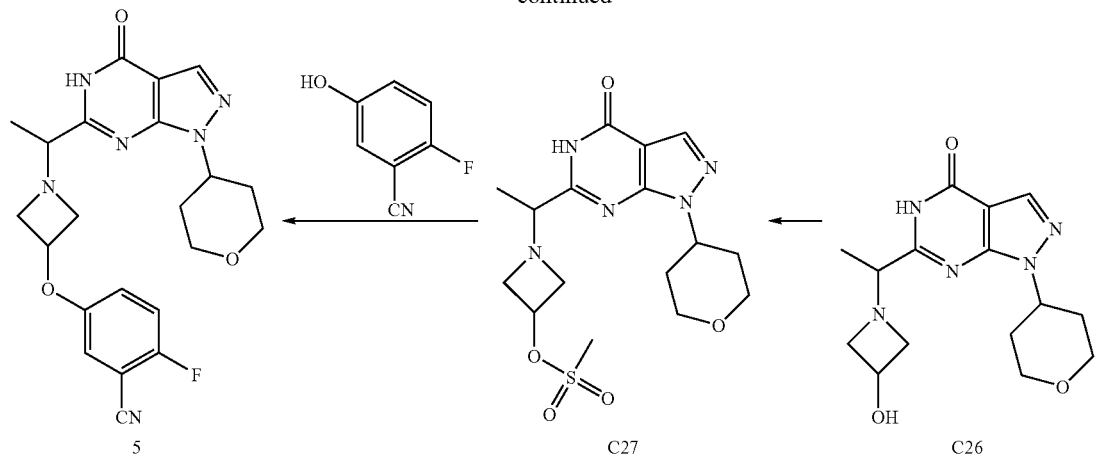

Step 1. Preparation of 5-[(2-bromopropanoyl)amino]-1-(tetrahydro-2H-pyran-4-yl)-1H-pyrazole-4-carboxamide (C24). A solution of C2 (5.0 g, 23.8 mmol) and triethylamine (3.65 mL, 26.2 mmol) in anhydrous DMF (50 mL) was cooled in an ice bath and treated drop-wise with 2-bromopropanoyl bromide (5.4 g, 25 mmol). The mixture was stirred at 0° C. for 30 mins, warmed to room temperature and stirred at ambient temperature for an additional 2 h. The reaction was partitioned between EtOAc (200 mL) and aqueous 2N hydrochloric acid (500 mL); the organic phase was washed with saturated aqueous sodium bicarbonate solution (400 mL), saturated aqueous sodium chloride solution (200 mL) and dried over sodium sulfate. Filtration and concentration of the filtrate provided crude C24 as an orange residue, which was used in the next step without purification.

Step 2. Preparation of 6-(1-bromoethyl)-1-(tetrahydro-2H-pyran-4-yl)-1,5-dihydro-4H-pyrazolo[3,4-o]pyrimidin-4-one (C25). A suspension of C24 from the previous step (≦23.8 mmol) in toluene (100 mL) was treated with para-toluenesulfonic acid (2.3 g, 11.9 mmol) and heated to reflux for 6 h using a Dean-Stark trap. The mixture was then cooled to room temp, diluted with EtOAc and washed with aqueous sodium bicarbonate solution followed by saturated aqueous sodium chloride solution. The organic layer was dried over sodium sulfate, filtered and concentrated in vacuo to provide a residue that was purified by silica gel chromatography (Eluant: 100:1 chloroform: MeOH). The resulting yellow-orange solid was subjected to a second silica gel column (Eluant 100:1 chloroform: MeOH) to provide C25 as a yellow solid. Yield: 1.1 g, 3.36 mmol, 14% over two steps. Purity: 85% by LCMS. LCMS m/z 327.0, 329.1 for the two bromine isotopes (M+1). $^1$H NMR (400 MHz, $CD_3OD$) δ 1.92 (m, 2H), 2.06 (d, J=6.3 Hz, 3H), 2.31 (m, 2H), 3.63 (m, 2H), 4.08 (m, 2H), 4.94 (m, 1H), 5.09 (q, J=6.6 Hz, 1H), 8.05 (s, 1H).

Step 3. Preparation of 6-[1-(3-hydroxyazetidin-1-yl)ethyl]-1-(tetrahydro-2H-pyran-4-yl)-1,5-dihydro-4H-pyrazolo[3,4-d]pyrimidin-4-one (C26). A solution of t-butyl 3-hydroxyazetidine-1-carboxylate (519 mg, 3.00 mmol) in dichloromethane (10 mL) was treated with trifluoroacetic acid (0.77 mL, 10 mmol), and the resulting mixture was stirred at room temperature for about 18 h. Additional trifluoroacetic acid (0.5 mL) was added, and the reaction was stirred for an additional 3 h. Solvents were removed under reduced pressure, and acetonitrile (40 mL) was added to the residue, followed by solid potassium carbonate (2.76 g, 20 mmol), and C25 (654 mg, 2.00 mmol). The mixture was stirred at room temp for 2 h, then heated to 90° C. for 3 h. The reaction was cooled to room temp, diluted with dichloromethane and filtered; the remaining solid was washed with additional dichloromethane. The combined filtrates were concentrated in vacuo, then subjected to silica gel chromatography (Eluant: 40:1 to 20:1 chloroform: MeOH) to provide C26. Yield: 368 mg, 1.15 mmol, 58%. MS (APCI) m/z 320.0 (M+1). NMR (400 MHz, $CDCl_3$) δ 1.34 (d, J=6.8 Hz, 3H), 1.91 (m, 2H), 2.38 (dddd, apparent qd, J=12, 12, 12, 4.6 Hz, 2H), 3.17 (br s, 1H), 3.28 (br s, 1H), 3.52-3.68 (m, 5H), 4.14 (dd, J=11.3, 3.6 Hz, 2H), 4.46 (m, 1H), 4.85 (tt, J=11.6, 4.2 Hz, 1H), 8.10 (s, 1H).

Step 4. Preparation of 1-{1-[4-oxo-1-(tetrahydro-2H-pyran-4-yl)-4,5-dihydro-1H-pyrazolo[3,4-d]pyrimidin-6-yl]ethyl}azetidin-3-yl methanesulfonate (C27). A solution of C26 (1.34 g, 4.20 mmol) in dichloromethane (30 mL) was treated with triethylamine (1.17 mL, 8.41 mmol) and then drop-wise with methanesulfonyl chloride (0.49 mL, 6.3 mmol). The reaction was allowed to stir at room temperature for about 18 h, then saturated aqueous sodium carbonate solution was added, and the aqueous layer was extracted twice with dichloromethane. The combined organic layers were dried over magnesium sulfate, filtered and concentrated. The residue was purified twice by silica gel chromatography (Gradient: 0% to 4% MeOH in dichloromethane), to afford C27 as a solid. Yield: 1.12 g, 2.82 mmol, 67%. LCMS m/z 398.3 (M+1). $^1$H NMR (400 MHz, $CD_3OD$) δ 1.36 (d, J=6.6 Hz, 3H), 1.90 (m, 2H), 2.29 (m, 2H), 3.10 (s, 3H), 3.39 (dd, J=8.3, 5.4 Hz, 1H), 3.44 (dd, J=8.4, 5.3 Hz, 1H), 3.62 (m, 3H), 3.76 (br dd, J=7.4, 7.4 Hz, 1H), 3.84 (br dd, J=7.4, 7.4 Hz, 1H), 4.10 (br d, J=11.6 Hz, 2H), 4.97 (tt, J=11.6, 4.2 Hz, 1H), 5.15 (m, 1H), 8.03 (s, 1H).

Step 5. Synthesis of title compound 5. Compound C27 (50 mg, 0.13 mmol), 2-fluoro-5-hydroxybenzonitrile (34.5 mg, 0.25 mmol) and potassium carbonate (52.2 mg, 0.38 mmol) were combined in acetonitrile (5 mL), and the mixture was heated at reflux for about 18 h. Removal of solvents in vacuo provided a residue which was purified by silica gel chromatography (Gradient: 1% to 3% MeOH in dichloromethane) to provide 5 as a solid. Yield: 19 mg, 0.043 mmol, 33%. LCMS m/z 439.3 (M+1). $^1$H NMR (400 MHz, $CD_3OD$) δ 1.37 (d, J=6.6 Hz, 3H), 1.89 (m, 2H), 2.29 (dddd, J=12, 12, 12, 5 Hz, 2H), 3.28 (dd, J=8.3, 5.4 Hz, 1H), 3.35 (m, 1H), 3.61 (m, 3H), 3.86 (br dd, J=7, 7 Hz, 1H), 3.92 (br dd, J=7, 7 Hz, 1H), 4.09 (br dd, J=11.6, 3.7 Hz, 2H), 4.90 (m, obscured by water peak, 1H assumed), 4.98 (tt, J=11.6, 4.3 Hz, 1H), 7.19 (m, 2H), 7.28 (m, 1H), 8.03 (s, 1H).

EXAMPLE 6
1-Cyclopentyl-6-[(1R)-1-(3-pyrimidin-2-ylazetidin-1-yl)ethyl]-1,5-dihydro-4H-pyrazolo[3,4-d]pyrimidin-4-one
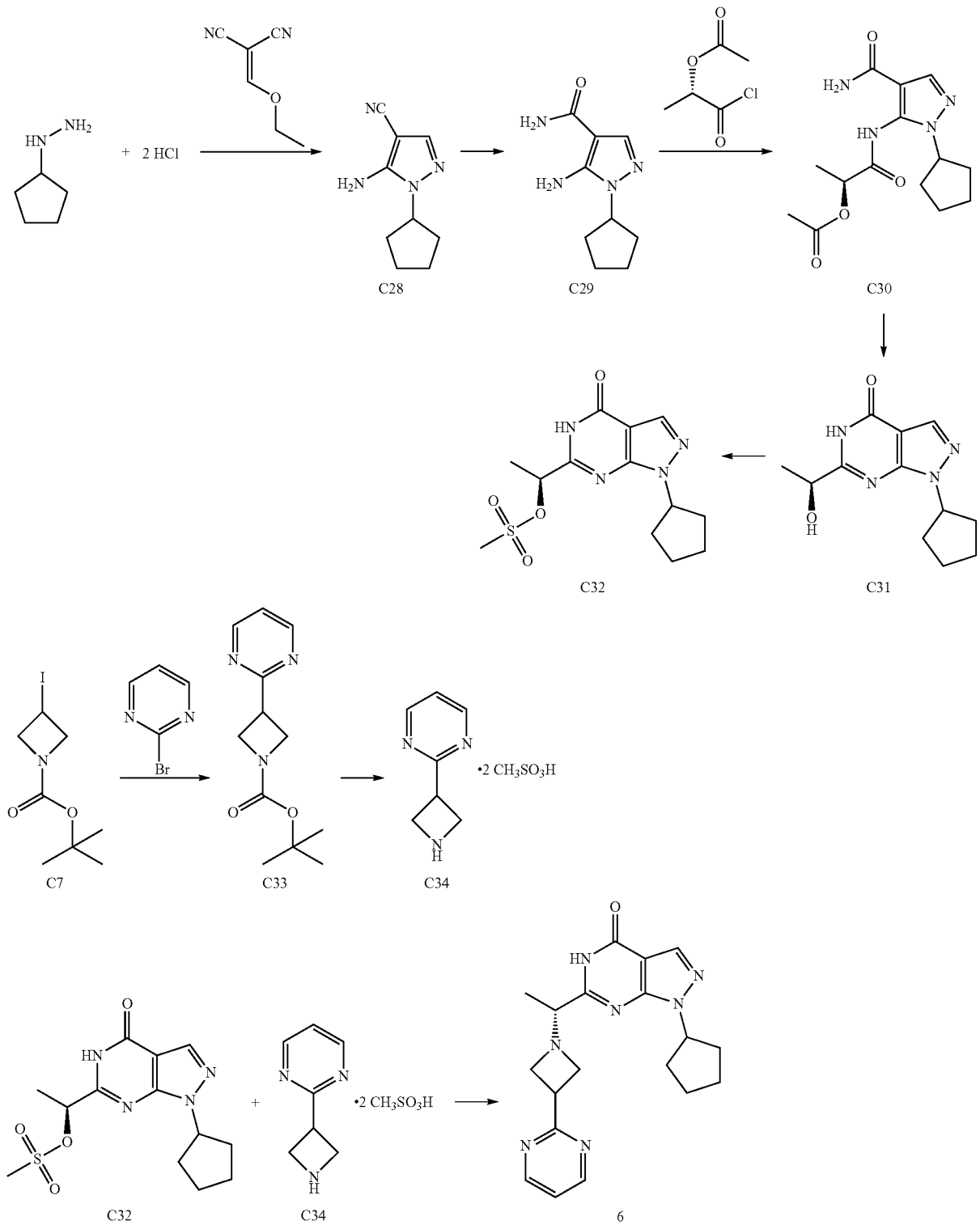

Step 1 Preparation of (1S)-1-(1-cyclopentyl-4-oxo-4,5-dihydro-1H-pyrazolo[3,4-d]pyrimidin-6-yl)ethyl methanesulfonate (C32)

A. Preparation of 5-amino-1-cyclopentyl-1H-pyrazole-4-carbonitrile (C28). A solution of cyclopentylhydrazine dihydrochloride (50.9 g, 0.294 mol) in anhydrous EtOH (640 mL) was cooled to 0° C. and treated with sodium ethoxide (40.0 g, 0.588 mol) in portions over 2 h. The mixture was stirred at 0° C. for 45 mins, then treated drop-wise with a solution of (ethoxymethylene)malononitrile (35.9 g, 0.294 mol) in EtOH over 1 h. Following the addition, the reaction was stirred at 0° C. for 30 mins, then warmed to room temperature over 1 h. The mixture was heated at reflux for 2 h, cooled to room temperature and concentrated in vacuo, after which the residue was mixed with water, and the resulting suspension was filtered. The collected solids were washed three times with water, then three times with a 1:1 mixture of diethyl ether and hexanes, providing C28 as a beige solid.

Yield: 44.0 g, 0.250 mol, 85%. $^1$H NMR (400 MHz, CDCl$_3$) δ 1.69 (m, 2H), 1.92 (m, 2H), 2.06 (m, 4H), 4.34 (m, 1H), 7.50 (s, 1H).

B. Preparation of 5-amino-1-cyclopentyl-1H-pyrazole-4-carboxamide (C29). Compound C28 (44.0 g, 0.250 mol) was added portion-wise to concentrated sulfuric acid (200 mL) at 0° C. After completion of the addition, the reaction mixture was allowed to warm from 0° C. to room temperature and stirred for about 18 h. The reaction mixture was poured onto ice, and then brought to pH 9-10 by addition of concentrated aqueous ammonium hydroxide solution. The resulting solids were collected by filtration, washed three times with water, then washed three times with a 1:1 mixture of diethyl ether and hexanes to provide C29 as an off-white solid. Yield: 39.8 g, 0.205 mol, 82%. LCMS m/z 195.4 (M+1). $^1$H NMR (400 MHz, DMSO-d$_6$) δ 1.57 (m, 2H), 1.80 (m, 4H), 1.92 (m, 2H), 4.52 (m, 1H), 6.15 (s, 2H), 6.61 (br s, 1H), 7.15 (br s, 1H), 7.62 (s, 1H).

C. Preparation of (1S)-2-[(4-carbamoyl-1-cyclopentyl-1H-pyrazol-5-yl)amino]-1-methyl-2-oxoethyl acetate (C30). (1S)-2-Chloro-1-methyl-2-oxoethyl acetate (12 mL, 95 mmol) was slowly added drop-wise to an ice-cooled suspension of C29 (16.4 g, 84.4 mmol) in anhydrous 1,4-dioxane (200 mL). After being stirred at 0° C. for 40 mins, the reaction mixture was heated at reflux for 2 h. It was then cooled to room temperature and concentrated in vacuo, to afford C30, which was used directly in the next step.

D. Preparation of 1-cyclopentyl-6-[(1S)-1-hydroxyethyl]-1,5-dihydro-4H-pyrazolo[3,4-d]pyrimidin-4-one (C31). Compound C30 from the previous step (assumed 84.4 mmol) was dissolved in a mixture of water (200 mL) and THF (20 mL). To this solution was added potassium carbonate (60 g, 0.43 mol), and the resulting mixture was heated at 50° C. for 2 days. The reaction mixture was cooled to room temp and extracted with EtOAc (2×200 mL). The combined organic extracts were washed with saturated aqueous sodium chloride solution, dried over sodium sulfate, filtered and concentrated in vacuo to provide C31 as a tin solid. Yield: 17.5 g, 70.5 mmol, 84% over 2 steps. LCMS m/z 249.4 (M+1). $^1$H NMR (400 MHz, DMSO-d$_6$) δ 1.41 (d, J=6.6 Hz, 3H), 1.67 (m, 2H), 1.90 (m, 4H), 2.06 (m, 2H), 4.61 (q, J=6.6 Hz, 1H), 5.13 (m, 1H), 8.02 (s, 1H).

E. Preparation of C32. A solution of C31 (93% purity by weight, 87.74 g, 328.6 mmol) in 2-methyltetrahydrofuran (408 mL) was treated with 4-methylmorpholine (54.4 mL, 495 mmol), followed, after 5 mins, by methanesulfonyl chloride (26.7 mL, 345 mmol). The temperature of the reaction was maintained between 25 and 40° C. for 3 h. After cooling to room temp, the reaction mixture was filtered through Celite to remove morpholine salts, and the filter cake was washed with 5-10 volumes of 2-methyltetrahydrofuran. The filtrate was concentrated in vacuo, then purified by silica gel chromatography (Eluant: 9:1 EtOAc:hexanes). Pure fractions were combined and concentrated to afford C32 as a slightly yellow solid. Yield: 48.6 g, 149 mmol, 45%. Mixed fractions were combined and concentrated to provide 40 grams of a residue which was purified by trituration with methyl tert-butyl ether (100 mL) to provide additional C32 as a white solid. Combined yield: 79.5 g, 244 mmol, 74%. LCMS m/z 325.1 (M–1). NMR (400 MHz, CDCl$_3$) δ 1.75 (m, 2H), 1.86 (d, J=6.8 Hz, 3H), 1.99 (m, 2H), 2.13 (m, 4H), 3.23 (s, 3H), 5.18 (m, 1H), 5.70 (q, J=6.7 Hz, 1H), 8.07 (s, 1H), 11.04 (br s, 1H).

Step 2 Preparation of 2-azetidin-3-ylpyrimidine dimethanesulfonate (C34).

A. Preparation of tert-butyl 3-pyrimidin-2-ylazetidine-1-carboxylate (C33). Zinc powder (150.1 g, 2.30 mol) and molecular sieves (50 g) were combined in a reaction flask and flame-dried under vacuum for 10 mins. Once the flask had returned to room temperature, it was charged with THF (4 L), and 1,2-dibromoethane (24.4 mL, 0.28 mol) was added. The reaction mixture was heated to 50° C. for 10 mins, then allowed to come to ambient temperature, at which time trimethylsilyl chloride (33.5 mL, 0.264 mol) was added {Caution: slightly exothermic}. The mixture was allowed to stir at room temperature for about 18 h. Slow addition of C7 (500 g, 1.77 mol) over 1.5 h was followed by stirring for an additional 18 h. In a separate flask, 2-bromopyrimidine (253 g, 1.59 mol) was combined with molecular sieves (85 g) in THF (1.3 L), and the mixture was degassed. This mixture was treated with tetrakis(triphenylphosphine)palladium(0) (32.7 g, 0.0283 mol), then added to the flask containing the reaction mixture from C7. The reaction was stirred for 25 h, and then filtered through Celite. The filtrate was concentrated under reduced pressure, then partitioned between saturated aqueous sodium carbonate solution (2 L) and EtOAc (2 L). The aqueous layer was extracted with EtOAc (2×2 L), and the combined organic layers were dried over sodium sulfate and concentrated in vacuo. The resulting yellow liquid residue was triturated with methyl tert-butyl ether (500 mL), and the precipitate was removed by filtration. Partial concentration of the filtrate resulted in precipitation of a solid; the mixture at this point was cooled in an ice-water bath. Filtration then provided a solid, which was washed with a minimum quantity of cold methyl tert-butyl ether to afford C33 as a white solid, which was taken directly into the next step. Yield: 131 g, 0.557 mol, 31%. GCMS m/z 180 ([M-tert-butyl]+1); 136 ([M-BOC]+1). $^1$H NMR (300 MHz, CDCl$_3$) δ 1.45 (s, 9H), 4.0 (m, 1H), 4.3 (m, 4H), 7.2 (t, 1H), 8.75 (d, 2H).

B. Preparation of compound C34. Methanesulfonic acid (108.3 mL, 1.67 mol) was added to an ice-cold solution of C33 (131 g, 0.557 mol, from previous step) in dichloromethane:dioxane (9:1 ratio, 1 L). The mixture was allowed to warm to room temperature over about 18 h, with stirring. The precipitate was filtered and washed with methyl tert-butyl ether to provide C34 as a white solid. Yield: 180 g, 0.550 mol, 99%. LCMS m/z 136.2 (M+1). $^1$H NMR (300 MHz, D$_2$O) δ 2.55 (s, 6H), 4.33 (m, 5H), 7.64 (t, J=5.3 Hz, 1H), 8.90 (d, J=5.2 Hz, 2H). $^{13}$C NMR (75 MHz, D$_2$O) δ 36.47, 38.53, 49.98, 121.63, 158.08, 164.37.

Step 3. Synthesis of title compound 6. Compounds C32 (35 g, 107 mmol) and C34 (38.62 g, 118 mmol) were mixed with acetonitrile (700 mL), and the heterogeneous reaction mixture was treated with triethylamine (134 mL, 961 mmol) and heated to 80° C. for 3.5 h. The reaction became homogeneous and light yellow. The product was concentrated by distillation at a pot temperature of 80-90° C., until 350-500 mL of acetonitrile remained. It was then allowed to crystallize as it cooled to room temperature. The mixture was stirred for about 18 h and then filtered to obtain 6 as a solid. Yield: 21 g, 57.5 mmol, 54%. For samples of 6 prepared under similar conditions, but chromatographed rather than crystallized, the minor enantiomer of the product was removed by chiral chromatography using a Chiralpak AD-H column (5 μm; 2.1×25 cm; mobile phase: 70:30 carbon dioxide: MeOH; flow rate 65 g/min). Compound 6 was the second-eluting enantiomer, retention time approximately 3.35 min. LCMS m/z 366.2 (M+1). $^1$H NMR (400 MHz, CDCl$_3$) δ 1.33 (d, J=6.6 Hz, 3H), 1.72 (m, 2H), 1.97 (m, 2H), 2.11 (m, 4H), 3.58 (m, 2H), 3.71 (dd, J=7.1, 7.1 Hz, 1H), 3.79 (m, 2H), 4.00 (m, 1H), 5.16 (m, 1H), 7.19 (t, J=4.9 Hz, 1H), 8.05 (s, 1H), 8.72 (d, J=5.0 Hz, 2H), 9.86 (br s, 1H). $^{13}$C NMR (100 MHz, CDCl$_3$) δ 18.07, 24.73, 32.38, 32.45, 37.61, 56.69, 57.69, 57.78, 65.09, 105.09, 119.00, 134.54, 157.11, 157.93, 160.39, 169.82 (one aromatic signal not observed).

EXAMPLE 7

6-[(1R)-1-(3-Quinolin-2-ylazetidin-1-yl)ethyl]-1-(tetrahydro-2H-pyran-4-yl)-1,5-dihydro-4H-pyrazolo[3,4-d]pyrimidin-4-one

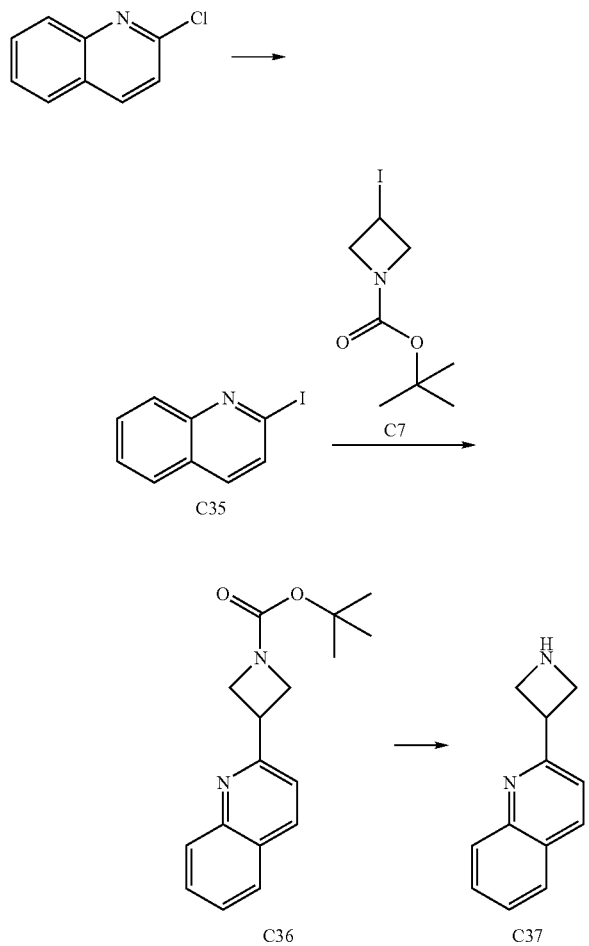

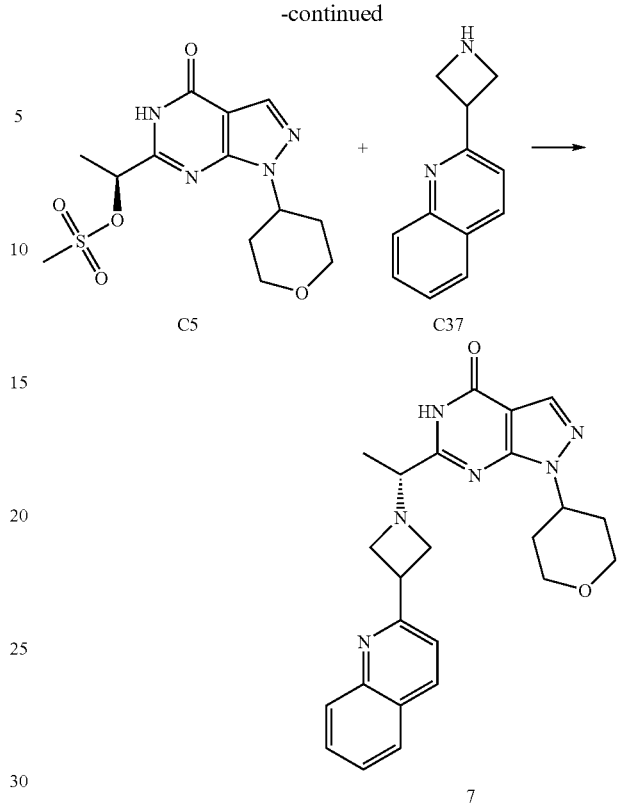

Step 1 Preparation of 2-azetidin-3-ylquinoline (C37)

A. Preparation of 2-iodoquinoline (C35). 2-Chloroquinoline (8.18 g, 50.0 mmol), trimethylsilyl chloride (98%, 6.48 mL, 50.0 mmol) and sodium iodide (98%, 15.3 g, 100 mmol) were mixed with propionitrile (50 mL) and heated at reflux for about 18 h. The reaction was then cooled to room temperature and quenched with aqueous sodium hydroxide solution (1N, 25 mL). After extraction with EtOAc, the combined organic layers were dried over sodium sulfate, filtered and concentrated in vacuo. Purification via silica gel chromatography (Gradient: 0-100% ethyl acetate in heptane) afforded C35. Yield: 5.33 g, 20.9 mmol, 42%. LCMS m/z 255.9 (M+1). $^1$H NMR (400 MHz, CDCl$_3$) δ 7.57 (ddd, J=8.1, 6.9, 1.2 Hz, 1H), 7.75 (m, 4H), 8.05 (br d, J=8.5 Hz, 1H).

B. Preparation of tert-butyl 3-quinolin-2-ylazetidine-1-carboxylate (C36). Compound C36 was prepared according to the general procedure for the synthesis of C8 in Example 1, except that C35 was used in place of 2-bromo-4-methylpyridine, and the reaction was stirred at 50° C. for 18 h after addition of the palladium catalyst and C35. Purification was carried out via silica gel chromatography (Gradient 0-100% EtOAc in heptane) to provide C36. Yield: 1.05 g, 3.69 mmol, 47%. LCMS m/z 285.1 (M+1). $^1$H NMR (400 MHz, CDCl$_3$) δ 1.48 (s, 9H), 4.07 (m, 1H), 4.30 (dd, J=8.6, 5.9 Hz, 2H), 4.41 (dd, J=8.7, 8.7 Hz, 2H), 7.43 (d, J=8.5 Hz, 1H), 7.53 (ddd, J=8.1, 6.9, 1.1 Hz, 1H), 7.72 (ddd, J=8.4, 6.9, 1.4 Hz, 1H), 7.81 (br d, J=8.1 Hz, 1H), 8.07 (br d, J=8.5 Hz, 1H), 8.16 (d, J=8.5 Hz, 1H).

C. Preparation of C37. A solution of C36 (1.0 g, 3.5 mmol) in methanolic hydrochloric acid (1.25M, 50 mL, 62 mmol) was stirred at room temperature for 18 h. The reaction mixture was concentrated in vacuo, and extracted with dichloromethane after conversion of product to the free base with 6N aqueous sodium hydroxide solution. Removal of solvent in vacuo provided C37. Yield: 310 mg, 1.68 mmol, 48%. LCMS m/z 185.2 (M+1). ¹H NMR (400 MHz, DMSO-d₆) δ 3.80 (dd, J=8.0, 8.0 Hz, 2H), 3.91 (dd, J=7.4, 7.4 Hz, 2H), 4.16 (m, 1H), 7.54 (d, J=8.3 Hz, 1H), 7.56 (ddd, J=8.1, 6.9, 1.1 Hz, 1H), 7.74 (ddd, J=8.4, 6.9, 1.6 Hz, 1H), 7.96 (m, 2H), 8.32 (d, J=8.5 Hz, 1H).

Step 2. Synthesis of title compound 7. Compound 7 was prepared according to the general procedure for the synthesis of 1 in Example 1, except that C37 was used in place of C9, and the chromatography was carried out with a gradient of 0-10% EtOAc in EtOH, to afford 7 as a glass. Yield: 480 mg, 1.11 mmol, 79%. LCMS m/z 431.1 (M+1). ¹H NMR (400 MHz, CDCl₃) δ 1.38 (d, J=6.6 Hz, 3H), 1.93 (br d, J=12.6 Hz, 2H), 2.39 (m, 2H), 3.63 (m, 4H), 3.79 (m, 1H), 3.87 (m, 2H), 4.06 (m, 1H), 4.15 (m, 2H), 4.86 (tt, J=11.7, 4 Hz, 1H), 7.40 (d, J=8.3 Hz, 1H), 7.54 (ddd, J=8.1, 6.9, 1.2 Hz, 1H), 7.73 (ddd, J=8.4, 6.9, 1.4 Hz, 1H), 7.82 (dd, J=8.2, 1.1 Hz, 1H), 8.08 (s, 1H), 8.09 (d, J=8.3 Hz, 1H), 8.15 (d, J=8.5 Hz, 1H).

EXAMPLE 8

6-{(1R)-1-[3-(6-Methylpyridin-2-yl)azetidin-1-yl]
ethyl}-1-(tetrahydro-2H-pyran-4-yl)-1,5-dihydro-
4H-pyrazolo[3,4-d]pyrimidin-4-one

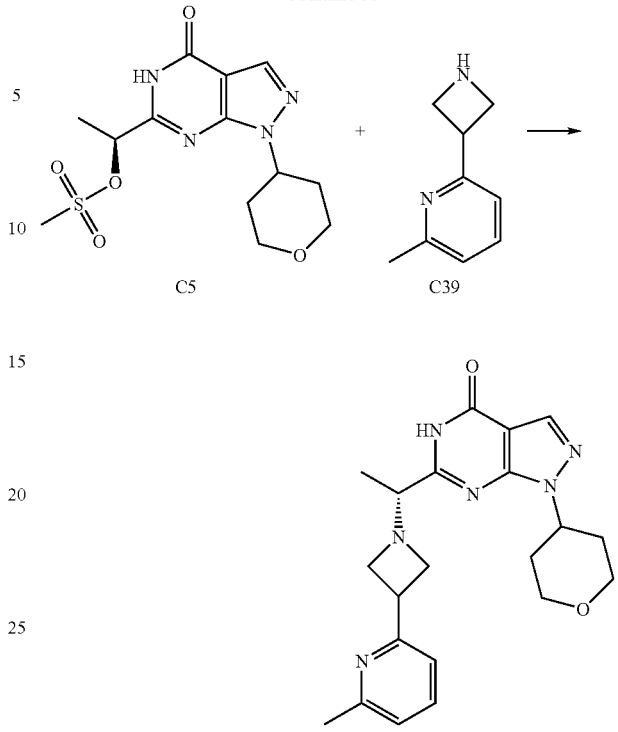

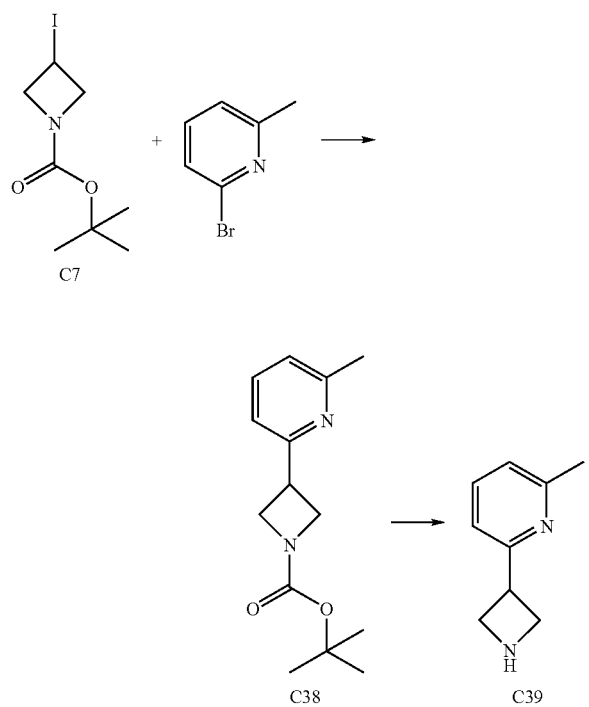

Step 1 Preparation of 2-azetidin-3-yl-6-methylpyridine (C39)

A. Preparation of tert-butyl 3-(6-methylpyridin-2-yl)azetidine-1-carboxylate (C38). Compound C38 was prepared according to the general procedure for the synthesis of C8 in Example 1, except that 2-bromo-6-methylpyridine was used in place of 2-bromo-4-methylpyridine. Yield: 397 mg, 1.60 mmol, 45%. LCMS m/z 249.2 (M+1). ¹H NMR (400 MHz, CDCl₃) δ 1.46 (s, 9H), 2.54 (s, 3H), 3.85 (tt, J=8.8, 6.1 Hz, 1H), 4.13 (dd, J=8.6, 6.1 Hz, 2H), 4.30 (dd, J=8.8, 8.8 Hz, 2H), 7.02 (d, J=7.7 Hz, 1H), 7.08 (d, J=7.9 Hz, 1H), 7.55 (dd, J=7.7, 7.7 Hz, 1H). ¹³C NMR (100 MHz, CDCl₃) δ 24.72, 28.65, 35.42, 55.2 (v broad), 79.61, 118.32, 121.61, 137.05, 156.75, 158.39, 160.60.

B. Preparation of compound C39. Compound C39 was prepared according to the general procedure for the synthesis of C9 in Example 1, except that C38 was used instead of C8. Yield: 74.1 mg, 0.50 mmol, 100%. LCMS m/z 149.1 (M+1).

Step 2. Synthesis of compound 8. Compound 8 was prepared according to the general procedure for the synthesis of 1 in Example 1, except that C39 was used instead of C9. Compound 8 was isolated as an off-white solid. Yield: 41 mg, 0.104 mmol, 31%. LCMS m/z 395.1 (M+1). ¹H NMR (400 MHz, CDCl₃) δ 1.33 (d, J=6.6 Hz, 3H), 1.91 (br d, J=12.6 Hz, 2H), 2.38 (m, 2H), 2.54 (s, 3H), 3.45 (dd, J=6.5, 6.5 Hz, 1H), 3.55-3.65 (m, 4H), 3.72-3.85 (m, 3H), 4.14 (dd, J=11.4, 3.9 Hz, 2H), 4.84 (tt, J=11.6, 4.2 Hz, 1H), 7.02 (d, J=7.7 Hz, 1H), 7.05 (d, J=7.7 Hz, 1H), 7.53 (dd, J=7.7, 7.7 Hz, 1H). 8.06 (s, 1H). ¹³C NMR (100 MHz, CDCl₃) δ 18.19, 24.54, 32.17, 36.64, 53.69, 57.53, 58.65, 65.16, 67.01, 105.31, 118.39, 121.25, 134.72, 136.64, 151.89, 157.86, 158.08, 159.73, 160.80.

EXAMPLE 9

6-{(1R)-1-[3-(4-Fluorophenoxy)azetidin-1-yl]ethyl}-1-(tetrahydro-2H-pyran-4-yl)-1,5-dihydro-4H-pyrazolo[3,4-d]pyrimidin-4-one

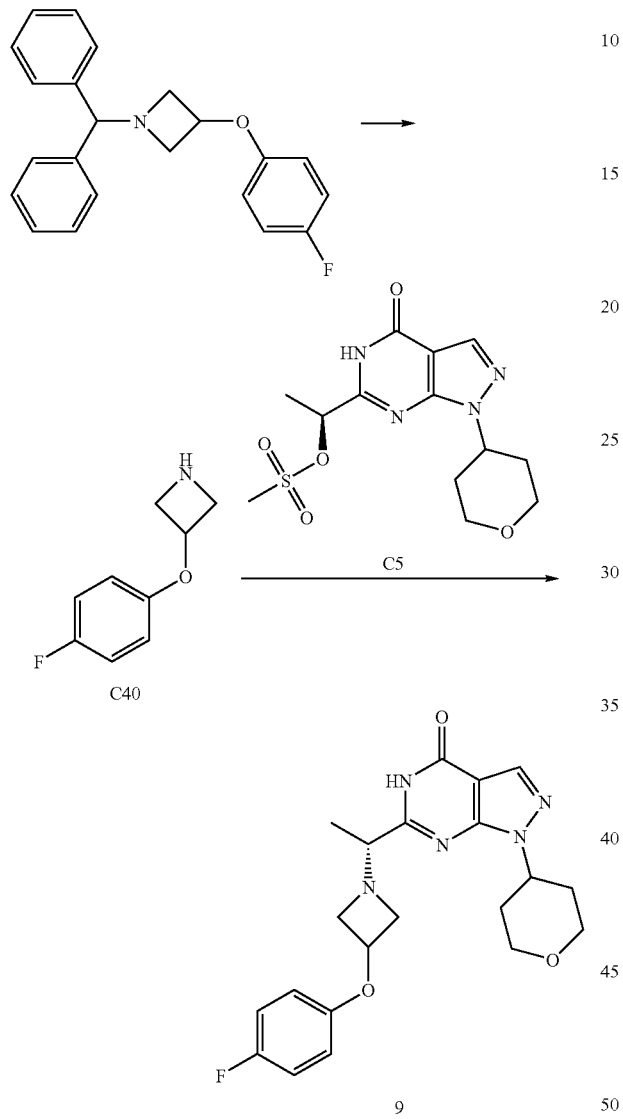

Step 1. Preparation of 3-(4-fluorophenoxy)azetidine (C40). Palladium hydroxide (500 mg) and 1-(diphenylmethyl)-3-(4-fluorophenoxy)azetidine (500 mg, 1.50 mmol) were combined in ethanol (50 mL) and hydrogenated at 50 psi for 18 h. The reaction mixture was then filtered through Celite and concentrated in vacuo. The residue was purified via silica gel chromatography (Eluant: 00:5:2 chloroform: MeOH: concentrated aqueous ammonium hydroxide) to provide C40. Yield: 188 mg, 1.12 mmol, 75%. LCMS m/z 168.1 (M+1). $^1$H NMR (400 MHz, CDCl$_3$) δ 2.44 (br s, 1H), 3.76 (m, 2H), 3.89 (m, 2H), 4.91 (m, 1H), 6.66 (m, 2H), 6.93 (m, 2H). $^{13}$C NMR (100 MHz, CDCl$_3$) δ 54.55, 70.81, 115.43, 115.51, 115.76, 115.99, 152.96, 156.15, 158.53.

Step 2. Synthesis of title compound 9. Compound 9 was prepared according to the general procedure for the synthesis of 1 in Example 1, except that C40 was used in place of C9. Yield: 258 mg, 0.624 mmol, 85%. LCMS m/z 414.4 (M+1). $^1$H NMR (400 MHz, CDCl$_3$) δ 1.36 (d, J=6.6 Hz, 3H), 1.91 (br d, J=12.6 Hz, 2H), 2.37 (m, 2H), 3.23 (br s, 1H), 3.40 (m, 1H), 3.61 (m, 3H), 3.88 (br s, 2H), 4.14 (dd, J=11.5, 4.0 Hz, 2H), 4.75-4.88 (m, 2H), 6.71 (m, 2H), 6.97 (m, 2H), 8.06 (s, 1H). This material (80% ee) was subjected to chromatography using a Chiralpak AS-H column (Eluant: 85:15 carbon dioxide: MeOH), followed by silica gel chromatographic purification (Eluant: 100:1 chloroform: MeOH) to provide the pure enantiomer 9. Yield: 102 mg. Enantiomeric excess: 100%; LCMS and $^1$H NMR essentially unchanged.

EXAMPLE 10

6-{(1R)-1-[3-(5-Chloropyrimidin-2-yl)azetidin-1-yl]ethyl}-1-(tetrahydro-2H-pyran-4-yl)-1,5-dihydro-4H-pyrazolo[3,4-d]pyrimidin-4-one

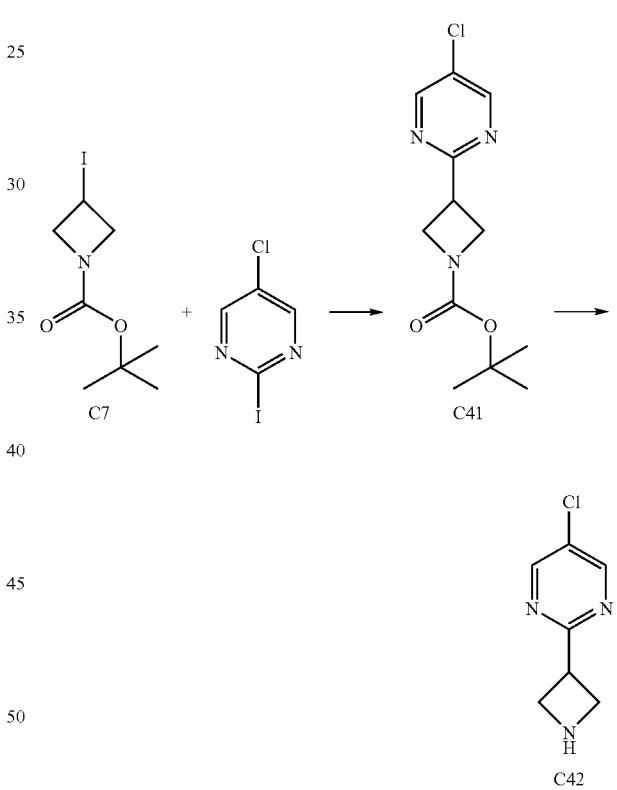

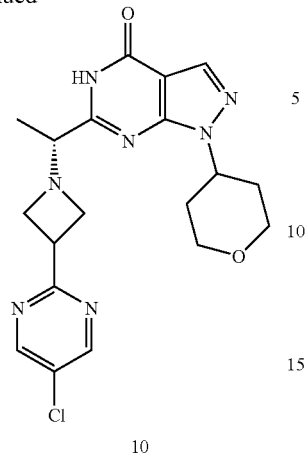

10

Step 1 Preparation of 2-azetidin-3-yl-5-chloropyrimidine (C42).

A. Preparation of tert-butyl 3-(5-chloropyrimidin-2-yl)azetidine-1-carboxylate (C41). Compound C41 was prepared according to the general procedure for the synthesis of C8 in Example 1, except that 5-chloro-2-iodopyrimidine was used in place of 2-bromo-4-methylpyridine, the reaction was carried out at room temperature, and the chromatographic purification was carried out using 1:4 EtOAc:heptane. Yield: 1.13 g, 4.19 mmol, 42%. LCMS m/z 270.1 (M+1). $^1$H NMR (400 MHz, CDCl$_3$) δ 1.44 (s, 9H), 4.00 (tt, J=8.8, 6.0 Hz, 1H), 4.21 (dd, J=8.5, 6.0 Hz, 2H), 4.31 (dd, J=13.7, 8.7 Hz, 2H), 8.66 (s, 2H). $^{13}$C NMR (100 MHz, CDCl$_3$) δ 28.32, 35.59, 54.0 (br), 79.48, 129.47, 155.69, 156.32, 168.01.

B. Synthesis of compound C42. Compound C42 was prepared according to the general procedure for the synthesis of C9 in Example 1, except that C41 was used instead of C8. Yield: 170 mg, 1.00 mmol, 100%.

LCMS m/z 170.1 (M+1).

Step 2. Synthesis of title compound 10. Compound 10 was prepared according to the general procedure for the synthesis of 1 in Example 1, except that C42 was used in place of C9. Yield: 240 mg, 0.577 mmol, 86%. LCMS m/z 416.0 (M+1). $^1$H NMR (400 MHz, CDCl$_3$) δ 1.33 (d, J=6.8 Hz, 3H), 1.91 (br d, J=12.6 Hz, 2H), 2.38 (m, 2H), 3.52-3.64 (m, 4H), 3.68 (dd, J=7.3, 7.3 Hz, 1H), 3.78 (dd, J=7.7, 7.7 Hz, 2H), 3.99 (m, 1H), 4.14 (dd, J=11.3, 4.0 Hz, 2H), 4.83 (tt, J=11.6, 4.2 Hz, 1H), 8.06 (s, 1H), 8.67 (s, 2H), 9.9 (br s, 1H). $^{13}$C NMR (100 MHz, CDCl$_3$) δ 18.02, 32.18, 37.06, 53.76, 56.80, 57.83, 65.02, 67.03, 105.32, 129.44, 134.74, 151.88, 155.60, 157.81, 160.52, 167.62.

EXAMPLE 11

6-[(1R)-1-(3-Phenylazetidin-1-yl)ethyl]-1-(tetrahydro-2H-pyran-4-yl)-1,5-dihydro-4H-pyrazolo[3,4-d]pyrimidin-4-one

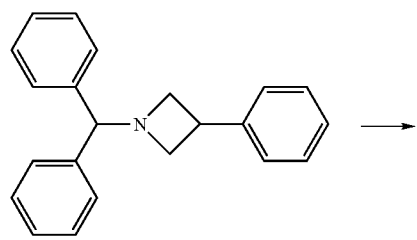

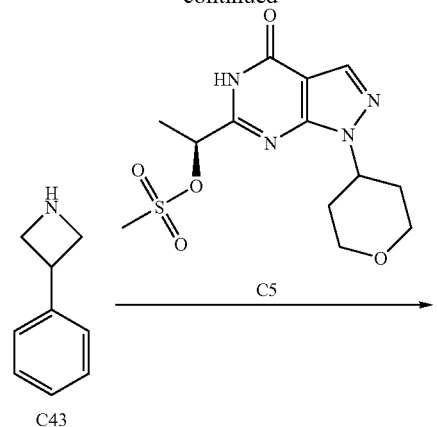

Step 1. Preparation of 3-phenylazetidine (C43). Compound C43 was prepared according to the general procedure for the synthesis of C40 in Example 9, except that 1-(diphenylmethyl)-3-phenylazetidine (See M. C. Hillier & C-y. Chen, *J. Organic Chem.* 2006, 71, 7885-7887) was used instead of 1-(diphenylmethyl)-3-(4-fluorophenoxy)azetidine, and the silica gel chromatography was carried out with 100:5:1 chloroform: MeOH: concentrated aqueous ammonium hydroxide as eluant. Yield: 427 mg (contains some impurities), <3.21 mmol, <19%. LCMS m/z 134.0 (M+1). $^1$H NMR (400 MHz, CD$_3$OD), product peaks only: δ 4.02 (m, 2H), 4.11 (m, 3H), 7.29 (m, 5H).

Step 2. Synthesis of title compound 11. Compound 11 was prepared according to the general procedure for the synthesis of 1 in Example 1, except that C43 was used in place of C9, and the chromatographic purification was carried out with 200:1 chloroform: MeOH as eluant. Yield: 485 mg, 1.28 mmol, 67%. Enantiomeric excess: 89.5%. LCMS m/z 380.2 (M+1). $^1$H NMR (400 MHz, CDCl$_3$) δ 1.34 (d, J=6.6 Hz, 3H), 1.92 (br d, J=12.6 Hz, 2H), 2.39 (m, 2H), 3.25 (dd, J=5.6, 5.6 Hz, 1H), 3.38 (dd, J=5.8, 5.8 Hz, 1H), 3.51 (q, J=6.7 Hz, 1H), 3.62 (m, 2H), 3.79 (m, 3H), 4.15 (br dd, J=11.5, 3.4 Hz, 2H), 4.84 (tt, J=11.6, 4.2 Hz, 1H), 7.23-7.37 (m, 5H), 8.07 (s, 1H), 9.87 (br s, 1H). $^{13}$C NMR (100 MHz, CDCl$_3$) δ 18.23, 32.17, 34.96, 53.72, 59.03, 60.24, 65.43, 67.01, 105.31, 126.80, 128.56, 134.74, 141.41, 151.83, 157.78, 160.56 (one aromatic signal not observed). This material was subjected to chiral chromatography (column: Chiralpak AD-H, 2.1×25 cm; Mobile phase: 85:15 carbon dioxide: MeOH; flow rate 65 g/min) to provide the pure enantiomer 11. Yield: 333 mg: Enantiomeric excess: 100%; LCMS and $^1$H NMR essentially unchanged.

EXAMPLE 12

6-[(1R)-1-(3-Pyrazin-2-ylazetidin-1-yl)ethyl]-1-(tetrahydro-2H-pyran-4-yl)-1,5-dihydro-4H-pyrazolo[3,4-d]pyrimidin-4-one

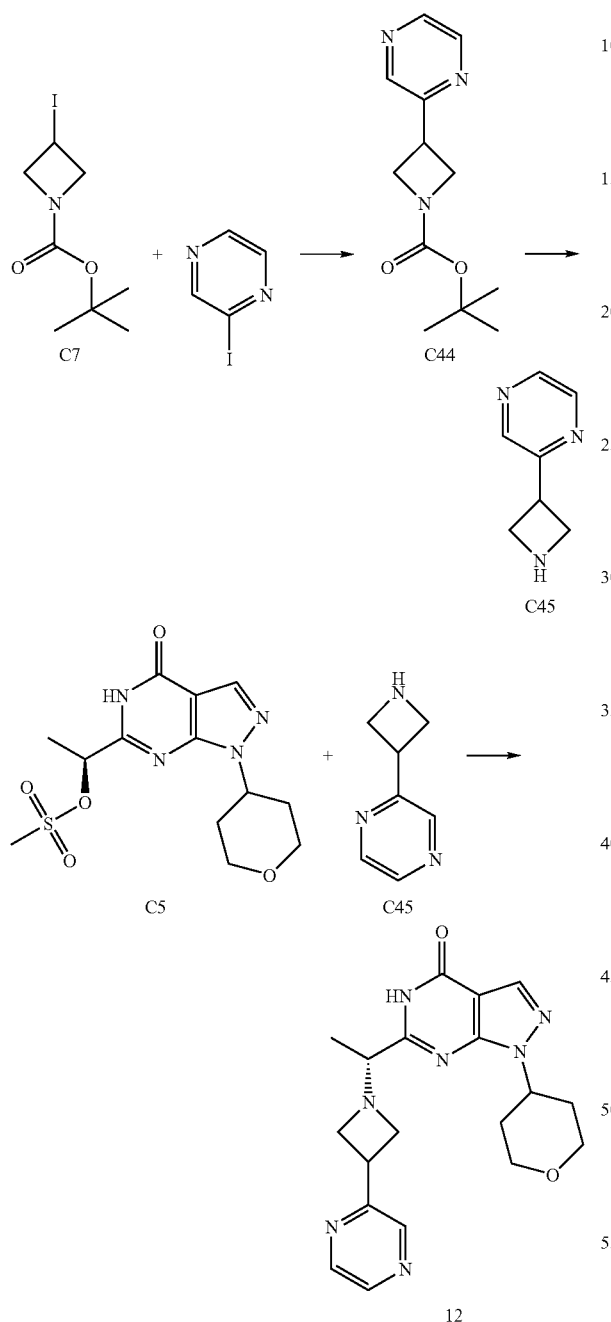

Step 1 Preparation of 2-azetidin-3-ylpyrazine (C45)

A. Preparation of tent-butyl 3-pyrazin-2-ylazetidine-1-carboxylate (C44). Compound C44 was prepared according to the general procedure for the synthesis of C8 in Example 1, except that 2-iodopyrazine was used in place of 2-bromo-4-methylpyridine. Yield: 360 mg, 1.53 mmol, 43%. LCMS m/z 236.2 (M+1). $^1$H NMR (400 MHz, CDCl$_3$) δ 1.46 (s, 9H), 3.91 (tt, J=8.7, 5.9 Hz, 1H), 4.18 (dd, J=8.5, 6.0 Hz, 2H), 4.32 (dd, J=8.7, 8.7 Hz, 2H), 8.47 (d, J=2.5 Hz, 1H), 8.50 (d, J=1.7 Hz, 1H), 8.60 (dd, J=2.5, 1.5 Hz, 1H). $^{13}$C NMR (100 MHz, CDCl$_3$) δ 28.35, 32.59, 54.55 (br), 79.63, 143.17, 143.70, 144.52, 156.30 (one downfield signal not observed).

B. Preparation of C45. Compound C45 was prepared according to the general procedure for the synthesis of C9 in Example 1, except that C44 was used instead of C8. Yield: 67.6 mg, 0.500 mmol, 100%. LCMS m/z 136.1 (M+1).

Step 2. Synthesis of title compound 12. Compound 12 was prepared according to the general procedure for the synthesis of 1 in Example 1, except that C45 was used in place of C9, and the chromatographic purification was carried out with 200:1, then 100:1 chloroform: MeOH as eluant. MS (APCI) m/z 382.2 (M+1). $^1$H NMR (400 MHz, CDCl$_3$) δ 1.35 (d, J=6.6 Hz, 3H), 1.90 (br d, J=12.5 Hz, 2H), 2.36 (m, 2H), 3.50 (dd, J=7.0, 7.0 Hz, 1H), 3.56-3.67 (m, 4H), 3.81 (m, 2H), 3.93 (m, 1H), 4.13 (br dd, J=11.5, 3.6 Hz, 2H), 4.84 (tt, J=11.7, 4.2 Hz, 1H), 8.05 (s, 1H), 8.46 (d, J=2.5 Hz, 1H), 8.51 (d, J=1.7 Hz, 1H), 8.57 (dd, J=2.5, 1.7 Hz, 1H). $^{13}$C NMR (100 MHz, CDCl$_3$) δ 17.92, 32.15, 34.10, 53.73, 56.95, 58.35, 64.93, 66.98, 105.25, 134.69, 143.10, 143.93, 144.23, 151.79, 155.54, 157.98, 160.19.

EXAMPLE 13

1-Cyclopentyl-6-{(1R)-1-[3-(pyrimidin-2-yloxy)azetidin-1-yl]ethyl}-1,5-dihydro-4H-pyrazolo[3,4-d]pyrimidin-4-one

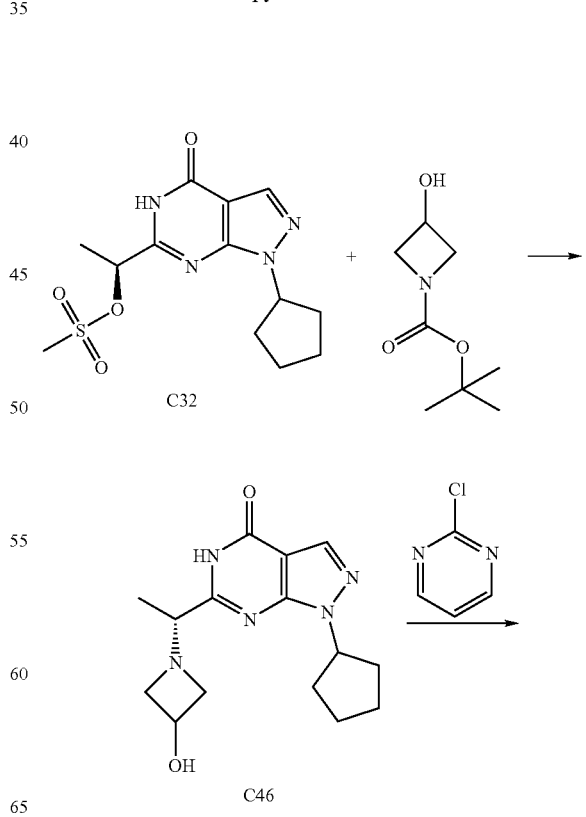

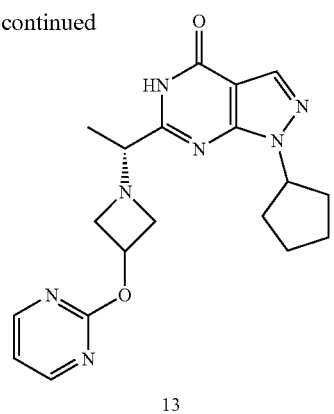

13

Step 1. Preparation of 1-cyclopentyl-6-[(1R)-1-(3-hydroxyazetidin-1-yl)ethyl]-1,5-dihydro-4H-pyrazolo[3,4-d]pyrimidin-4-one (C46). Compound C46 was prepared according to the general procedure for the synthesis of C19 in Example 3, except that C32 was used in place of C18. Yield: 2.0 g, 6.6 mmol, 69%. MS (APCI) m/z 302.0 (M−1). $^1$H NMR (400 MHz, CDCl$_3$) δ 1.33 (d, J=6.6 Hz, 3H), 1.71 (m, 2H), 1.97 (m, 2H), 2.10 (m, 4H), 3.18 (m, 1H), 3.28 (m, 1H), 3.51-3.65 (m, 3H), 4.44 (m, 1H), 5.17 (m, 1H), 8.09 (s, 1H). $^{13}$C NMR (100 MHz, CDCl$_3$) δ 18.25, 24.69, 32.41, 57.75, 61.87, 62.15, 62.57, 64.63, 104.92, 134.62, 152.11, 159.04, 160.41.

Step 2. Synthesis of title compound 13. Compound 13 was prepared according to the general procedure for the synthesis of 3 in Example 3, except that C46 was used instead of C19. Yield: 130 mg, 0.34 mmol, 21%. LCMS m/z 382.3 (M+1). $^1$H NMR (400 MHz, CDCl$_3$) δ 1.34 (d, J=6.6 Hz, 3H), 1.70 (m, 2H), 1.94 (m, 2H), 2.08 (m, 4H), 3.25 (br s, 1H), 3.42 (br s, 1H), 3.56 (br s, 1H), 3.92 (br s, 2H), 5.15 (m, 1H), 5.27 (m, 1H), 6.96 (t, J=4.8 Hz, 1H), 8.03 (s, 1H), 8.49 (d, J=4.8 Hz, 2H), 9.89 (br s, 1H). $^{13}$C NMR (100 MHz, CDCl$_3$) δ 18.02, 24.68, 32.36, 57.71, 58.44, 60.22, 65.14 (br), 65.31, 105.02, 115.58, 134.51, 151.93, 157.89, 159.38, 163.99 (one aromatic signal not observed).

This material (85% ee) was subjected to chromatography using a Chiralpak AS-H column (Eluant: 90:10 carbon dioxide: MeOH), followed by silica gel chromatographic purification (Eluant: 100:1 chloroform: MeOH) to provide the pure enantiomer 13. Yield: 68 mg. LCMS m/z 382.3 (M+1). $^1$H NMR (400 MHz, CDCl$_3$) δ 1.37 (br s, 3H), 1.72 (m, 2H), 1.96 (m, 2H), 2.10 (m, 4H), 3.30 (br s, 1H), 3.47 (br s, 1H), 3.60 (br s, 1H), 3.96 (br s, 2H), 5.16 (m, 1H), 5.29 (m, 1H), 6.98 (t, J=4.8 Hz, 1H), 8.05 (s, 1H), 8.50 (d, J=4.8 Hz, 2H), 9.87 (br s, 1H).

ADDITIONAL EXAMPLES

Side chains used in the synthesis of the compounds of Examples 14-87 (as shown in Table 2 below) that were not commercially available were prepared according to the following methods:

Preparation 1

Preparation of 3-(4-trifluoromethylphenoxy)azetidine

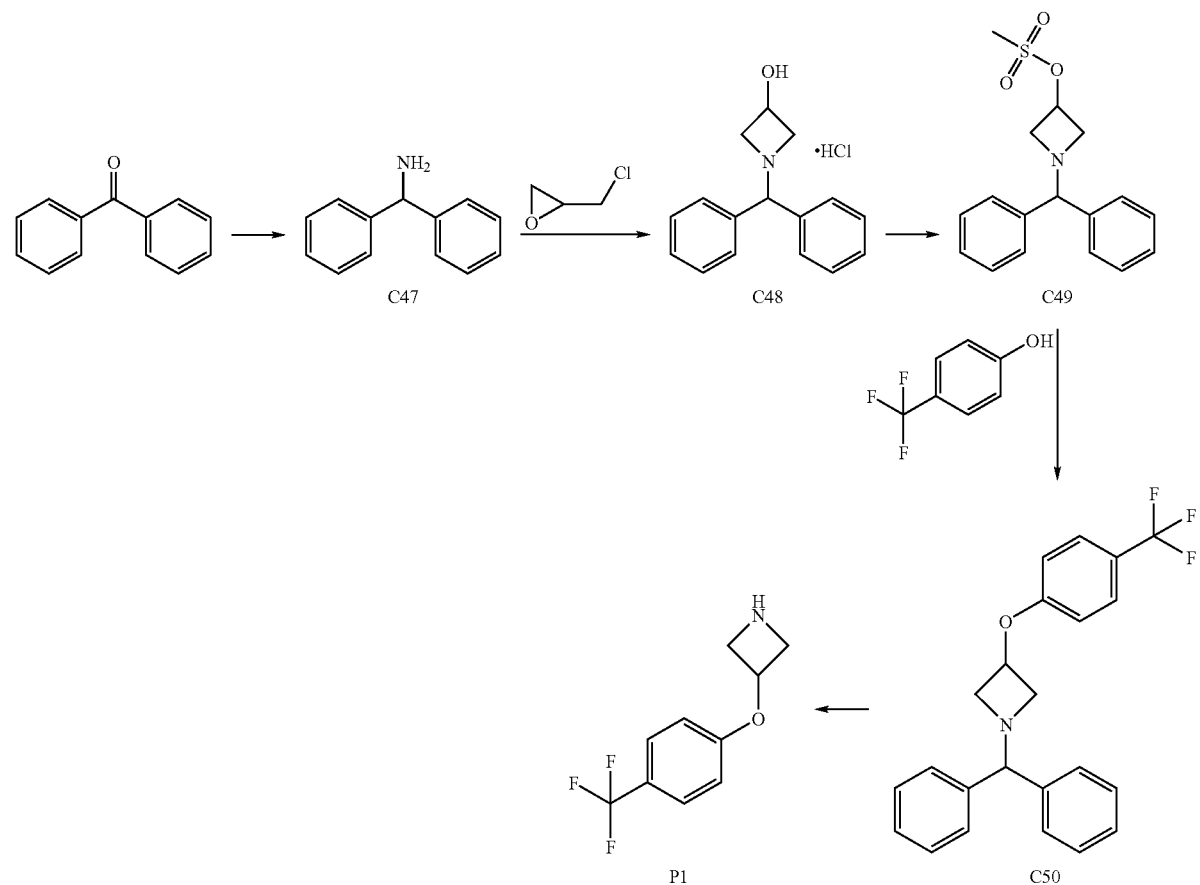

A. Preparation of 1,1-diphenylethanamine (C47). A mixture of benzophenone (250 g, 1.37 mol), formamide (250 mL) and 85% formic acid (31.5 mL) was heated to 190° C. for 3 h. The reaction mixture was cooled to 140° C. and poured into cold water (1.2 L). The resulting precipitate was collected by filtration, to which was added concentrated aqueous hydrochloric acid (600 mL), and the reaction mixture was heated at reflux under vigorous stirring. The hydrochloride salt was collected by filtration and washed with water, then with diethyl ether. The white crystals were treated with a 2.5N aqueous solution of sodium hydroxide and extracted with diethyl ether. The combined organic layers were dried over anhydrous sodium sulfate, filtered, and concentrated in vacuo. The crude product was distilled under reduced pressure to afford C47 as a colorless oil. Yield: 227.5 g, 1.24 mol, 90%.

B. Preparation of 1-(diphenylmethyl)azetidin-3-ol hydrochloride (C48). A solution of 2-(chloromethyl)oxirane (260 g, 2.81 mol) and C47 (500 g, 2.73 mol) in MeOH (1 L) was heated at reflux for 4 days. Solvent was removed under reduced pressure to provide a white precipitate, which was collected by filtration. The solid was washed with acetone and dried to provide C48, which was used in the next step without further purification.

C. Preparation of 1-(diphenylmethyl)azetidin-3-yl methanesulfonate (C49). Methanesulfonyl chloride (180 g, 1.57 mol) was added to a solution of C48 (360 g, 1.31 mol) and triethylamine (330 g, 3.26 mol) in dichloromethane (3 L) at 0° C. The reaction mixture was stirred at room temperature for 3 h, quenched with saturated aqueous sodium bicarbonate solution, then extracted with dichloromethane. The combined organic layers were dried over anhydrous sodium sulfate, filtered and concentrated in vacuo to afford C49. Yield: 360 g, 1.14 mol, 87%.

D. Preparation of 1-(diphenylmethyl)-3-[4-(trifluoromethyl)phenoxy]azetidine (C50). To a solution of C49 (317 g, 1.0 mol) in acetonitrile (1.5 L) were added 4-(trifluoromethyl)phenol (194.4 g, 1.2 mol) and potassium carbonate (165.6 g, 1.2 mol). The reaction mixture was heated at reflux for about 20 h, then the mixture was filtered and concentrated in vacuo. Dichloromethane (800 mL) was added, the organic phase was washed with water, filtered and concentrated in vacuo. The residue was purified by silica gel chromatography (Eluant: 5:1 hexane: diethyl ether) to provide C50. Yield: 373 g, 0.97 mol, 97%.

E. Preparation of compound P1. To a solution of C50 (191 g, 0.50 mol) in MeOH (2 L) was added 10% palladium hydroxide on carbon (9.6 g), and the suspension was hydrogenated at 45 psi at 60° C. for about 18 h. The reaction mixture was filtered and the filtrate was concentrated to afford P1, which was used in the next step without further purification. Yield: 86.6 g, 0.40 mol, 80%. LCMS m/z 218.1 (M+1). $^1$H NMR (400 MHz, CDCl$_3$) δ 3.85 (m, 2H), 3.96 (m, 2H), 4.99 (m, 1H), 6.77 (d, 2H), 7.50 (m, 2H).

Preparation 2

Preparation of 3-(3-chlorophenoxy)azetidine

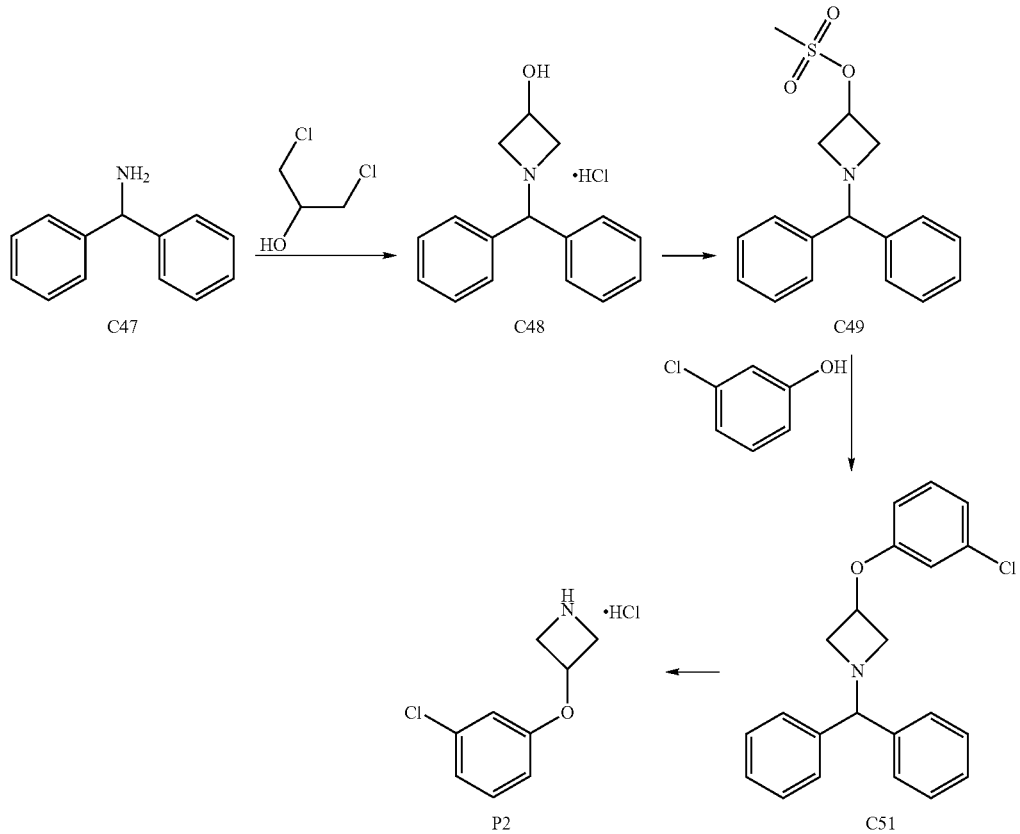

A. Preparation of 1-(diphenylmethyl)azetidin-3-ol hydrochloride (C48).

Compound C48 was prepared according to the procedure described in Preparation 1, except that 1,3-dichloropropan-2-ol was used in place of 2-(chloromethyl)oxirane. Yield: 4321 g, 15.7 mol, 48%.

B. Preparation of 1-(diphenylmethyl)azetidin-3-yl methanesulfonate (C49). Compound C49 was prepared according to the procedure described in Preparation 1 to afford C49 as a yellow solid. Yield: 303 g, 0.96 mol, 91%. $^1$H NMR (400 MHz, CDCl$_3$) δ 2.91 (s, 3H), 3.13 (m, 2H), 3.55 (m, 2H), 4.31 (s, 1H), 4.02 (m, 1H), 7.14 (m, 2H), 7.20 (m, 4H), 7.31 (m, 4H).

C. Preparation of 3-(3-chlorophenoxy)-1-(diphenylmethyl)azetidine (C51). To a stirred suspension of sodium hydride (60%, dispersed in oil, 25.2 g, 0.63 mol) in DMF (1.5 L) was added 3-chlorophenol (70.88 g, 0.63 mol) at 0° C. After completion of the addition, the reaction mixture was stirred for 1 h, then C49 (200 g, 0.63 mol) was added in one portion. The reaction was heated at reflux for 3 h, diluted with water and extracted with EtOAc (3×1 L). The combined organic layers were dried over anhydrous sodium sulfate and concentrated in vacuo. The residue was purified by silica gel chromatography (Eluant: petroleum ether) to afford C51 as a light yellow solid. Yield: 123 g, 0.35 mol, 51%.

D. Preparation of compound P2. To a solution of C51 (200 g, 0.569 mol) in dichloromethane (2 L) was added drop-wise 2-chloroethyl chloroformate (75 mL, 0.726 mol) at room temperature. After completion of the addition, the reaction mixture was stirred for 4 h, and concentrated to dryness. The residue was dissolved in MeOH (2 L) and the reaction mixture was heated at reflux for 3 h. The mixture was concentrated in vacuo and diethyl ether (500 mL) was added; the resulting precipitate was filtered to give P2 as a white solid. Yield: 60 g, 0.27 mol, 44.5%. LCMS m/z 184.4 (M+1). $^1$H NMR (400 MHz, DMSO-d$_6$) δ 3.95 (m, 2H), 4.43 (m, 2H), 5.15 (m, 1H), 6.85 (m, 1H), 6.97 (s, 1H), 7.08 (m, 1H), 7.32 (m, 1H), 9.58 (br s, 2H).

Preparation 3

Preparation of 3-(3-fluorophenoxy)azetidine

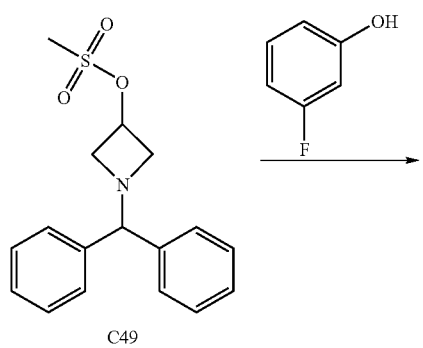

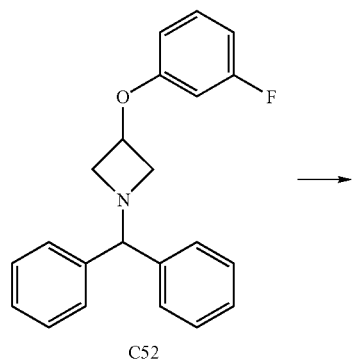

C52

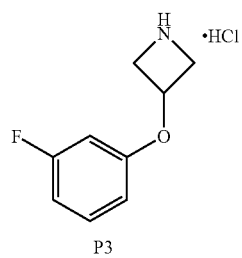

P3

A. Preparation of 3-(3-fluorophenoxy)-1-(diphenylmethyl)azetidine (C52). Compound C52 was prepared according to the procedure described for the synthesis of C51 in Preparation 2, except that 3-fluorophenol was used in place of 3-chlorophenol. Yield: 9.5 g, 28.5 mmol, 85%. This material was used in the next step without additional purification.

B. Preparation of compound P3. To a stirred solution of C52 (5 g, 15 mmol) in ethanol (50 mL) was added ammonium formate (4.2 g, 75 mmol) followed by addition of 10% palladium on carbon (1 g) and the resulting suspension was heated at reflux for 6 h. Catalyst was then removed by filtration through Celite and the solids were washed with EtOH. The combined filtrates were concentrated in vacuo to provide a residue, which was purified by silica gel chromatography (Eluant: EtOAc:hexane) to afford P3 as its free base. This was converted to the hydrochloride salt by stirring in ethanolic hydrochloric acid at 0° C. After 1 h, the solvent was removed under reduced pressure, and the residue obtained was stirred and washed with diethyl ether to afford P3 as an off-white solid. Yield: 1.5 g, 9.0 mmol, 50%. M.P. 104-106° C. MS m/z 168 (M+1). $^1$H NMR (400 MHz, DMSO-d$_6$) δ 3.94 (br s, 2H), 4.42 (br s, 2H), 5.05-5.11 (m, 1H), 6.71-6.74 (dd, J=2.2, 2.2 Hz, 1H), 6.76-6.80 (m, 1H), 6.82-6.87 (m, 1H), 7.32-7.37 (m, 1H), 9.61 (br s, 2H).

Preparation 4

Preparation of 2-azetidin-3-ylpyridine dihydrochloride

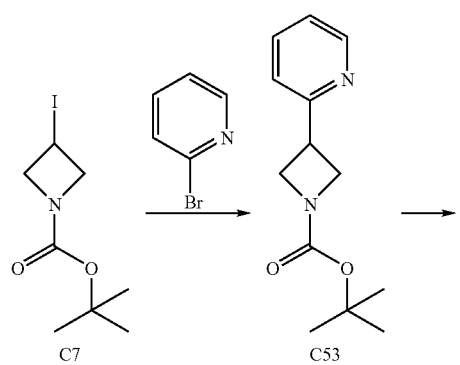

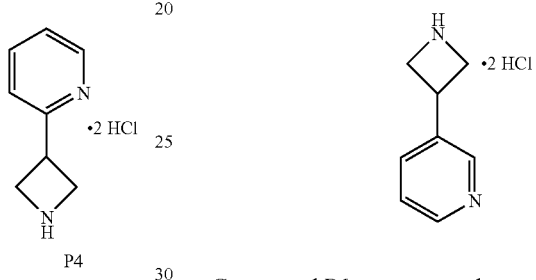

A. Preparation of tert-butyl 3-pyridin-2-ylazetidine-1-carboxylate (C53). Compound C53 was prepared according to the procedure described for the preparation of C8 in Example 1, except that 2-bromopyridine was used in place of 2-bromo-4-methylpyridine. Yield: 15.7 g, 67 mmol, 67%. $^1$H NMR (400 MHz, DMSO-$d_6$) δ 1.40 (s, 9H), 3.87-4.04 (m, 3H), 4.15-4.19 (m, 2H), 7.25-7.32 (m, 2H), 7.74 (dd, J=6, 6 Hz, 1H), 8.59 (d, J=4 Hz, 1H).

B. Preparation of compound P4. A solution of hydrochloric acid in dioxane (4M, 67 mL, 0.27 mol) was added to a solution of C53 (15.7 g, 67 mmol) in MeOH (600 mL). The reaction mixture was stirred for 1 h at 40-50° C. and then concentrated in vacuo. The residue was recrystallized from MeOH to afford P4. Yield: 11.2 g, 54.1 mmol, 80%. MS (APCI) m/z 135.1 (M+1). $^1$H NMR (400 MHz, DMSO-$d_6$) δ 4.26-4.31 (m, 4H), 4.48-4.57 (m, 1H), 7.77 (dd, J=7.1, 7.1 Hz, 1H), 8.06 (d, J=7.1 Hz, 1H), 8.36 (dd, 1H, J=7, 7.1 Hz), 8.76 (d, J=7 Hz, 1H), 9.57 (s, 1H), 9.89 (s, 1H).

Preparation 5

Preparation of 4-azetidin-3-ylpyridine dihydrochloride

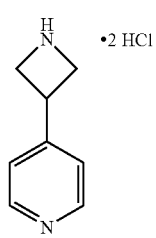

P5

Compound P5 was prepared according to the general procedure described for the synthesis of P4 in Preparation 4. The resulting precipitate was filtered off and recrystallized from a MeOH/THF mixture to provide the dihydrochloride P5. Yield: 6.6 g, 31.9 mmol, 68%. MS (APCI) m/z 135.1 (M+1). $^1$H NMR (400 MHz, DMSO-$d_6$) δ 4.1-4.2 (m, 2H), 4.27-4.45 (m, 3H), 8.1 (d, J=6.6 Hz, 2H), 8.91 (d, J=6 Hz, 2H), 9.66 (br s, 1H), 9.82 (br s, 1H).

Preparation 6

Preparation of 3-azetidin-3-ylpyridine dihydrochloride

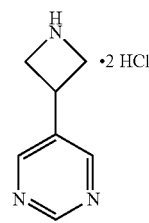

P6

Compound P6 was prepared according to the general procedures described for the synthesis of P4 in Preparation 4, to provide the dihydrochloride P6. Yield: 8 g, 38.6 mmol, 53%. MS (APCI) m/z 135.1 (M+1). NMR (400 MHz, DMSO-$d_6$) δ 4.13-4.22 (m, 2H), 4.26-4.36 (m, 3H), 8.00 (dd, J=6.1, 6.1 Hz, 1H), 8.65 (d, J=6.1 Hz, 1H), 8.81 (d, J=6.1 Hz, 1H), 9.01 (s, 1H), 9.52 (br s, 1H), 9.74 (br s, 1H).

Preparation 7

Preparation of 5-azetidin-3-ylpyrimidine dihydrochloride

P7

Compound P7 was prepared according to the general procedures described for the synthesis of P4 in Preparation 4, to provide the dihydrochloride P7. Yield: 5.2 g, 25 mmol, 39%. $^1$H NMR: (400 MHz, DMSO-$d_6$) δ 4.15-4.22 (m, 3H), 4.24-4.30 (m, 2H), 9.02 (s, 2H), 9.17 (s, 1H), 9.41-9.57 (s, 1H), 9.59-9.75 (s, 1H).

Preparation 8

Preparation of 3-azetidin-3-ylpyridazine dihydrochloride

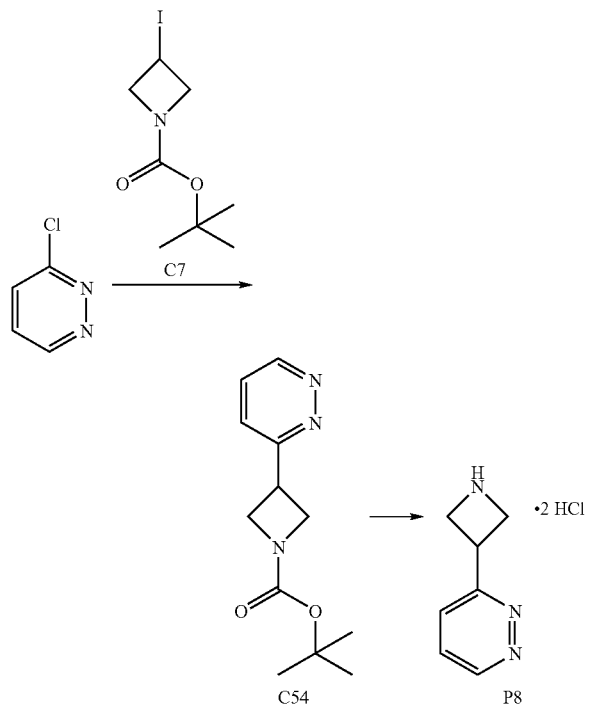

A. Preparation of tert-butyl 3-pyridazine-3-ylazetidine-1-carboxylate (C54). Compound C54 was prepared according to the procedure described in the synthesis of C8 in Example 1, except that 3-chloropyridazine was used in place of 2-bromo-4-methylpyridine. Yield: 5 g, 18.5 mmol, 10%. 4.22 (m, 2H), 4.26-4.36 (m, 3H), 8.00 (dd, J=6, 6 Hz, 1H), 8.65 (d, J=6 Hz, 1H), 8.81 (d, J=6 Hz, 1H), 9.01 (s, 1H), 9.52 (br s, 1H), 9.74 (br s, 1H).

B. Preparation of compound P8. Compound P8 was prepared according to the procedure described in the preparation of P4, except that C54 was used instead of C53. Yield: 3.7 g, 15.3 mmol, 54%. $^1$H NMR (400 MHz, DMSO-d$_6$) δ 4.13-

Preparation 9

Preparation of 4-azetidin-3-ylpyrimidine tris(trifluoroacetate)

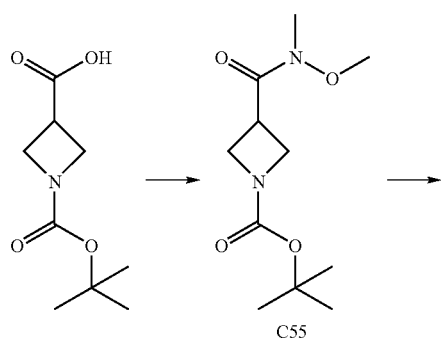

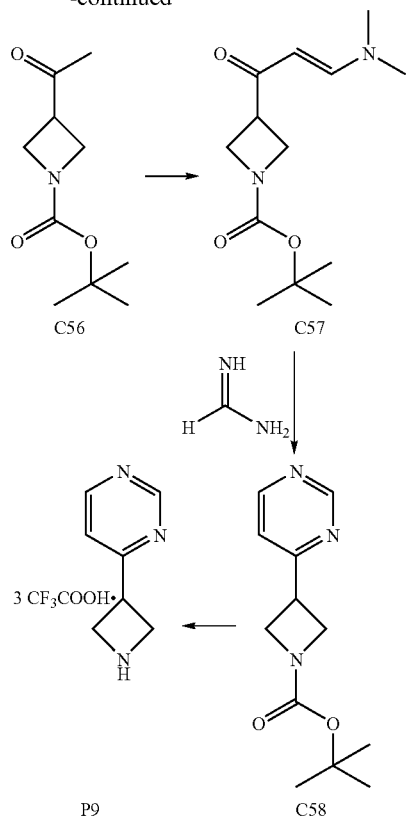

A. Preparation of tert-butyl 3-{[methoxy(methyl)amino]carbonyl}azetidine-1-carboxylate (C55). To a solution of 1-(tert-butoxycarbonyl)azetidine-3-carboxylic acid (22.3 g, 0.111 mol) in THF (250 mL), 1,3-dicyclohexylcarbodiimide (24.4 g, 0.150 mol) was added portion-wise. The reaction mixture was stirred at room temperature for 1.5 h before addition of a suspension of N,O-dimethylhydroxylamine hydrochloride (15.0 g, 0.154 mol) in a mixture of acetonitrile (300 mL) and triethylamine (22.6 mL, 0.162 mol). The resulting mixture was stirred at room temperature for 24 h, and then the reaction was concentrated in vacuo. The residue was taken up in water (300 mL) and EtOAc (800 mL), the organic layer was separated, washed with a 5% aqueous citric acid solution (2×200 mL), water (2×150 mL), and saturated aqueous sodium chloride solution (2×150 mL), and then dried over magnesium sulfate. Filtration and removal of solvent gave C55 as a light yellow oil. Yield: 28.15 g, 0.12 mol, 100%. $^1$H NMR (400 MHz, CDCl$_3$) δ 4.12-4.09 (m, 2H), 4.03-3.99 (m, 2H), 3.64-3.56 (m, 1H), 3.63 (s, 3H), 3.17 (s, 3H), 1.40 (s, 9H).

B. Preparation of tert-butyl 3-acetylazetidine-1-carboxylate (C56). A solution of C55 (27.1 g, 0.111 mol) in THF (200 mL) was added drop-wise to a 1.4M solution of methylmagnesium bromide in a mixture of THF and toluene (25:75) (99.0 mL, 0.139 mol) over 40 mins, while the reaction temp was kept at about 0° C. After completion of the addition, the mixture was stirred at 10-15° C. for 2 hours, followed by 1 h at room temp. The reaction mixture was cooled to 0° C. and quenched with a 10% aqueous citric acid solution (150 mL). The organic layer was separated, and the aqueous layer was extracted with EtOAc (2×300 mL). The combined organic layers were washed with saturated aqueous sodium chloride solution (2×250 mL), and dried over sodium sulfate. Filtration and removal of solvent gave a residue, which was purified by silica gel chromatography (Eluant: chloroform) to afford C56. Yield: 20.6 g, 0.10 mol, 93%. $^1$H NMR (400 MHz, CDCl$_3$): δ 4.04-4.02 (m, 4H), 3.43-3.35 (m, 1H), 2.16 (s, 3H), 1.42 (s, 9H).

C. Preparation of t-butyl 3-[(2E)-3-(dimethylamino)prop-2-enoyl]azetidine-1-carboxylate (C57). A solution of C56 (20.6 g, 0.103 mol) in DMF dimethyl acetal was heated at reflux for 45 h. The reaction mixture was evaporated and azeotroped with toluene (2×200 mL) to afford C57, which was used in the next step without additional purification. Yield: 28.0 g, 0.11 mol, >100%.

D. Preparation of tert-butyl 3-pyrimidin-4-ylazetidine-1-carboxylate (C58). Formamidine hydrochloride (4.96 g, 0.062 mol) and a solution of C57 in MeOH (75 mL) were added in sequence to a solution of sodium methoxide (3.33 g, 0.062 mol) in MeOH (75 mL). The reaction mixture was heated at reflux for 50 h, the solvent was exchanged for dioxane and the mixture was heated at reflux for another 40 h. At that point, the solvent was removed in vacuo, and the residue treated with water (150 mL) and EtOAc (250 mL). The organic layer was separated and the aqueous layer was extracted with EtOAc (2×250 mL). The combined organic layers were dried over magnesium sulfate, filtered and concentrated in vacuo. The residue was purified by silica gel chromatography (Eluant: EtOAc) to afford C58. Yield: 2.0 g, 8.5 mmol, 21%. $^1$H NMR (400 MHz, DMSO-d$_6$) δ 9.18 (d, J=1.2 Hz, 1H), 8.73 (d, J=5.1 Hz, 1H), 7.48 (dd, J=5.1, 1.2 Hz, 1H), 4.21-4.17 (m, 2H), 4.02-3.98 (m, 2H), 3.96-3.88 (m, 1H), 1.39 (s, 9H).

E. Preparation of compound P9. Trifluoroacetic acid (9.9 mL, 14.7 g, 0.13 mol) was added to a 0-5° C. solution of C58 (1.9 g, 8 mmol) in dichloromethane (10 mL). The reaction mixture was stirred under cooling for 30 mins followed by 1 h at room temperature. The solvent was removed under reduced pressure and the resulting residue was azeotroped with dichloromethane (5×50 mL), and MeOH (5×50 mL) to afford P9 as a brown syrup. Yield: 2.42 g, 7.9 mmol, 99%. $^1$H NMR (400 MHz, DMSO-d$_6$) δ 9.33 (br s, 1H), 9.00 (br s, 1H), 9.24 (d, J=1.2 Hz, 1H), 8.78 (d, J=5.1 Hz, 1H), 7.52 (dd, J=5.1, 1.2 Hz, 1H), 4.33-4.19 (m, 5H).

Preparation 10

Preparation of 4-azetidin-3-yl-2-methylpyrimidine tris(trifluoroacetate)

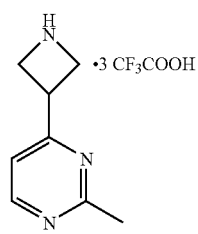

P10

Compound P10 was prepared according to the general procedures described in Preparation 9, to provide P10 as a white solid. Yield: 20.8 g, 42.2 mmol, 96%. $^1$H NMR (400 MHz, DMSO-d$_6$) δ 15.29 (br s, 2H), 9.15 (br s, 1H), 8.83 (br s, 1H), 8.66 (d, J=5.1 Hz, 1H), 7.31 (d, J=5.1 Hz, 1H), 4.29-4.15 (m, 5H), 2.65 (s, 3H).

Preparation 11

Preparation of 2-[(3S)-pyrrolidin-3-yloxy]pyrimidine trifluoroacetate

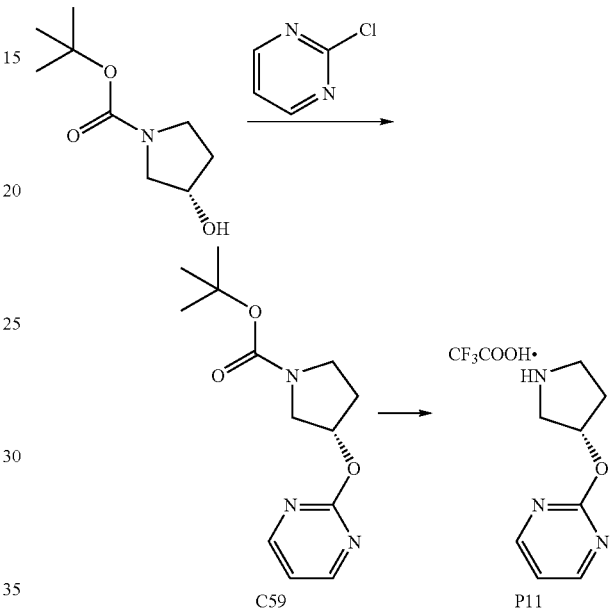

A. Preparation of tert-butyl (3S)-3-(pyrimidin-2-yloxy) pyrrolidine-1-carboxylate (C59). To a solution of tert-butyl (3S)-3-hydroxypyrrolidine-1-carboxylate (990 mg, 5.29 mmol) in THF (10 mL) was slowly added potassium tert-butoxide (593 mg, 5.29 mmol). The reaction mixture was stirred for 30 mins, and then 2-chloropyrimidine (606 mg, 5.29 mmol) was added. The mixture was stirred at room temperature and monitored by thin layer chromatography. The solvent was removed under reduced pressure, and the residue was treated with EtOAc and a saturated aqueous solution of sodium bicarbonate. The organic layer was separated and the aqueous layer was extracted with EtOAc. The combined organic layers were dried over magnesium sulfate, filtered and concentrated in vacuo. The residue was purified by silica gel chromatography (Gradient: 0% to 100% EtOAc in hexane) to afford C59. Yield: 1.29 g, 4.9 mmol, 92%. LCMS m/z 266.3 (M+1). $^1$H NMR (400 MHz, CDCl$_3$) δ 1.43 (s, 9H), 2.10-2.25 (m, 2H), 3.50-3.64 (m, 4H), 5.51 (m, 1H), 6.93 (m, 1H), 8.50 (m, 2H).

B. Preparation of compound P11. A mixture of C59 (1.29 g, 4.85 mmol) and trifluoroacetic acid (5 mL) in dichloroethane (15 mL) was stirred at room temp for 4 hours. The solvent was removed in vacuo and the product was dried on high vacuum to give the trifluoroacetate salt P11, which was used in the next step without additional purification. LCMS m/z 166.2 (M+1). The (R)-enantiomer of P11 can be prepared in the same way, using tert-butyl (3R)-3-hydroxypyrrolidine-1-carboxylate as starting material.

Preparation 12

Preparation of 2-azetidin-3-yl-5-methylpyrimidine dihydrochloride

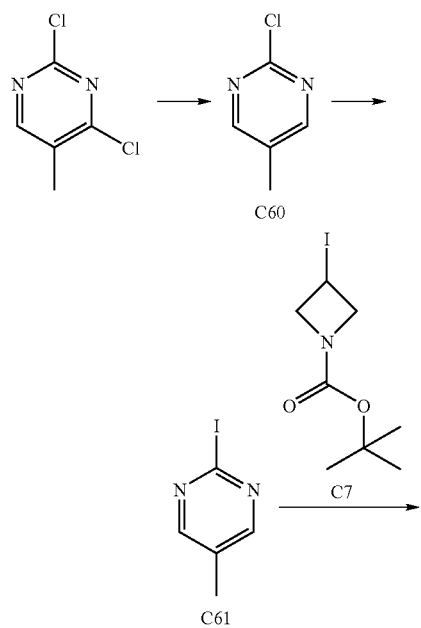

A. Preparation of 2-chloro-5-methylpyrimidine (C60). A mixture of 2,4-dichloro-5-methylpyrimidine (50 g, 0.31 mol), water (500 mL) and zinc dust (50 g, 0.94 mol) was heated at reflux overnight. The reaction mixture was filtered and the filtrate was extracted with dichloromethane (3×500 mL). The organic layer was washed with saturated aqueous sodium chloride solution, dried over sodium sulfate, filtered, and concentrated in vacuo. The residue was recrystallized from petroleum ether to afford compound C60 as a white solid. Yield: 27.9 g, 0.22 mol, 75%. LCMS m/z 129.3 (M+1). $^1$H NMR (400 MHz, CDCl$_3$) δ 2.25 (s, 3H), 8.40 (5, 2H).

B. Preparation of 2-iodo-5-methylpyrimidine (C61). Hydroiodic acid (13 mL), cooled to 0° C., was added to C60 (2.0 g, 15.6 mmol) and the reaction mixture was stirred at 0° C. for 1 h. The mixture was neutralized with a saturated aqueous solution of sodium bicarbonate and treated with sodium thiosulfate. The aqueous layer was extracted with EtOAc, dried over magnesium sulfate, filtered and concentrated in vacuo. The residue was purified by silica gel chromatography (Gradient: 0% to 100% EtOAc in heptane) to afford C61 as a white powder. Yield: 1.54 g, 6.99 mmol, 45%. $^1$H NMR (400 MHz, CDCl$_3$) δ 2.24 (s, 3H), 8.29 (s, 2H).

C. Preparation of tert-butyl 3-(5-methylpyrimidin-2-yl)azetidine-1-carboxylate (C62). Compound C62 was prepared according to the procedure described for the synthesis of C8 in Example 1, except that 2-iodo-5-methylpyrimidine C61 was used in place of 2-bromo-4-methylpyridine. Yield: 1.01 g, 4.05 mmol, 81%. $^1$H NMR (400 MHz, CDCl$_3$) δ 1.44 (s, 9H), 2.37 (s, 3H), 4.25 (m, 3H), 4.33 (m, 2H), 8.78 (s, 2H).

D. Preparation of compound P12. To a solution of C62 (469 mg, 1.88 mmol) in propan-2-ol was added a solution of hydrochloric acid in propan-2-ol (1N, 0.376 mL, 3.76 mmol) and the reaction mixture was stirred at room temperature for 18 h. The mixture was concentrated, the residue was diluted with dichloromethane and treated with an aqueous solution of sodium hydroxide (6N, 0.625 mL, 3.76 mmol). The organic layer was decanted, dried over magnesium sulfate, filtered and concentrated in vacuo. The resulting solid was triturated with a mixture of dichloromethane (1 mL) and diethyl ether (10 mL), filtered and washed with diethyl ether to afford P12. Yield: 203 mg, 1.36 mmol, 72%. $^1$H NMR (400 MHz, CDCl$_3$) δ 2.34 (s, 3H), 4.18-4.23 (m, 5H), 8.66 (s, 2H).

Preparation 13

Preparation of 2-(azetidin-3-ylmethyl)pyrimidine

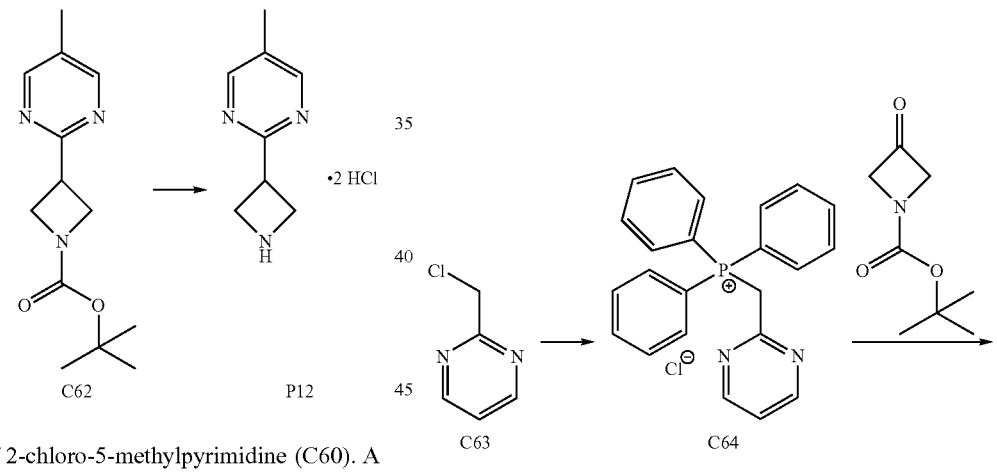

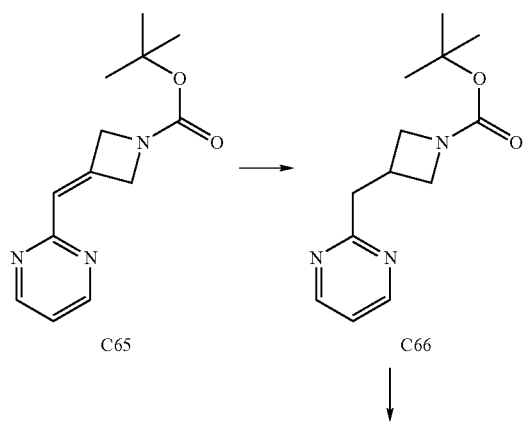

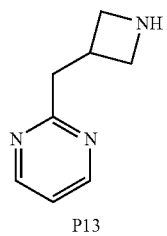

P13

A. Preparation of 2-(chloromethyl)pyrimidine (C63) is described by M. G. N. Russel & R. W. Caning, *J. Med. Chem.*, 2005, 48, 1367-1383 and by Y. Todoroki & M. Sawada, *Bioorganic & Med. Chem.*, 2004, 13, 363-386.

B. Preparation of triphenyl(pyrimidin-2-ylmethyl)phosphonium chloride (C64). To a solution of C63 (8 g, 48.5 mol) in benzene (80 mL) was added triphenylphosphine (12.7 g, 48.5 mol) and the mixture was heated at reflux for about 24 h. After the reaction mixture cooled to room temperature, the resulting solid was filtered and washed with benzene (80 mL). The filtrate was concentrated in vacuo to afford C64. Yield: 17.1 g, 48.2 mol, 99%. LCMS (ES+) m/z 355.2 (M+).

C. Preparation of tert-butyl 3-(pyrimidin-2-ylmethylene)azetidine-1-carboxylate (C65). A mixture of C64 (900 mg, 2.3 mmol) and sodium t-butoxide (221 mg, 2.3 mmol) in dimethyl sulfoxide (20 mL) was stirred at room temperature for 1 h before tert-butyl 3-oxoazetidine-1-carboxylate (473 mg, 2.76 mmol) was added. The reaction mixture was stirred for about 18 h, diluted with dichloromethane (50 mL) and treated with water (25 mL). The mixture was stirred for 10 mins, and the organic layer was decanted, dried over magnesium sulfate, filtered and concentrated. The residue was pre-adsorbed on silica gel and purified by chromatography to afford C65. Yield: 460 mg, 1.86 mmol, 80%. LCMS (ES+) m/z 248.3 (M+1). $^1$H NMR (400 MHz, CDCl$_3$) δ 1.46 (s, 9H), 4.67 (s, 2H), 4.94 (m, 2H), 6.44 (br s, 1H), 7.03 (t, J=4.9 Hz, 1H), 8.65 (d, J=5.0 Hz, 2H).

D Preparation of tert-butyl 3-(pyrimidin-2-ylmethyl)azetidine-1-carboxylate (C66). To a mixture of piperidine (1.27 g, 14.9 mmol) and formic acid (1.59 mL, 14.9 mmol) in EtOH (50 mL) was added C65 (3.5 g, 14.2 mmol) and palladium (10% weight on carbon, 350 mg). The reaction mixture was heated to 78° C. for 5 h, filtered through a pad of Celite and concentrated in vacuo. The residue was pre-adsorbed on silica gel and purified by chromatography (Gradient: heptane: EtOAc) to afford C66. Yield: 3.23 g, 13.0 mmol, 92%. LCMS (ES+) m/z 250.4 (M+1). $^1$H NMR (400 MHz, CDCl$_3$) δ 1.41 (s, 9H), 3.09 (m, 1H), 3.24 (d, J=7.7 Hz, 2H), 3.72 (dd, J=8.8, 5.5 Hz, 2H), 4.07 (dd, J=8.5, 8.5 Hz, 2H), 7.13 (t, J=4.9 Hz, 1H), 8.63 (d, J=5 Hz, 2H).

E. Preparation of compound P13. P13 was prepared according to the procedure described for the synthesis of P11 in Preparation 11, except that C66 was used in place of C59. Compound P13 was used in the next step without additional purification.

Preparation 14

Preparation of 2-pyrrolidin-3-yl-pyrimidine

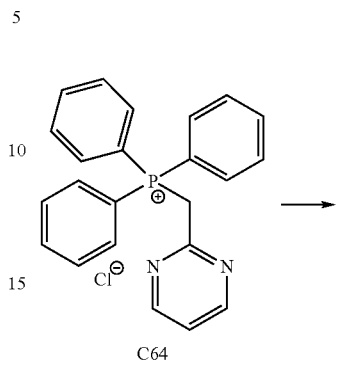

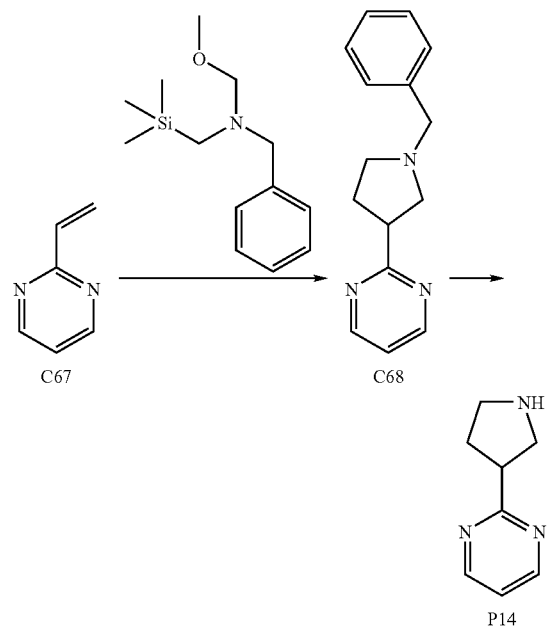

A. Preparation of 2-vinylpyrimidine (C67). Sodium tert-butoxide (1.22 g, 12.7 mmol) was added to a solution of C64 (4.5 g, 12.7 mmol) in THF (13 mL), and the reaction mixture was stirred at room temperature for 2 h. A solution of formaldehyde in water (37%, 2.8 mL, 38 mmol) was added and the mixture was stirred for an additional 18 h. The reaction mixture was pre-adsorbed on silica gel and purified twice by chromatography (Eluant: diethyl ether) to afford C67. Yield: 950 mg, 8.96 mmol, 71%. $^1$H NMR (400 MHz, CDCl$_3$) δ 5.72 (dd, J=10.6, 2.1 Hz, 1H), 6.60 (dd, J=17.4, 2.1 Hz, 1H), 6.86 (dd, J=17.4, 10.6 Hz, 1H), 7.11 (t, J=4.9 Hz, 1H), 8.68 (d, J=4.8 Hz, 2H).

B. Preparation of 2-(1-benzylpyrrolidin-3-yl)pyrimidine (C68). To a solution of C67 (888 mg, 8.37 mmol) in dichloromethane (8 mL) was added trifluoroacetic acid (0.19 mL, 2.51 mmol), followed by drop-wise addition of a solution of N-(methoxymethyl)-N-(trimethylsilylmethyl)benzylamine (2.58 g, 10.9 mmol) in dichloromethane (8 mL). The reaction mixture was stirred at room temperature for about 18 h. The reaction mixture was pre-adsorbed on silica gel and purified by chromatography (Gradient: dichloromethane: MeOH) to afford C68. Yield: 1.37 g, 5.73 mmol, 68%. LCMS (ES+) m/z 240.4 (M+1).

C. Preparation of 2-pyrrolidin-3-yl-pyrimidine (P14). To a mixture of ammonium formate (166 mg, 2.51 mmol) in MeOH (8 mL) was added a solution of C68 (600 mg, 2.51 mmol) in EtOH (2 mL) and palladium on carbon (10%, 60 mg). The reaction was heated to 60° C. for 46 h and then left for 24 h at room temperature. The reaction mixture was filtered through a pad of Celite, and the filtrate was pre-adsorbed on silica gel. Purification via silica gel chromatography (Gradient: heptane: EtOAc) gave P14. Yield: 120 mg, 0.80 mmol, 32%. This material was not pure, as assessed by $^1$H NMR, but was used without additional purification.

Preparation 15

Preparation of 2-azetidin-3-yl-4,6-dimethylpyrimidine

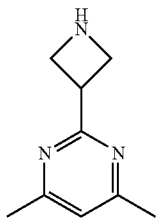

P15

Compound P15 was prepared according to the general procedure described for the synthesis of P12 in Preparation 12, except that 2-chloro-4,6-dimethylpyrimidine (the synthesis of 2-chloro-4,6-dimethylpyrimidine is described by G. Vlad & I. T. Horvath, *J. Organic Chem.*, 2002, 67, 6550-6552) was used instead of 2-chloro-5-methylpyrimidine, to provide P15. Yield: 345 mg, 2.11 mmol, 43%. $^1$H NMR (400 MHz, CD$_3$OD) δ 2.44 (s, 6H), 4.00 (m, 2H), 4.14 (m, 3H), 7.12 (s, 1H).

Preparation 16

Preparation of 2-azetidin-3-yl-5-cyclopropylpyrimidine

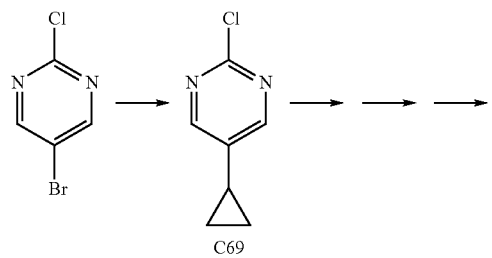

-continued

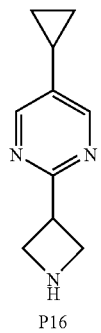

P16

A. Preparation of 2-chloro-5-cyclopropylpyrimidine (C69). Compound C69 was prepared from 5-bromo-2-chloropyrimidine according to the procedure described by D. J. Wallace & C-y. Chen, *Tetrahedron Letters*, 2002, 43, 6987-6990. $^1$H NMR (400 MHz, CDCl$_3$) δ0.79 (m, 2H), 1.14 (m, 2H), 1.87 (m, 1H), 8.36 (s, 2H).

B. Preparation of 2-azetidin-3-yl-5-cyclopropylpyrimidine (P16). Compound P16 was prepared according to the general procedures described for the synthesis of P12 in Preparation 12, except that 2-chloro-5-cyclopropylpyrimidine C69 was used in place of 2-chloro-5-methylpyrimidine. Yield: 303 mg, 1.73 mmol, 59%. $^1$H NMR (400 MHz, CD$_3$OD) δ 0.82 (m, 2H), 1.10 (m, 2H), 1.96 (m, 1H), 4.2-4.3 (br m, 5H), 8.55 (s, 2H).

Preparation 17

Preparation of 2-azetidin-3-yl-4-methylpyrimidine

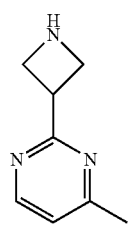

P17

Compound P17 was prepared according to the general procedure for the synthesis of P12 described in Preparation 51, except that 2-chloro-4-methylpyrimidine (the synthesis of 2-chloro-4-methylpyrimidine is described by D. B. Harden & M. J. Mokrosz, *J. Organic Chem.*, 1998, 53, 4137-4140) was used instead of 2-chloro-5-methylpyrimidine, to provide P17. Yield: 647 mg, 4.34 mmol, 87%. $^1$H NMR (400 MHz, CD$_3$OD) δ 2.52 (s, 3H), 4.0 (m, 2H), 4.12 (m, 2H), 4.18 (m, 1H), 7.23 (d, J=5.4 Hz, 1H), 8.59 (d, J=5.4 Hz, 1H).

Preparation 18

Preparation of 5-(azetidin-3-ylmethyl)-2-methylpyridine

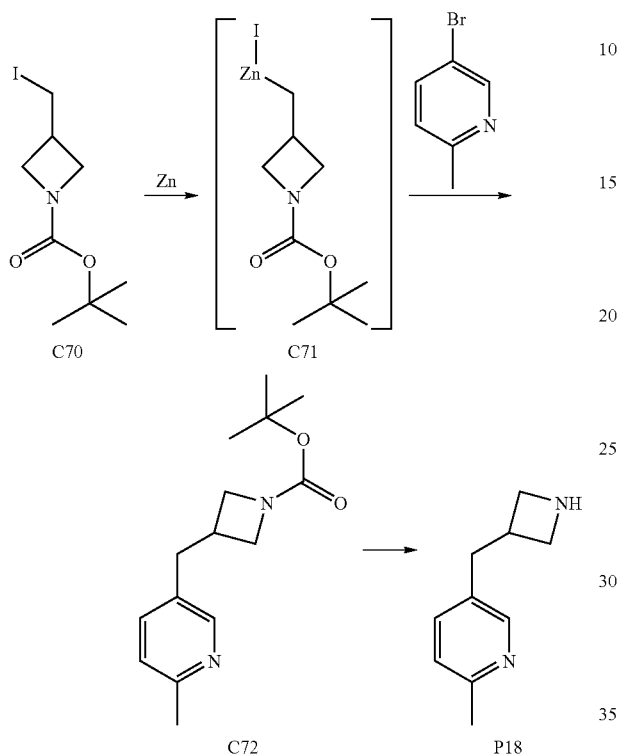

A. tert-Butyl-3-(iodomethyl)azetidine-1-carboxylate (C70) was prepared according to the procedure described by W. A. Slusarchyk & S. A. Bolton, *Bioorganic & Med. Chem. Letters*, 2002, 12, 3235-3238.

B. Preparation of {[1-(t-butoxycarbonyl)azetidin-3-yl]methyl}(iodo)zinc (C71). Zinc powder (116.5 g, 1.78 mol) was suspended in dimethylacetamide (300 mL) under argon. A mixture of trimethylsilyl chloride and 1,2-dibromoethane (7:5 v/v, 34.5 mL) was added and the mixture was stirred for 20 mins. A solution of C70 (426.8 g, 1.437 mol) in dimethylacetamide (650 mL) was added under water cooling and the reaction mixture was stirred overnight. The concentration of the resulting solution of compound C71 was about 1 mol/L and this was used in the next step.

C. Preparation of t-butyl 3-[(6-methylpyridin-3-yl)methyl]azetidine-1-carboxylate (C72). 5-Bromo-2-methylpyridine (25 g, 0.145 mol) was dissolved in dimethylacetamide (150 mL) and the solution was degassed. To the solution was added tetrakis(triphenylphosphine)palladium(0) (5 g, 4.4 mmol), copper iodide (1.7 g, 8.7 mmol) and the 1 mol/L solution of compound C71 (170 mL) under an atmosphere of argon. The reaction mixture was stirred at 50° C. for 12 h; during this time, partial decomposition of the catalyst was observed and additional amounts of tetrakis(triphenylphosphine)palladium (0) (5 g, 4.4 mmol) and copper iodide (0.9 g, 4.7 mmol) were added. The reaction mixture was stirred at 50° C. for 48 h, cooled and poured into a mixture of a saturated aqueous solution of ammonium chloride (600 mL) and diethyl ether (600 mL). The resulting mixture was stirred for 30 mins and filtered through a layer of Celite to remove insoluble impurities. The organic layer was separated and the aqueous layer was extracted with diethyl ether (4×300 mL). The combined organic extracts were dried over anhydrous sodium sulfate and evaporated. The residue was purified by silica gel chromatography (Eluant: EtOAc) to afford compound C72. Yield: 27.9 g, 0.106 mol, 73%.

D. Preparation of compound P18. Compound C72 (27.9 g, 0.106 mol) was dissolved in trifluoroacetic acid (100 mL) at 0° C. and the reaction mixture was stirred at this temperature for 2 h before evaporation. The residue was azeotroped with benzene, the resulting trifluoroacetate salt was treated with a 30% solution of potassium carbonate and the free base product was extracted with dichloromethane several times. The combined organic extracts were evaporated and purified by silica gel chromatography (Eluant: chloroform: MeOH: ammonia) to give compound P18. Yield: 3.8 g, 0.024 mol, 23%. LCMS m/z 163.1 (M+1). $^1$H NMR (400 MHz, DMSO-$d_6$) δ 2.40 (s, 3H), 2.79 (m, 3H), 2.93 (m, 1H), 3.23 (m, 2H), 3.44 (m, 2H), 7.12 (d, 1H), 7.45 (dd, 1H), 8.26 (d, 1H).

Preparation 19

Preparation of 4-(azetidin-3-yloxy)benzonitrile hydrochloride

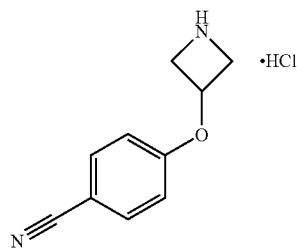

Compound P19 was prepared according to the general procedures described for the synthesis of C50 in Preparation 1, except that 4-hydroxybenzonitrile was used instead of 4-(trifluoromethyl)phenol. The final deprotection step was as described in the preparation of P2 in Preparation 2, affording P19 as a white solid. Yield: 34.9 g, 0.166 mmol, 71%. Melting point 88-90° C.

Preparation 20

Preparation of 3-(4-methylphenoxy)azetidine

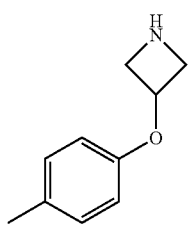

Compound P20 was prepared according to the general procedures described for the synthesis of P1 in Preparation 1, except that 4-methylphenol was used instead of 4-(trifluoromethyl)phenol, to afford P20 as a yellow oil. Yield: 3.6 g, 0.02 mol, 69%. LCMS m/z 164.1 (M+1). $^1$H NMR (400 MHz, DMSO-$d_6$) δ 2.24 (s, 3H), 3.48 (m, 2H), 3.72 (m, 2H), 4.89 (m, 1H), 6.67 (d, 2H), 7.06 (d, 2H).

Preparation 21

Preparation of 2-(azetidin-3-yloxy)pyridine

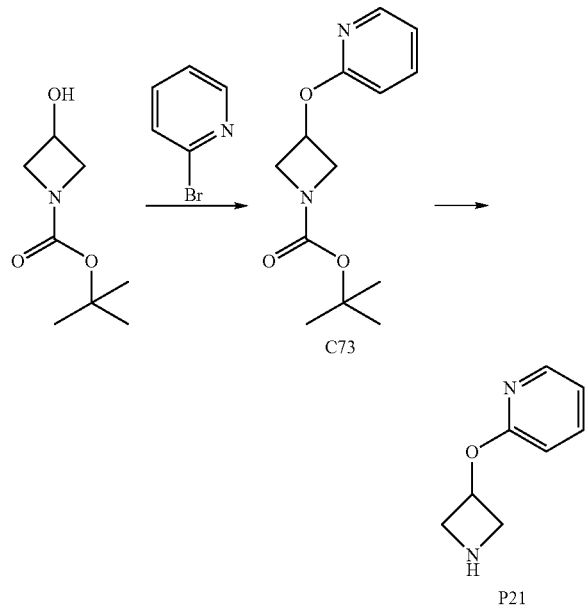

A. Preparation of t-butyl 3-(pyridin-2-yloxy)azetidine-1-carboxylate (C73). Compound C73 was prepared from tert-butyl 3-hydroxyazetidine-1-carboxylate according to the procedure described for the final step described in the preparation of Example 3, to afford C73. Yield: 578 mg, 2.31 mmol, 80%. LCMS (ESI) m/z 251.4 (M+1) $^1$H NMR (400 MHz, CDCl$_3$) δ 1.43 (s, 9H), 3.96 (m, 2H), 4.30 (m, 2H), 5.30 (m, 1H), 6.75 (m, 1H), 6.87 (m, 1H), 7.57 (m, 1H), 8.08 (m, 1H).

B. Preparation of compound P21. Compound P21 was prepared by deprotection of C73 with trifluoroacetic acid as described for t-butyl 3-hydroxyazetidine-1-carboxylate in the preparation of C19 in Example 3, before being used in the coupling step.

Preparation 22

Preparation of tert-butyl 3-(pyrazin-2-yloxy)azetidine-1-carboxylate

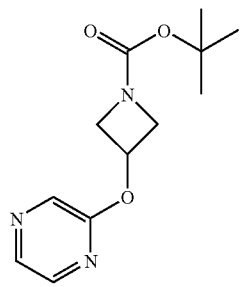

Compound P22 was prepared according to the general procedure described for the synthesis of P21 in Preparation 21, using 2-chloropyrazine in place of 2-bromopyridine, to afford P22. LCMS (ESI) m/z 252.4 (M+1). $^1$H NMR (400 MHz, CDCl$_3$) δ 1.43 (s, 9H), 3.97 (m, 2H), 4.32 (m, 2H), 5.30 (m, 1H), 8.03 (dd, J=2.5, 1.2 Hz, 1H), 8.16 (d, J=2.5 Hz, 1H), 8.26 (d, J=1.2 Hz, 1H). Compound P22 was deprotected with trifluoroacetic acid as described for tert-butyl 3-hydroxyazetidine-1-carboxylate in the preparation of C19 in Example 3, before being used in the coupling step.

Preparation 23

Preparation of tert-butyl 3-(pyrimidin-2-yloxy)azetidine-1-carboxylate

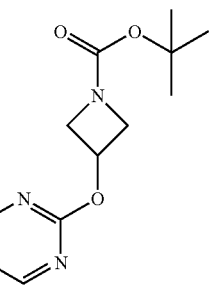

Compound P23 was prepared according to the general procedure described in the preparation of P21 in Preparation 21, except that 2-chloropyrimidine was employed instead of 2-bromopyridine, to afford P23. $^1$H NMR (400 MHz, CDCl$_3$) δ 1.42 (s, 9H), 4.02 (m, 2H), 4.30 (m, 2H), 5.29 (m, 1H), 6.97 (t, J=4.9 Hz, 1H), 8.50 (d, J=4.9 Hz, 2H). Compound P23 was deprotected with trifluoroacetic acid as described for t-butyl 3-hydroxyazetidine-1-carboxylate in the preparation of C19 in Example 3, before being used in the coupling step.

Preparation 24

Preparation of tert-butyl 3-[(4,6-dimethylpyrimidin-2-yl)oxy]azetidine-1-carboxylate

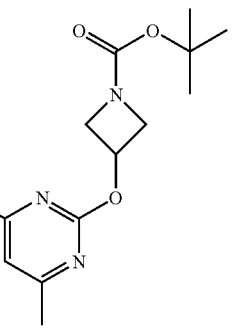

Compound P24 was prepared according to the general procedure described in the preparation of P21, except that 2-chloro-4,6-dimethylpyrimidine was used in place of 2-bromopyridine, to afford P24. LCMS (ESI) m/z 280.3 (M+1). $^1$H NMR (400 MHz, CDCl$_3$) δ 1.39 (s, 9H), 2.34 (s, 6H), 3.96 (m, 2H), 4.25 (m, 2H), 5.26 (m, 1H), 6.66 (s, 1H). Compound P24 was deprotected with trifluoroacetic acid as described for tert-butyl 3-hydroxyazetidine-1-carboxylate in the preparation of C19, Example 3 before being used in the coupling step.

Preparation 25

Preparation of 3-benzylazetidin-3-ol

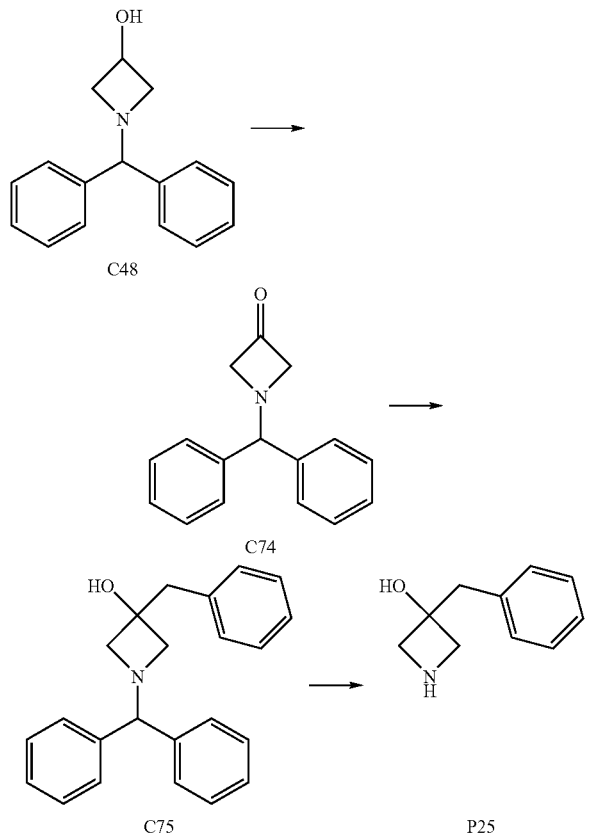

A. Preparation of 1-(diphenylmethyl)azetidin-3-one (C74). To a solution of pyridine sulfur trioxide (29.95 g, 188 mmol) in DMSO (100 mL) at 0° C., was added triethylamine (26.2 mL) and C48 (15.0 g, 62.7 mmol) in DMSO (50 mL). The mixture was warmed to room temperature after 5 mins and stirred for 3 h. The reaction was quenched with saturated aqueous sodium chloride solution and extracted with EtOH; the organic layer was washed with a saturated aqueous solution of sodium bicarbonate, saturated aqueous sodium chloride solution, dried over sodium sulfate, filtered and evaporated. The residue was purified by silica gel chromatography (Eluant: 1:1:100:200 MeOH: triethylamine: EtOAc: hexane) to afford C74 as a yellow solid. Yield: 12.2 g, 51.4 mmol, 82%. $^1$H NMR (400 MHz, CDCl$_3$) δ4.02 (s, 4H), 4.61 (s, 1H), 7.23 (m, 2H), 7.32 (m, 4H), 7.49 (m, 4H).

B. Preparation of 3-benzyl-1-(diphenylmethyl)azetidin-3-ol (C75). To a solution of C74 (5.8 g, 24.4 mmol) in anhydrous diethyl ether (200 mL) at −78° C. was added benzylmagnesium chloride (1.0M, 24.4 mL, 24.4 mmol). The mixture was gradually warmed to room temperature and stirred overnight. The mixture was cooled to 0° C., quenched with water and filtered through Celite. The filtrate was extracted with EtOAc, and the organic extract was washed with saturated aqueous sodium chloride solution, dried over sodium sulfate, filtered and evaporated. The residue was purified by silica gel chromatography (Eluant: 1:9 EtOAc:hexane) to afford C75 as a white solid. Yield: 3.0 g, 9.1 mmol, 37%.

C. Preparation of 3-benzylazetidin-3-ol (P25). Compound P25 was prepared according to the procedure described in the preparation of P1 in Preparation 1, except that C75 was used instead of C50. MS m/z 164.1 (M+1).

Preparation 26

Preparation of 3-benzyl-3-fluoroazetidine

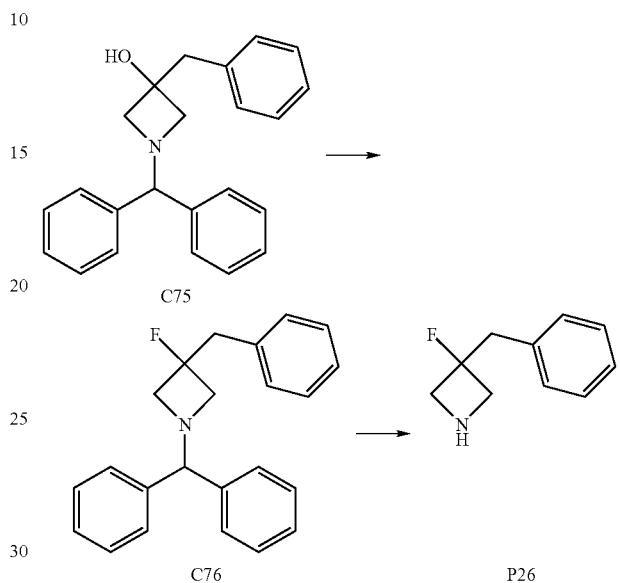

A. Preparation of 3-benzyl-1-(diphenylmethyl)-3-fluoroazetidine (C76). To a solution of C75 (0.64 g, 1.95 mmol) in dry THF (20 mL) at −78° C., was added (diethylamino)sulfur trifluoride (0.51 mL, 3.89 mmol). The mixture was slowly warmed to room temperature and stirred for 2 h. The reaction was diluted with EtOAc, washed with a saturated aqueous solution of sodium bicarbonate, then with saturated aqueous sodium chloride solution, dried over sodium sulfate, filtered and evaporated. The residue was purified by silica gel chromatography (Eluant: 1:9 EtOAc:hexane) to afford C76 as a yellow oil. Yield: 0.52 g, 1.57 mmol, 81%. MS m/z 332.1 (M+1).

B. Preparation of 3-benzyl-3-fluoroazetidine (P26). Compound P26 was prepared according to the procedure described in the preparation of P1 in Preparation 1, except that C76 was used instead of C50, to afford P26. Compound P26 was used in the next step without further purification. MS m/z 166.2 (M+1).

Preparation 27

Preparation of 3-benzylazetidine

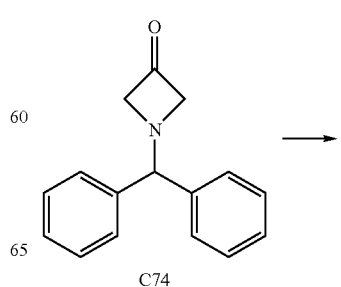

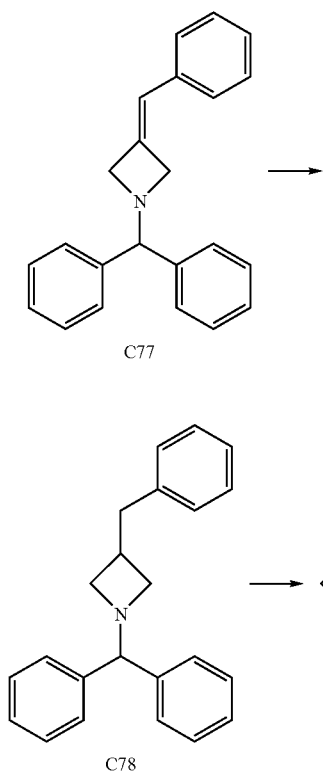

in place of C50, to afford P27. Compound P27 was used in the next step without additional purification. MS m/z 148.2 (M+1).

Preparation 28

Preparation of 5-(azetidin-3-ylmethyl)pyrimidine

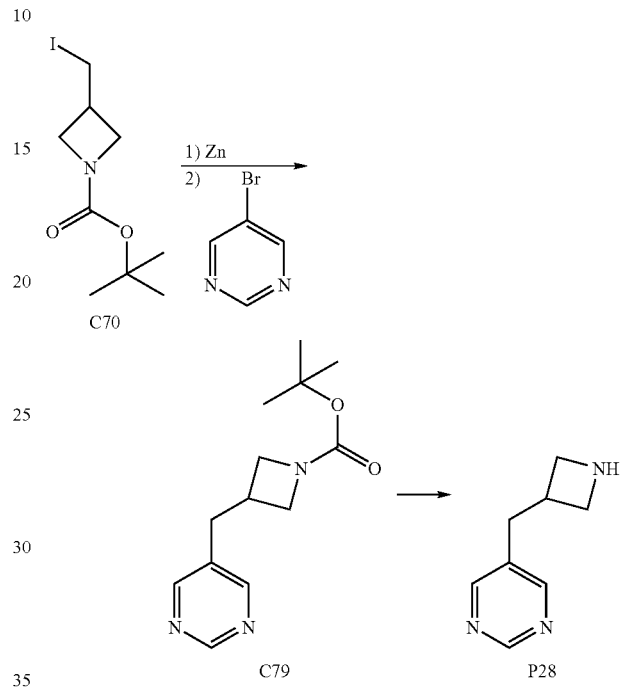

A. Preparation of 3-benzylidene-1-(diphenylmethyl)azetidine (C77). To a suspension of benzyl triphenylphosphonium bromide (7.31 g, 16.86 mmol) in anhydrous dimethyl sulfoxide, was added potassium tert-butoxide (2.08 g, 18.54 mmol). The mixture was stirred at room temperature for 10 mins before C74 (2.0 g, 8.43 mmol) was added. The reaction mixture was heated to 60° C. overnight, quenched with ice water and extracted with diethyl ether (4×300 mL). The combined organic extracts were washed with saturated aqueous sodium chloride solution, dried over sodium sulfate, filtered and evaporated. The residue was dissolved in hot hexane (100 mL) and cooled to room temperature. The resulting solid was removed by filtration, and the filtrate was evaporated to afford C77 as a yellow solid. Yield: 2.8 g, 8.93 mmol, quantitative. MS m/z 312.3 (M+1). $^1$H NMR (400 MHz, CDCl$_3$) δ 3.96 (m, 2H), 4.14 (m, 2H), 4.60 (m, 1H), 6.18 (s, 1H), 7.05 (m, 2H), 7.20-7.35 (m, 9H), 7.47 (m, 4H).

B. Preparation of 3-benzyl-1-(diphenylmethyl)azetidine (C78). To a solution of C77 (0.85 g, 2.74 mmol) in MeOH (20 mL) and hexane (20 mL), was added palladium on carbon (10% wet, 200 mg). The reaction mixture was hydrogenated in a Parr apparatus for 6 hours at room temperature under 40 psi of hydrogen. The mixture was filtered and concentrated in vacuo to afford C78, which was used in the next step without additional purification.

C. Preparation of 3-benzylazetidine (P27). Compound P27 was prepared according to the procedure described in the preparation of P1 in Preparation 1, except that C78 was used A. Preparation of Pert-butyl 3-(pyrimidin-5-ylmethyl)azetidine-1-carboxylate (C79). Compound C79 was prepared according to the general method for the synthesis of C72 in Preparation 18, except that 5-bromopyrimidine was used instead of 5-bromo-2-methylpyridine. Yield: 51.5 g, 0.206 mol, 83%.

B. Preparation of 5-(azetidin-3-ylmethyl)pyrimidine (P28). A solution of C79 (51.5 g, 0.026 mol) in MeOH (100 mL) was treated with a solution of hydrochloric acid in dioxane (4M, 250 mL), and the mixture was stirred for 18 h. Solvents were removed in vacuo, and the residue was re-evaporated with MeOH. The residue was purified twice via silica gel chromatography (Eluant: chloroform: MeOH: ammonia) to provide P28. Yield: 3.2 g, 0.021 mol, 10%. $^1$H NMR (DMSO-d$_6$) δ 2.9 (m, 3H), 3.2 (m, 2H), 3.4 (m, 2H), 8.7 (s, 2H), 9.0 (s, 1H).

Preparation 29

Preparation of 2-chloropyrido[2,3-d]pyrimidine

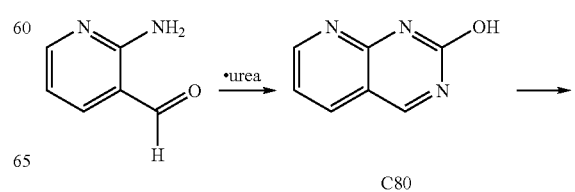

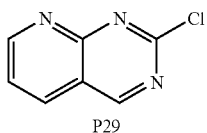

A. Preparation of pyrido[2,3-d]pyrimidin-2-ol (C80). A mixture of 2-aminonicotinaldehyde (100 g, 0.82 mol) and urea (220 g, 3.67 mol) was heated to 165° C. for 4 h. When the oil bath had cooled to 90° C., water (350 mL) was added, and the reaction was left to cool further over about 18 h. The mixture was then filtered, and the solid was suspended in water (1 L) and placed in an ultrasonic bath for 1 h. This process was repeated twice, once with water and then with MeOH, to afford C80 as a white solid, which was used in the next step without additional purification. Yield: 145 g>100%.

B. Preparation of 2-chloropyrido[2,3-d]pyrimidine (P29). A mixture of phosphorus oxychloride (750 mL) and C80 (145 g, ≦0.82 mol, from the previous step) were heated at reflux for 4 h. After cooling to room temperature, the phosphorus oxychloride was removed under reduced pressure and the resulting oil and solid were diluted with cold dichloromethane and poured onto ice. This mixture was neutralized with a saturated aqueous sodium bicarbonate solution and filtered through Celite. Extraction of the filtrate with dichloromethane (5×1.5 L) was followed by combination of the organic extracts, which were dried over sodium sulfate, filtered and concentrated in vacuo to provide P29 as an orange solid, which was used without additional purification. Yield: 30 g, 0.18 mol, 22% over two steps. LCMS m/z 165.9 (M+1). $^1$H NMR (300 MHz, CDCl$_3$) δ 7.6 (m, 1H), 8.4 (m, 1H), 9.3 (m, 1H), 9.4 (s, 1H).

TABLE 2

| Ex. No. | Prep'n Method | Side Chain* | IUPAC Name | MS m/z (M + 1) | $^{13}$C NMR (100 MHz), CDCl$_3$ (unless otherwise indicated), observed peaks, δ (ppm); additional data |
|---|---|---|---|---|---|
| 14 | Ex. 4; final purification eluant 1:2:1% EtOAc:hexanes:NH$_4$OH | com'l | 1-cyclopentyl-6-{(1R)-1-[(3R)-3-phenylpyrrolidin-1-yl]propyl}-1,5-dihydro-4H-pyrazolo[3,4-d]pyrimidin-4-one | 392.2, APCI | 9.81, 24.71, 32.33, 32.44, 32.71, 42.81, 43.17, 52.00, 52.70, 57.92, 105.10, 126.42, 126.54, 127.10, 128.56, 134.50, 158.01 |
| 15 | Ex. 14 | com'l | 1-cyclopentyl-6-{(1R)-1-[(3R)-3-phenylpyrrolidin-1-yl]ethyl}-1,5-dihydro-4H-pyrazolo[3,4-d]pyrimidin-4-one | 378.2, APCI | 18.47, 18.63, 24.72, 32.41, 32.60, 32.77, 43.02, 43.29, 51.38, 52.31, 57.74, 105.02, 126.41, 126.50, 127.08, 128.55, 134.53, 158.02 |
| 16 | Ex. 4; final purification eluant 1:1:1% EtOAc:hexanes:NH$_4$OH | P1 | 1-cyclopentyl-6-(1-{3-[4-(trifluoromethyl)phenoxy]azetidin-1-yl}ethyl)-1,5-dihydro-4H-pyrazolo[3,4-d]pyrimidin-4-one | 447.9, APCI | 17.98, 24.71, 32.39, 32.42, 57.77, 58.53, 60.06, 65.19, 65.90, 105.04, 114.58, 127.11, 134.54, 151.92, 157.96, 159.13, 159.55 |
| 17 | Ex. 16 | P2 | 6-{1-[3-(3-chlorophenoxy)azetidin-1-yl]ethyl}-1-cyclopentyl-1,5-dihydro-4H-pyrazolo[3,4-d]pyrimidin-4-one | 413.9, APCI | 18.02, 24.71, 32.38, 32.44, 57.77, 58.59, 60.18, 65.23, 65.87, 105.05, 112.98, 115.06, 121.67, 130.43, 134.56, 135.05, 151.93, 157.41, 157.92, 159.65 |
| 18 | Ex. 1; final purification gradient 0-10% EtOH/EtOAc | P4 | 1-cyclopentyl-6-{(1R)-1-[(3-pyridin-2-yl)azetidin-1-yl]ethyl}-1,5-dihydro-4H-pyrazolo[3,4-d]pyrimidin-4-one | 365.2, APCI | $^1$H NMR (400 MHz, CDCl$_3$) 1.34 (d, J = 6.8 Hz, 3H), 1.73 (m, 2H), 1.98 (m, 2H), 2.11 (m, 4H), 3.47 (dd, J = 6.8, 6.8 Hz, 1H), 3.59 (q, J = 6.8 Hz, 1H), 3.64 (dd, J = 7.0, 7.0 Hz, 1H), 3.77 (m, 2H), 3.86 (m, 1H), 5.17 (m, 1H), 7.18 (ddd, J = 7.6, 4.9 Hz, 1H), 7.23 (br d, J = 8.3 Hz, 1H), 7.65 (ddd, J = 7.7, 7.7, 1.9 Hz, 1H), 8.07 (s, 1H), 8.61 (br d, J = 5.0 Hz, 1H) |
| 19 | Ex. 18 | P5 | 1-cyclopentyl-6-{(1R)-1-(3-pyridin-4-yl)azetidin-1-yl)ethyl]-1,5-dihydro-4H-pyrazolo[3,4-d]pyrimidin-4-one | 365.2, APCI | $^1$H NMR (400 MHz, CDCl$_3$) 1.34 (d, J = 6.8 Hz, 3H), 1.73 (m, 2H), 1.99 (m, 2H), 2.12 (m, 4H), 3.29 (dd, J = 6.6, 6.6 Hz, 1H), 3.38 (dd, J = 6.6, 6.6 Hz, 1H), 3.51 (q, J = 6.8 Hz, 1H), 3.73 (m, 1H), 3.80 (m, 2H), 5.17 (m, 1H), 7.22 (m, 2H), 8.07 (s, 1H), 8.58 (m, 2H), 9.65 (br s, 1H) |
| 20 | Ex. 18 | P6 | 1-cyclopentyl-6-{(1R)-1-(3-pyridin-3-yl)azetidin-1-yl)ethyl]-1,5-dihydro-4H-pyrazolo[3,4-d]pyrimidin-4-one | 365.2, APCI | $^1$H NMR (400 MHz, CDCl$_3$) 1.35 (d, J = 6.8 Hz, 3H), 1.73 (m, 2H), 1.99 (m, 2H), 2.12 (m, 4H), 3.29 (m, 1H), 3.38 (m, 1H), 3.52 (q, J = 6.7 Hz, 1H), 3.73-3.84 (m, 3H), 5.17 (m, 1H), 7.31 (ddd, J = 7.9, 4.8, 0.8 Hz, 1H), 7.70 (br ddd, J = 7.9, 1.9, 1.9 Hz, 1H), 8.07 (s, 1H), 8.53 (m, 2H) |
| 21 | Ex. 18 | P7 | 1-cyclopentyl-6-[(1R)-1-(3-pyrimidin-5-yl)azetidin-1-yl)ethyl]-1,5-dihydro-4H-pyrazolo[3,4-d]pyrimidin-4-one | 366.2, APCI | $^1$H NMR (400 MHz, CDCl$_3$) 1.36 (d, J = 6.6 Hz, 3H), 1.73 (m, partially obscured by water, assumed 2H), 1.98 (m, 2H), 2.12 (m, 4H), 3.34 (dd, J = 7.0, 7.0 Hz, 1H), 3.41 (dd, J = 6.8, 6.8 Hz, 1H), 3.54 (q, J = 6.7 Hz, 1H), 3.75 (m, 1H), 3.84 (m, 2H), 5.17 (m, 1H), 8.07 (s, 1H), 8.74 (s, 2H), 9.15 (s, 1H), 9.65 (br s, 1H) |
| 22 | Ex. 18 | P8 | 1-cyclopentyl-6-[(1R)-1-(3-pyridazin-3-yl)azetidin-1-yl)ethyl]-1,5-dihydro-4H-pyrazolo[3,4-d]pyrimidin-4-one | 366.2, APCI | $^1$H NMR (400 MHz, CDCl$_3$) 1.36 (d, J = 66 Hz, 3H), 1.74 (m, 2H), 1.98 (m, 2H), 2.12 (m, 4H), 3.60 (dd, J = 7.1, 7.1 Hz, 1H), 3.62 (q, J = 6.7 Hz, 1H), 3.77 (dd, J = 7.2, 7.2 Hz, 1H), 3.85 (m, 2H), 4.03 (m, 1H), 5.18 (m, 1H), 7.48 (m, 2H), 8.07 (s, 1H), 9.14 (dd, J = 3.5, 3.1 Hz, 1H), 9.73 (br s, 1H) |
| 23 | Ex. 1; final purification gradient MeOH/CH$_2$Cl$_2$ | P28 | 1-cyclopentyl-6-{(1R)-1-[3-(pyrimidin-5-yl)methyl)azetidin-1-yl]ethyl}-1,5-dihydro-4H-pyrazolo[3,4-d]pyrimidin-4-one | 380.2, LCMS | 18.02, 24.67, 30.64, 32.39, 34.42, 57.52, 57.71, 57.89, 65.43, 105.03, 132.75, 134.50, 151.95, 156.51, 157.17 |
| 24 | Ex. 18 | P9 | 1-cyclopentyl-6-{(1R)-1-(3-pyrimidin-4-yl)azetidin-1-yl)ethyl]-1,5-dihydro- | 366.1, APCI | $^1$H NMR (400 MHz, CDCl$_3$) 1.34 (d, J = 6.6 Hz, 3H), 1.72 (m, 2H), 1.97 (m, 2H), 2.10 (m, 4H), 3.48 (m, 1H), 3.56-3.65 (m, 2H), |

TABLE 2-continued

| Ex. No. | Prep'n Method | Side Chain* | IUPAC Name | MS m/z (M + 1) | ¹³C NMR (100 MHz, CDCl₃ (unless otherwise indicated), observed peaks, δ (ppm): additional data |
|---|---|---|---|---|---|
| 25 | Ex. 18 | C34 (see Ex. 6) | 6-[(1R)-1-(3-pyrimidin-2-ylazetidin-1-yl)ethyl]-1-(tetrahydro-2H-pyran-4-yl)-1,5-dihydro-4H-pyrazolo[3,4-d]pyrimidin-4-one | 382.2, APCI | 3.74-3.85 (m, 3H), 5.16 (m, 1H), 7.26 (d, J = 5.2 Hz, 1H), 8.05 (s, 1H), 8.67 (d, J = 5.2 Hz, 1H), 9.21 (s, 1H), 9.82 (br s, 1H) ¹H NMR (400 MHz, CDCl₃) 1.34 (d, J = 6.6 Hz, 3H), 1.92 (m, 2H), 2.39 (m, 2H), 3.56-3.66 (m, 4H), 3.73 (dd, J = 7.4, 7.4 Hz, 1H), 3.80 (dd, J = 7.8, 7.8 Hz, 2H), 4.02 (m, 1H), 4.15 (m, 2H), 4.84 (m, 1H), 7.21 (t, J = 4.8 Hz, 1H), 8.07 (s, 1H), 8.74 (d, J = 4.8 Hz, 2H) |
| 26 | Ex. 18 | P4 | 6-[(1R)-1-(3-pyrimidin-2-ylazetidin-1-yl)ethyl]-1-(tetrahydro-2H-pyran-4-yl)-1,5-dihydro-4H-pyrazolo[3,4-d]pyrimidin-4-one | 381.2, APCI | ¹H NMR (400 MHz, CDCl₃) 1.34 (d, J = 6.6 Hz, 3H), 1.92 (m, 2H), 2.38 (m, 2H), 3.47 (dd, J = 6.9, 6.9 Hz, 1H), 3.57-3.66 (m, 4H), 3.77 (m, 2H), 3.87 (m, 1H), 4.15 (m, 2H), 4.84 (tt, J = 11.8, 4.2 Hz, 1H), 7.18 (ddd, J = 7.5, 5.0, 1.2 Hz, 1H), 7.23 (br d, J = 7.9 Hz, 1H), 7.65 (ddd, J = 7.7, 7.7, 1.9 Hz, 1H), 8.07 (s, 1H), 8.61 (ddd, J = 5.0, 1.9, 0.9 Hz, 1H) |
| 27 | Ex. 18 | P5 | 6-[(1R)-1-(3-pyridin-4-ylazetidin-1-yl)ethyl]-1-(tetrahydro-2H-pyran-4-yl)-1,5-dihydro-4H-pyrazolo[3,4-d]pyrimidin-4-one | 381.2, APCI | ¹H NMR (400 MHz, CDCl₃) 1.34 (d, J = 6.8 Hz, 3H), 1.92 (m, 2H), 2.39 (m, 2H), 3.28 (dd, J = 6.7, 6.7 Hz, 1H), 3.39 (dd, J = 6.6, 6.6 Hz, 1H), 3.51 (q, J = 6.8 Hz, 1H), 3.62 (m, 2H), 3.74 (m, 1H), 3.81 (m, 2H), 4.16 (m, 2H), 4.84 (m, 1H), 7.22 (m, 2H), 8.08 (s, 1H), 8.58 (m, 2H), 9.69 (br s, 1H) |
| 28 | Ex. 18 | P6 | 6-[(1R)-1-(3-pyridin-3-ylazetidin-1-yl)ethyl]-1-(tetrahydro-2H-pyran-4-yl)-1,5-dihydro-4H-pyrazolo[3,4-d]pyrimidin-4-one | 381.2, APCI | ¹H NMR (400 MHz, CDCl₃) 1.35 (d, J = 6.8 Hz, 3H), 1.93 (m, 2H), 2.39 (m, 2H), 3.29 (m, 1H), 3.39 (m, 1H), 3.53 (q, J = 6.7 Hz, 1H), 3.62 (m, 2H), 3.72-3.84 (m, 3H), 4.16 (m, 2H), 4.84 (m, 1H), 7.31 (ddd, J = 7.9, 5.0, 0.8 Hz, 1H), 7.69 (ddd, J = 8.1, 1.9, 1.9 Hz, 1H), 8.08 (s, 1H), 8.52-8.54 (m, 2H), 9.71 (br s, 1H) |
| 29 | Ex. 18 | P7 | 6-[(1R)-1-(3-pyrimidin-5-ylazetidin-1-yl)ethyl]-1-(tetrahydro-2H-pyran-4-yl)-1,5-dihydro-4H-pyrazolo[3,4-d]pyrimidin-4-one | 382.2, APCI | ¹H NMR (400 MHz, CDCl₃) 1.36 (d, J = 6.6 Hz, 3H), 1.92 (m, 2H), 2.39 (m, 2H), 3.34 (dd, J = 7.0, 7.0 Hz, 1H), 3.41 (dd, J = 6.9, 6.9 Hz, 1H), 3.54 (q, J = 6.7 Hz, 1H), 3.62 (m, 2H), 3.76 (m, 1H), 3.85 (m, 2H), 4.16 (m, 2H), 4.84 (tt, J = 11.6, 4.2 Hz, 1H), 8.08 (s, 1H), 8.74 (s, 2H), 9.16 (s, 1H), 9.67 (br s, 1H) |
| 30 | Ex. 18 | P8 | 6-[(1R)-1-(3-pyridazin-3-ylazetidin-1-yl)ethyl]-1-(tetrahydro-2H-pyran-4-yl)-1,5-dihydro-4H-pyrazolo[3,4-d]pyrimidin-4-one | 382.2, APCI | ¹H NMR (400 MHz, CDCl₃) Partial spectrum: 1.35 (d, J = 6.8 Hz, 3H), 1.92 (m, 2H), 2.38 (m, 2H), 3.85 (m, 1H), 4.02 (m, 1H), 4.85 (m, 1H), 7.47 (m, 2H), 8.07 (s, 1H), 9.14 (dd, J = 3.3, 3.3 Hz, 1H) |
| 31 | Ex. 1; heated 18 h, final purification gradient 0-10% EtOH/EtOAc | P10 | 1-cyclopentyl-6-{(1R)-1-[3-(2-methylpyrimidin-4-yl)azetidin-1-yl]ethyl}-1,5-dihydro-4H-pyrazolo[3,4-d]pyrimidin-4-one | 380.2, LCMS | ¹H NMR (400 MHz, CDCl₃) 1.34 (d, J = 6.8 Hz, 3H), 1.73 (m, 2H), 1.98 (m, 2H), 2.12 (m, 4H), 2.75 (s, 3H), 3.48 (m, 1H), 3.57 (q, J = 6.7 Hz, 1H), 3.61 (m, 1H), 3.72-3.79 (m, 3H), 5.17 (m, 1H), 7.06 (d, J = 5.2 Hz, 1H), 8.07 (s, 1H), 8.58 (d, J = 5.2 Hz, 1H), 9.73 (br s, 1H) |
| 32 | Ex. 31 | P10 | 6-{(1R)-1-[3-(2-methylpyrimidin-4-yl)azetidin-1-yl]ethyl}-1-(tetrahydro-2H-pyran-4-yl)-1,5-dihydro-4H-pyrazolo[3,4-d]pyrimidin-4-one | 396.1, LCMS | ¹H NMR (400 MHz, CDCl₃) 1.35 (d, J = 6.8 Hz, 3H), 1.92 (m, 2H), 2.39 (m, 2H), 2.75 (s, 3H), 3.48 (m, 1H), 3.56-3.66 (m, 4H), 3.77 (m, 3H), 4.15 (m, 2H), 4.84 (tt, J = 11.8, 4.2 Hz, 1H), 7.06 (d, J = 5.2 Hz, 1H), 8.07 (s, 1H), 8.58 (d, J = 5.2 Hz, 1H), 9.79 (br s, 1H) |
| 33 | Ex. 31 | P3 | 6-{(1R)-1-[3-(3-fluorobenzyl)azetidin-1-yl]ethyl}-1-(tetrahydro-2H-pyran-4-yl)-1,5-dihydro-4H-pyrazolo[3,4-d]pyrimidin-4-one | 414.1 | ¹H NMR (400 MHz, CDCl₃) 1.35 (d, J = 6.6 Hz, 3H), 1.92 (m, 2H), 2.39 (m, 2H), 3.22 (m, 1H), 3.40 (m, 1H), 3.55 (q, J = 6.7 Hz, 1H), 3.62 (m, 2H), 3.86 (m, 2H), 4.15 (m, 2H), 4.78-4.87 (m, 2H), 6.50 (m, 1H), 6.56 (m, 1H), 6.70 (m, 1H), 7.22 (m, 1H), 8.07 (s, 1H) |
| 34 | Ex. 31 | C37 (see Ex. 7) | 1-cyclopentyl-6-[(1R)-1-(3-quinolin-2-ylazetidin-1-yl)ethyl]-1,5-dihydro-4H-pyrazolo[3,4-d]pyrimidin-4-one | 415.1, LCMS | ¹H NMR (400 MHz, CDCl₃) 1.37 (d, J = 6.8 Hz, 3H), 1.73 (m, 2H), 1.98 (m, 2H), 2.12 (m, 4H), 3.61 (m, 2H), 3.77 (m, 1H), 3.86 (m, 2H), 4.05 (m, 1H), 5.18 (m, 1H), 7.40 (d, J = 8.5 Hz, 1H), 7.53 (ddd, J = 8.1, 6.9, 1.1 Hz, 1H), 7.73 (ddd, J = 8.5, 6.8, 1.5 Hz, 1H), 9.71 (br s, 1H) |

TABLE 2-continued

| Ex. No. | Prep'n Method | Side Chain* | IUPAC Name | MS m/z (M + 1) | $^{13}$C NMR (100 MHz), CDCl$_3$ (unless otherwise indicated), observed peaks, δ (ppm); additional data |
|---|---|---|---|---|---|
| 35 | Ex. 3; NaH, 50° C., 5 h, final purification eluant 9:1 EtOAc/EtOH | P11 | 1-cyclopentyl-6-{(1R)-1-[(3R)-3-(pyrimidin-2-yloxy)pyrrolidin-1-yl]ethyl}-1,5-dihydro-4H-pyrazolo[3,4-d]pyrimidin-4-one | 396.1, LCMS | 7.82 (br d, J = 8.1 Hz, 1H), 8.07 (s, 1H), 8.08 (br d, J = 8.5 Hz, 1H), 8.14 (d, J = 8.5 Hz, 1H), 9.84 (br s, 1H) (CD$_3$OD) 18.24, 25.82, 32.94, 33.36, 33.48, 51.06, 58.51, 59.27, 63.76, 77.90, 106.03, 116.64, 135.38, 153.44, 160.83, 162.85, 165.85 |
| 36 | Ex. 1; 50° C., 24 h, final purification eluant EtOAc | P11 | 1-cyclopentyl-6-{(1R)-1-[(3S)-3-(pyrimidin-2-yloxy)pyrrolidin-1-yl]ethyl}-1,5-dihydro-4H-pyrazolo[3,4-d]pyrimidin-4-one | 396.1, LCMS | $^1$H NMR (400 MHz, CDCl$_3$) 1.46 (d, J = 6.6 Hz, 3H), 1.70 (m, 2H), 1.96 (m, 2H), 2.09 (m, 5H), 2.32 (m, 1H), 2.76-2.89 (m, 3H), 3.23 (m, 1H), 3.55 (m, 1H), 5.14 (m, 1H), 5.44 (m, 1H), 6.93 (m, 1H), 8.05 (s, 1H), 8.49 (d, J = 4.6 Hz, 2H), 9.90 (br s, 1H) |
| 37 | Ex. 1; 2-chloro-2-oxo-1-phenylethyl acetate used; K$_2$CO$_3$/CH$_3$CN final step; purification eluant 2% MeOH/CH$_2$Cl$_2$ | com'l | 6-[(3-phenoxyazetidin-1-yl)(phenyl)methyl]-1-(tetrahydro-2H-pyran-4-yl)-1,5-dihydro-4H-pyrazolo[3,4-d]pyrimidin-4-one | 458.3, LCMS | $^1$H NMR (400 MHz, CDCl$_3$) 1.90 (m, 2H), 2.36 (m, 2H), 3.26 (dd, J = 8.3, 5.4 Hz, 1H), 3.34 (dd, J = 7.9, 5.6 Hz, 1H), 3.62 (m, 2H), 3.76 (br dd, J = 7.2, 7.2 Hz, 1H), 3.93 (br dd, J = 7.1, 7.1 Hz, 1H), 4.15 (m, 2H), 4.58 (s, 1H), 4.85 (m, 2H), 6.76 (br d, J = 8.6 Hz, 2H), 6.97 (t, J = 7.4 Hz, 1H), 7.27 (m, 2H), 7.36 (m, 3H), 7.48 (br d, J = 7.9 Hz, 2H), 8.05 (s, 1H), 9.98 (br s, 1H) |
| 38 | Ex. 1; K$_2$CO$_3$/CH$_3$CN final step; purification gradient 1-2.5% MeOH/CH$_2$Cl$_2$ | Com'l | 6-[(1R)-1-(3-phenoxyazetidin-1-yl)ethyl]-1-(tetrahydro-2H-pyran-4-yl)-1,5-dihydro-4H-pyrazolo[3,4-d]pyrimidin-4-one | 396.4, LCMS | $^1$H NMR (400 MHz, CD$_3$OD) 1.38 (d, J = 6.8 Hz, 3H), 1.89 (m, 2H), 2.29 (m, 2H), 3.28 (dd, assumed, partially obscured by solvent peak, J = 7.9, 5.4 Hz, 1H), 3.34 (dd, assumed, partially obscured by solvent peak, J = 8.1, 5.2 Hz, 1H), 3.61 (m, 3H), 3.85 (dd, J = 7.0, 7.0 Hz, 1H), 3.93 (dd, J = 6.9, 6.9 Hz, 1H), 4.08 (m, 2H), 4.87 (m, 1H), 4.98 (tt, J = 11.7, 4.2 Hz, 1H), 6.80 (d, J = 8.2 Hz, 2H), 6.93 (t, J = 7.8 Hz, 1H), 7.26 (dd, J = 7.8, 7.8 Hz, 2H), 8.03 (s, 1H) 9.18, 24.51, 25.12, 32.03, 32.20, 36.88, 53.84, 57.74, 58.73, 66.98, 70.96, 105.34, 118.33, 121.22, 134.63, 136.61, 151.68, 157.75, 158.04, 159.13, 159.73 |
| 39 | Ex. 1; (1S)-1-(chlorocarbonyl)propyl acetate used | C39 (see Ex. 8) | 6-{(1R)-1-[3-(6-methylpyridin-2-yl)azetidin-1-yl]propyl}-1-(tetrahydro-2H-pyran-4-yl)-1,5-dihydro-4H-pyrazolo[3,4-d]pyrimidin-4-one | 409.1, LCMS | 9.23, 25.17, 32.09, 32.20, 36.94, 53.91, 57.53, 58.89, 67.03, 70.94, 105.38, 121.83, 121.95, 134.65, 136.47, 149.45, 157.77, 159.11, 160.22 |
| 40 | Ex. 39 | P4 | 6-[(1R)-1-(3-pyridin-2-ylazetidin-1-yl)propyl]-1-(tetrahydro-2H-pyran-4-yl)-1,5-dihydro-4H-pyrazolo[3,4-d]pyrimidin-4-one | 395.1, LCMS | 9.29, 15.39, 32.08, 32.21, 53.97, 57.08, 57.92, 67.03, 134.69, 157.29 (only peaks observed) |
| 41 | Ex. 39 | P12 | 6-{(1R)-1-[3-(5-methylpyridin-2-yl)azetidin-1-yl]propyl}-1-(tetrahydro-2H-pyran-4-yl)-1,5-dihydro-4H-pyrazolo[3,4-d]pyrimidin-4-one | 410.2, LCMS | 9.24, 25.06, 32.06, 32.21, 37.25, 53.96, 57.04, 57.95, 67.03, 70.88, 134.68, 155.60 (only peaks observed) |
| 42 | Ex. 39 | C42 (see Ex. 10) | 6-{(1R)-1-[3-(5-chloropyrimidin-2-yl)azetidin-1-yl]propyl}-1-(tetrahydro-2H-pyran-4-yl)-1,5-dihydro-4H-pyrazolo[3,4-d]pyrimidin-4-one | 430.1, LCMS | 18.06, 23.86, 24.66, 31.13, 32.37, 36.57, 57.56, 57.65, 58.16, 65.38, 105.00, 122.94, 131.66, 134.46, 136.07, 148.84, 151.99, 156.33, 157.86, 160.23 |
| 43 | Ex. 1 | P18 | 1-cyclopentyl-6-{(1R)-1-[3-[(6-methylpyridin-3-yl)methyl]azetidin-1-yl]ethyl}-1,5-dihydro-4H-pyrazolo[3,4-d]pyrimidin-4-one | 393.2, LCMS | 18.20, 29.32, 32.16, 43.17, 53.74, 57.89, 58.68, 65.40, 67.01, 105.32, 118.80, 134.71, 157.03, 160.83 |
| 44 | Ex. 1 | P13 | 6-{(1R)-1-[3-(pyrimidin-2-ylmethyl)azetidin-1-yl]ethyl}-1-(tetrahydro-2H-pyran-4-yl)-1,5-dihydro-4H-pyrazolo[3,4-d]pyrimidin-4-one | 396.1, LCMS | |

TABLE 2-continued

| Ex. No. | Prep'n Method | Side Chain* | IUPAC Name | MS m/z (M + 1) | ¹³C NMR (100 MHz, CDCl₃ (unless otherwise indicated), observed peaks, δ (ppm); additional data |
|---|---|---|---|---|---|
| 45 | Ex. 1; final purification eluant 10% MeOH/EtOAc | P14 | 1:1 cis- and trans-1-cyclopentyl-6-[(1R)-1-(3-pyrimidin-2-ylpyrrolidin-1-yl)ethyl]-1,5-dihydro-4H-pyrazolo[3,4-d]pyrimidin-4-one | 380.2, LCMS | 13.32, 14.02, 20.23, 20.96, 22.59, 24.67, 24.72, 30.59, 30.80, 32.28, 32.31, 32.36, 45.04, 45.30, 49.45, 50.81, 51.83, 56.59, 57.50, 57.60, 58.20, 61.18, 104.92, 105.13, 118.78, 134.28, 134.35, 152.34, 152.45, 157.50, 158.58, 158.67, 161.65, 162.47 |
| 46 | Ex. 1; final purification eluant 94.5:1 EtOAc/MeOH/NH₄OH | P12 | 1-cyclopentyl-6-{(1R)-1-[3-(5-methylpyrimidin-2-yl)azetidin-1-yl]ethyl}-1,5-dihydro-4H-pyrazolo[3,4-d]pyrimidin-4-one | 380.1, APCI | ¹H NMR (400 MHz, CDCl₃) 1.33 (d, J = 6.6 Hz, 3H), 1.70 (m, 2H), 1.95 (m, 2H), 2.09 (m, 4H), 2.30 (s, 3H), 3.58 (br m, 2H), 3.69 (br m, 1H), 3.79 (br m, 2H), 3.97 (m, 1H), 5.15 (m, 1H), 8.04 (s, 1H), 8.53 (s, 2H) |
| 47 | Ex. 1; final purification gradient 0-20% MeOH/CH₂Cl₂ | P12 | 6-{(1R)-1-[3-(5-methylpyrimidin-2-yl)azetidin-1-yl]ethyl}-1-(tetrahydro-2H-pyran-4-yl)-1,5-dihydro-4H-pyrazolo[3,4-d]pyrimidin-4-one | 396.1, APCI | ¹H NMR (400 MHz, CDCl₃) 1.35 (d, J = 6.4 Hz, 3H), 1.91 (m, 2H), 2.32 (s, 3H), 2.37 (m, 2H), 3.56-4.01 (m, 6H), 3.61 (m, 2H), 4.14 (m, 2H), 4.85 (m, 1H), 8.05 (s, 1H), 8.55 (s, 2H) |
| 48 | Ex. 1; final purification preparative TLC; eluant 92:7:1 EtOAc/MeOH/NH₄OH | P16 | 6-{(1R)-1-[3-(5-cyclopropylpyrimidin-2-yl)azetidin-1-yl]ethyl}-1-(tetrahydro-2H-pyran-4-yl)-1,5-dihydro-4H-pyrazolo[3,4-d]pyrimidin-4-one | 422.1, APCI | ¹H NMR (400 MHz, CDCl₃) 0.76 (m, 2H), 1.07 (m, 2H), 1.32 (d, J = 6.8 Hz, 3H), 1.84 (m, 1H), 1.89 (m, 2H), 2.34 (m, 2H), 3.52-3.67 (m, 5H), 3.76 (dd, J = 3.7, 3.7 Hz, 2H), 3.94 (m, 1H), 4.11 (br d, J = 11.3 Hz, 2H), 4.83 (m, 1H), 8.03 (s, 1H), 8.42 (s, 2H) |
| 49 | Ex. 48 | P16 | 1-cyclopentyl-6-{(1R)-1-[3-(5-cyclopropylpyrimidin-2-yl)azetidin-1-yl]ethyl}-1,5-dihydro-4H-pyrazolo[3,4-d]pyrimidin-4-one | 406.1, APCI | ¹H NMR (400 MHz, CDCl₃) 0.78 (m, 2H), 1.09 (m, 2H), 1.32 (d, J = 6.8 Hz, 3H), 1.71 (m, 2H), 1.86 (tt, J = 8.5, 5.1 Hz, 1H), 1.96 (m, 2H), 2.10 (m, 4H), 3.56 (m, 2H), 3.67 (dd, J = 7.0, 7.0 Hz, 1H), 3.76 (dd, J = 7.5, 7.5 Hz, 2H), 3.95 (m, 1H), 5.16 (m, 1H), 8.05 (s, 1H), 8.44 (s, 2H) |
| 50 | Ex. 1; final purification gradient 0-100% (10% MeOH/EtOAc)/heptane | P15 | 6-{(1R)-1-[3-(4,6-dimethylpyrimidin-2-yl)azetidin-1-yl]ethyl}-1-(tetrahydro-2H-pyran-4-yl)-1,5-dihydro-4H-pyrazolo[3,4-d]pyrimidin-4-one | 410.1, APCI | ¹H NMR (400 MHz, CDCl₃) 1.32 (d, J = 6.6 Hz, 3H), 1.91 (br d, J = 12.5 Hz, 2H), 2.37 (m, 2H), 2.46 (s, 6H), 3.54-3.64 (m, 4H), 3.69 (m, 1H), 3.75 (m, 1H), 3.89 (m, 1H), 4.13 (m, 2H), 4.83 (tt, J = 11.7, 4.2 Hz, 1H), 6.89 (s, 1H), 8.05 (s, 1H) |
| 51 | Ex. 47 | P15 | 1-cyclopentyl-6-{(1R)-1-[3-(4,6-dimethylpyrimidin-2-yl)azetidin-1-yl]ethyl}-1,5-dihydro-4H-pyrazolo[3,4-d]pyrimidin-4-one | 394.1, APCI | ¹H NMR (400 MHz, CDCl₃) 1.32 (d, J = 6.8 Hz, 3H), 1.72 (m, 2H), 1.97 (m, 2H), 2.10 (m, 4H), 2.47 (s, 6H), 3.58 (m, 2H), 3.70 (dd, J = 7.0, 7.0 Hz, 1H), 3.75 (m, 2H), 3.89 (m, 1H), 5.16 (m, 1H), 6.89 (s, 1H), 8.05 (s, 1H) |
| 52 | Ex. 47 | P17 | 1-cyclopentyl-6-{(1R)-1-[3-(4-methylpyrimidin-2-yl)azetidin-1-yl]ethyl}-1,5-dihydro-4H-pyrazolo[3,4-d]pyrimidin-4-one | 380.1, APCI | ¹H NMR (400 MHz, CDCl₃) 1.32 (d, J = 6.6 Hz, 3H), 1.70 (m, 2H), 1.96 (m, 2H), 2.09 (m, 4H), 2.52 (s, 3H), 3.57 (m, 2H), 3.69 (dd, J = 7.0, 7.0 Hz, 1H), 3.76 (m, 2H), 3.94 (m, 1H), 5.16 (m, 1H), 7.03 (d, J = 5.2 Hz, 1H), 8.05 (s, 1H), 8.55 (d, J = 5.2 Hz, 1H) |
| 53 | Ex. 47 | P17 | 6-{(1R)-1-[3-(4-methylpyrimidin-2-yl)azetidin-1-yl]ethyl}-1-(tetrahydro-2H-pyran-4-yl)-1,5-dihydro-4H-pyrazolo[3,4-d]pyrimidin-4-one | 396.1, APCI | ¹H NMR (400 MHz, CDCl₃) 1.33 (d, J = 6.6 Hz, 3H), 1.91 (m, 2H), 2.38 (m, 2H), 2.53 (s, 3H), 3.57-3.65 (m, 4H), 3.71 (dd, J = 6.9, 6.9 Hz, 1H), 3.78 (m, 2H), 3.95 (m, 1H), 4.14 (m, 2H), 4.84 (m, 1H), 7.05 (d, J = 5.2 Hz, 1H), 8.06 (s, 1H), 8.56 (d, J = 5.2 Hz, 1H) |
| 54 | Ex. 4; NEt₃ added to reaction; purified by HPLC, gradient 30-70% CH₃CN/water with constant 0.1% NH₄OH | P19 | 4-[(1-{1-[4-oxo-1-(tetrahydro-2H-pyran-4-yl)-4,5-dihydro-1H-pyrazolo[3,4-d]pyrimidin-6-yl]ethyl}azetidin-3-yl)oxy]benzonitrile | 421.5, LCMS | ¹H NMR (400 MHz, CD₃OD) 1.38 (d, J = 6.6 Hz, 3H), 1.89 (m, 2H), 2.29 (m, 2H), 3.30 (m, 1H, assumed, obscured by solvent peak), 3.37 (dd, J = 8.1, 5.2 Hz, 1H), 3.61 (m, 3H), 3.88 (dd, J = 7.0, 7.0 Hz, 1H), 3.94 (dd, J = 7.1, 7.1 Hz, 1H), 4.09 (m, 2H), 4.97 (m, 2H), 6.98 (d, J = 8.7 Hz, 2H), 7.65 (d, J = 8.7 Hz, 2H), 8.03 (s, 1H) |
| 55 | Ex. 4; final purification eluant 100:1 CHCl₃/MeOH | P19 | 4-({1-[1-(1-cyclopentyl-4-oxo-4,5-dihydro-1H-pyrazolo[3,4-d]pyrimidin-6-yl)ethyl]azetidin-3-yl}oxy)benzonitrile | 405.0, APCI | 17.96, 24.71, 32.39, 32.44, 57.78, 58.41, 59.86, 65.14, 66.07, 105.05, 115.31, 118.78, 134.17, 134.56, 159.92 |

TABLE 2-continued

| Ex. No. | Prep'n Method | Side Chain* | IUPAC Name | MS m/z (M + 1) | ¹³C NMR (100 MHz), CDCl₃ (unless otherwise indicated), observed peaks, δ (ppm): additional data |
|---|---|---|---|---|---|
| 56 | Ex. 4; final purification Chiralpak AD; eluant 75:25 heptane/IPA | P20 | 1-cyclopentyl-6-{(1S)-1-[3-(4-methylphenoxy)azetidin-1-yl]ethyl]}-1,5-dihydro-4H-pyrazolo[3,4-d]pyrimidin-4-one | 394.0, APCI | 18.05, 20.43, 24.72, 32.39, 32.44, 57.77, 58.79, 60.55, 65.20, 65.62, 105.07, 114.40, 130.09, 130.80, 134.56, 151.96, 154.55, 157.90; First enantiomer to elute |
| 57 | Ex. 56 | P20 | 1-cyclopentyl-6-{(1R)-1-[3-(4-methylphenoxy)azetidin-1-yl]ethyl]}-1,5-dihydro-4H-pyrazolo[3,4-d]pyrimidin-4-one | 394.1, APCI | 18.05, 20.43, 24.72, 32.41, 32.45, 57.78, 58.79, 60.55, 65.20, 65.63, 105.08, 114.42, 130.09, 130.82, 134.57, 151.98, 154.55, 157.90; Second enantiomer to elute |
| 58 | Ex. 4 | P20 | 6-{1-[3-(4-methylphenoxy)azetidin-1-yl]ethyl}-1-(tetrahydro-2H-pyran-4-yl)-1,5-dihydro-4H-pyrazolo[3,4-d]pyrimidin-4-one | 410.0, APCI | 18.13, 20.43, 32.18, 53.79, 58.80, 60.58, 65.20, 65.62, 67.00, 105.29, 114.39, 130.09, 130.82, 134.74, 151.77, 154.54, 157.75, 160.17 |
| 59 | Ex. 4; final purification Chiralcel OD, 10 × 50 cm, 250 mL/min; eluant 65:35 heptane/EtOH | com'l | 1-cyclopentyl-6-[(1S)-1-(3-phenoxyazetidin-1-yl)ethyl]-1,5-dihydro-4H-pyrazolo[3,4-d]pyrimidin-4-one | 380.0, APCI | 18.07, 24.72, 32.39, 32.44, 57.77, 58.77, 60.49, 65.22, 65.53, 105.08, 114.55, 121.47, 129.67, 134.57, 151.96, 156.69, 157.93; Retention time 18 mins |
| 60 | Ex. 59 | com'l | 1-cyclopentyl-6-[(1R)-1-(3-phenoxyazetidin-1-yl)ethyl]-1,5-dihydro-4H-pyrazolo[3,4-d]pyrimidin-4-one | 380.0, APCI | 18.07, 24.72, 32.39, 32.45, 57.77, 58.77, 60.49, 65.23, 65.55, 105.08, 114.55, 121.47, 129.67, 134.57, 151.98, 156.69, 157.93; Retention time 26 mins |
| 61 | Ex. 4; 2-bromobutanoyl bromide used | comm'l | 6-[1-(3-phenoxyazetidin-1-yl)propyl]-1-(tetrahydro-2H-pyran-4-yl)-1,5-dihydro-4H-pyrazolo[3,4-d]pyrimidin-4-one | 410.0, APCI | 9.18, 25.29, 32.06, 32.18, 53.96, 59.07, 60.61, 65.69, 67.00, 71.15, 105.35, 114.53, 121.47, 129.65, 134.68, 151.56, 156.65, 157.69 |
| 62 | Ex. 61 | P20 | 6-{1-[3-(4-methylphenoxy)azetidin-1-yl]propyl}-1-(tetrahydro-2H-pyran-4-yl)-1,5-dihydro-4H-pyrazolo[3,4-d]pyrimidin-4-one | 424.0, APCI | 9.18, 20.43, 25.29, 32.08, 32.20, 53.96, 59.10, 60.69, 65.80, 67.00, 71.14, 105.37, 114.40, 130.09, 130.83, 134.69, 151.58, 157.72 |
| 63 | Ex. 4 | P20 | 1-isopropyl-6-{1-[3-(4-methylphenoxy)azetidin-1-yl]ethyl]-1,5-dihydro-4H-pyrazolo[3,4-d]pyrimidin-4-one | 368.0, APCI | 18.04, 20.43, 22.03, 49.16, 58.77, 60.57, 65.17, 65.63, 105.08, 114.42, 130.09, 130.80, 134.54, 140.88, 151.43, 154.57, 157.92 |
| 64 | Ex. 61 | P21 | 6-{1-[3-(pyridin-2-yloxy)azetidin-1-yl]propyl}-1-(tetrahydro-2H-pyran-4-yl)-1,5-dihydro-4H-pyrazolo[3,4-d]pyrimidin-4-one | 411.0, APCI | 9.14, 25.36, 32.06, 32.15, 53.87, 59.31, 60.49, 64.54, 66.97, 71.18, 105.34; 110.90; 117.24, 134.65, 138.76, 146.90, 151.62, 157.71, 158.87, 162.36 |
| 65 | Ex. 61 | com'l | 1-isopropyl-6[1-(3-phenoxyazetidin-1-yl)propyl]-1,5-dihydro-4H-pyrazolo[3,4-d]pyrimidin-4-one | 368.0, APCI | 9.18, 21.92, 22.04, 25.30, 49.29, 59.04, 60.60, 65.75, 71.26, 105.14, 114.55, 121.43, 129.64, 134.47, 151.25, 156.71, 157.81, 158.28 |
| 66 | Ex. 61 | P20 | 1-isopropyl-6-{1-[3-(4-methylphenoxy)azetidin-1-yl]propyl}-1,5-dihydro-4H-pyrazolo[3,4-d]pyrimidin-4-one | 382.0, APCI | 9.17, 20.41, 21.91, 22.03, 25.32, 49.28, 59.04, 60.67, 65.84, 71.26, 105.14, 114.40, 130.06, 130.75, 134.45, 154.58, 157.80, 158.37 |
| 67 | Ex. 4 | P22 | 6-{1-[3-(pyrazin-2-yloxy)azetidin-1-yl]ethyl]-1-(tetrahydro-2H-pyran-4-yl)-1,5-dihydro-4H-pyrazolo[3,4-d]pyrimidin-4-one | 398.0, APCI | 18.11, 32.15, 53.82, 58.73, 60.10, 64.92, 65.23, 67.00, 105.31, 134.75, 135.74, 137.31, 140.55, 157.83, 158.86 |

TABLE 2-continued

| Ex. No. | Prep'n Method | Side Chain* | IUPAC Name | MS m/z (M + 1) | 13C NMR (100 MHz), CDCl3 (unless otherwise indicated), observed peaks, δ (ppm): additional data |
|---|---|---|---|---|---|
| 68 | Ex. 3 | com'l | 6-{1-[3-(quinoxalin-2-yloxy)azetidin-1-yl]ethyl}-1-(tetrahydro-2H-pyran-4-yl)-1,5-dihydro-4H-pyrazolo[3,4-d]pyrimidin-4-one | 448.0, APCI | 18.13, 32.15, 53.81, 58.73, 60.28, 65.11, 65.26, 66.98, 105.31, 127.01, 127.31, 128.98, 130.34, 134.75, 138.94, 155.81 |
| 69 | Ex. 4 | P23 | 6-{1-[3-(pyrimidin-2-yloxy)azetidin-1-yl]ethyl}-1-(tetrahydro-2H-pyran-4-yl)-1,5-dihydro-4H-pyrazolo[3,4-d]pyrimidin-4-one | 398.0, APCI | 18.14, 32.17, 53.73, 58.49, 60.30, 65.20, 65.32, 67.00, 105.28, 115.63, 134.74, 151.76, 157.75, 159.41 |
| 70 | Ex. 3 | com'l | 6-{1-[3-(quinolin-2-yloxy)azetidin-1-yl]ethyl}-1-(tetrahydro-2H-pyran-4-yl)-1,5-dihydro-4H-pyrazolo[3,4-d]pyrimidin-4-one | 447.0, APCI | 18.23 (br), 32.15, 53.76, 59.04, 60.64, 64.51, 65.26 (br), 67.00, 112.50, 124.34, 125.15, 127.40, 129.64, 134.74, 139.10, 146.28, 157.86, 160.46 |
| 71 | Ex. 3 | com'l | 6-{1-[3-(phthalazin-1-yloxy)azetidin-1-yl]ethyl}-1-(tetrahydro-2H-pyran-4-yl)-1,5-dihydro-4H-pyrazolo[3,4-d]pyrimidin-4-one | 448.0, APCI | 18.20, 32.14, 53.73, 59.26, 59.85, 65.29, 66.29, 66.97, 105.28, 119.47, 122.74, 125.90, 128.86, 132.30, 132.52, 134.71, 148.35, 151.73, 157.78, 160.16 |
| 72 | Ex. 3 | com'l | 6-(1-{3-[(6-methylpyridazin-3-yl)oxy]azetidin-1-yl}ethyl)-1-(tetrahydro-2H-pyran-4-yl)-1,5-dihydro-4H-pyrazolo[3,4-d]pyrimidin-4-one | 412.0, APCI | 18.17, 21.39, 32.13, 53.66, 59.13, 59.70, 65.13, 65.88, 66.97, 105.24, 117.29, 130.26, 134.70, 151.70, 155.77, 157.81, 162.34 dihydro-4H-pyrazolo[3,4-d]pyrimidin-4-one |
| 73 | Ex. 3 | com'l | 6-{1-[3-(pyrimidin-4-yloxy)azetidin-1-yl]ethyl}-1-(tetrahydro-2H-pyran-4-yl)-1,5-dihydro-4H-pyrazolo[3,4-d]pyrimidin-4-one | 398.4, LCMS | 18.05 (br), 32.17, 53.87, 58.73, 59.83, 65.13, 67.00, 105.32, 108.61, 134.75, 157.54, 158.37 |
| 74 | Ex. 3 | com'l | 6-(1-{3-[(4,6-dimethylpyrimidin-2-yl)oxy]azetidin-1-yl}ethyl)-1-(tetrahydro-2H-pyran-4-yl)-1,5-dihydro-4H-pyrazolo[3,4-d]pyrimidin-4-one | 426.4, LCMS | 18.13 (br), 23.78, 32.15, 53.70, 58.46, 60.58, 64.75, 65.11 (br), 66.98, 105.28, 114.46, 134.72, 169.46 |
| 75 | Ex. 3 | P29 | 6-{1-[3-(pyrido[2,3-d]pyrimidin-2-yloxy)azetidin-1-yl]ethyl}-1-(tetrahydro-2H-pyran-4-yl)-1,5-dihydro-4H-pyrazolo[3,4-d]pyrimidin-4-one | 449.0, APCI | 18.20, 32.14, 53.70, 58.76, 59.89, 65.40, 66.35, 66.98, 105.29, 116.30, 121.41, 134.75, 136.74, 158.31, 165.33 |
| 76 | Ex. 3 | com'l | 6-{1-[3-(quinazolin-1-yloxy)azetidin-1-yl]ethyl}-1-(tetrahydro-2H-pyran-4-yl)-1,5-dihydro-4H-pyrazolo[3,4-d]pyrimidin-4-one | 448.3, LCMS | 18.16 (br), 32.17, 53.72, 58.53, 60.57, 65.23, 65.37, 67.00, 122.01, 125.47, 126.78, 127.37, 134.74, 163.88 |
| 77 | Ex. 4; final purification Chiralcel OD-H, 4.6 mm × 25 cm, 1 mL/min, eluant 85:15 heptane/EtOH | P21 | 6-{(1R)-1-[3-(pyridin-2-yloxy)azetidin-1-yl]ethyl}-1-(tetrahydro-2H-pyran-4-yl)-1,5-dihydro-4H-pyrazolo[3,4-d]pyrimidin-4-one | 397.0, APCI | 18.23, 32.14, 53.75, 59.07, 60.40, 64.33, 65.25, 67.00, 105.31, 110.92, 117.29, 134.72, 138.78, 146.93, 157.74, 162.34; retention time 13.32 min, second enantiomer to elute |
| 78 | Ex. 3 | com'l | 6-{1-[3-(1,8-naphthyridin-2-yloxy)azetidin-1-yl]ethyl}-1-(tetrahydro-2H-pyran-4-yl)-1,5-dihydro-4H-pyrazolo[3,4-d]pyrimidin-4-one | 448.0, APCI | 18.22, 32.14, 32.18, 53.75, 59.29, 59.77, 65.29, 65.47, 67.00, 105.32, 114.18, 119.50, 120.26, 134.75, 136.71, 139.58, 151.73, 152.89, 154.99, 157.71, 163.27 |

TABLE 2-continued

| Ex. No. | Prep'n Method | Side Chain* | IUPAC Name | MS m/z (M + 1) | ¹³C NMR (100 MHz), CDCl₃ (unless otherwise indicated), observed peaks, δ (ppm): additional data |
|---|---|---|---|---|---|
| 79 | Ex. 3 | com'l | 6-(1-{3-[(3-methylquinoxalin-2-yl)oxy]azetidin-1-yl}ethyl)-1-(tetrahydro-2H-pyran-4-yl)-1,5-dihydro-4H-pyrazolo[3,4-d]pyrimidin-4-one | 462.0, APCI | 18.23 (br), 20.26, 32.14, 53.82, 58.85, 60.48, 65.13, 65.34 (br), 67.00, 105.32, 126.84, 126.90, 128.02, 129.04, 134.75, 138.78, 139.46, 147.46, 154.82, 157.81 |
| 80 | Ex. 4 | P24 | 1-cyclopentyl-6-(1-{3-[(4,6-dimethylpyrimidin-2-yl)oxy]azetidin-1-yl}ethyl)-1,5-dihydro-4H-pyrazolo[3,4-d]pyrimidin-4-one | 410.0, APCI | 18.10, 23.78, 24.69, 32.38, 57.71, 58.41, 60.60, 64.81, 65.20, 105.04, 114.42, 134.53, 157.90, 163.67, 169.43 |
| 81 | Ex. 1; CH₃CN, K₂CO₃; purification eluant 5% MeOH/CHCl₃ | P25 | 6-[(1R)-1-(3-benzyl-3-hydroxyazetidin-1-yl)ethyl]-1-(tetrahydro-2H-pyran-4-yl)-1,5-dihydro-4H-pyrazolo[3,4-d]pyrimidin-4-one | 410.1, LCMS | ¹H NMR (300 MHz, CDCl₃) 1.31 (d, J = 6.7 Hz, 3H), 1.90 (m, 2H), 2.38 (m, 2H), 3.05 (s, 2H), 3.21-3.54 (m, 5H), 3.61 (m, 2H), 4.14 (m, 2H), 4.83 (m, 1H), 7.30 (m, 5H), 8.15 (s, 1H) |
| 82 | Ex. 81 | P26 | 6-[(1R)-1-(3-benzyl-3-fluoroazetidin-1-yl)ethyl]-1-(tetrahydro-2H-pyran-4-yl)-1,5-dihydro-4H-pyrazolo[3,4-d]pyrimidin-4-one | 412.2, LCMS | ¹H NMR (300 MHz, CDCl₃) 1.32 (d, J = 6.7 Hz, 3H), 1.91 (m, 2H), 2.37 (m, 2H), 2.76-3.66 (m, 8H), 3.86 (m, 1H), 4.14 (m, 2H), 4.83 (m, 1H), 7.12-7.36 (m, 5H), 8.05 (s, 1H) |
| 83 | Ex. 1; CH₃CN; purification eluant 5% MeOH/CHCl₃ | P27 | 6-[(1R)-1-(3-benzylazetidin-1-yl)ethyl]-1-(tetrahydro-2H-pyran-4-yl)-1,5-dihydro-4H-pyrazolo[3,4-d]pyrimidin-4-one | 394.2, LCMS | ¹H NMR (300 MHz, CDCl₃) 1.27 (d, J = 6.7 Hz, 3H), 1.91 (m, 2H), 2.37 (m, 2H), 2.79 (m, 1H), 2.91 (m, 3H), 3.05 (dd, J = 6.6, 6.6 Hz, 1H), 3.42 (m, 3H), 3.61 (m, 2H), 4.14 (m, 2H), 4.83 (m, 1H), 7.12-7.31 (m, 5H), 8.05 (s, 1H) |
| 84 | Ex. 5 | com'l | 2-chloro-4-[(1-{1-[4-oxo-1-(tetrahydro-2H-pyran-4-yl)-4,5-dihydro-1H-pyrazolo[3,4-d]pyrimidin-6-yl]ethyl}azetidin-3-yl)oxy]benzonitrile | 455.3, LCMS | ¹H NMR (400 MHz, CD₃OD) 1.38 (d, J = 6.6 Hz, 3H), 1.89 (m, 2H), 2.29 (m, 2H), 3.31 (m, 1H, assumed, obscured by solvent peak), 3.38 (dd, J = 8.1, 5.2 Hz, 1H), 3.61 (m, 3H), 3.87 (dd, J = 7.1, 7.1 Hz, 1H), 3.93 (dd, J = 8.7, 2.5 Hz, 1H), 4.09 (m, 2H), 4.98 (m, 2H), 6.95 (dd, J = 8.7, 2.5 Hz, 1H), 7.11 (d, J = 2.5 Hz, 1H), 7.71 (d, J = 8.7 Hz, 1H), 8.03 (s, 1H) |
| 85 | Ex. 5; microwave reaction, 1 h, 140° C., 75 W | com'l | 2-fluoro-4-[(1-{1-[4-oxo-1-(tetrahydro-2H-pyran-4-yl)-4,5-dihydro-1H-pyrazolo[3,4-d]pyrimidin-6-yl]ethyl}azetidin-3-yl)oxy]benzonitrile | 439.4, LCMS | ¹H NMR (400 MHz, CD₃OD) 1.37 (d, J = 6.6 Hz, 3H), 1.89 (m, 2H), 2.29 (m, 2H), 3.31 (m, 1H, assumed, obscured by solvent peak), 3.38 (dd, J = 8.3, 5.0 Hz, 1H), 3.62 (m, 3H), 3.87 (dd, J = 7.1, 7.1 Hz, 1H), 3.94 (dd, J = 7.0, 7.0 Hz, 1H), 4.09 (br d, J = 11.6 Hz, 2H), 4.97 (m, 2H), 6.85 (m, 2H), 7.66 (dd, J = 8.1, 8.1 Hz, 1H), 8.03 (s, 1H) |
| 86 | Ex. 5 | com'l | 3-[(1-{1-[4-oxo-1-(tetrahydro-2H-pyran-4-yl)-4,5-dihydro-1H-pyrazolo[3,4-d]pyrimidin-6-yl]ethyl}azetidin-3-yl)oxy]benzonitrile | 421.4, LCMS | ¹H NMR (400 MHz, CD₃OD) 1.37 (d, J = 6.6 Hz, 3H), 1.89 (m, 2H), 2.29 (m, 2H), 3.29 (m, 1H, assumed, obscured by solvent peak), 3.35 (dd, J = 8.2, 5.2 Hz, 1H), 3.61 (m, 3H), 3.87 (dd, J = 7.0, 7.0 Hz, 1H), 3.93 (dd, J = 7.0, 7.0 Hz, 1H), 4.08 (br d, J = 11.6 Hz, 2H), 4.95 (m, 2H), 7.16 (m, 2H), 7.31 (br d, J = 7.7 Hz, 1H), 7.45 (dd, J = 7.9, 7.9 Hz, 1H), 8.02 (s, 1H) |
| 87 | Ex. 18 | P3 | 1-cyclopentyl-6-{(1R)-1-[3-(3-fluorobenzyl)azetidin-1-yl]ethyl}-1,5-dihydro-4H-pyrazolo[3,4-d]pyrimidin-4-one | 398.1, LCMS | ¹H NMR (400 MHz, CDCl₃) 1.34 (d, J = 6.6 Hz, 3H), 1.72 (m, 2H), 1.97 (m, 2H), 2.10 (m, 4H), 3.22 (dd, J = 7.6, 5.9 Hz, 1H), 3.37 (dd, J = 7.4, 5.9 Hz, 1H), 3.54 (q, J = 6.7 Hz, 1H), 3.85 (m, 2H), 4.80 (m, 1H), 5.16 (m, 1H), 6.48 (ddd, J = 10.6, 2.3, 2.3 Hz, 1H), 6.55 (dd, J = 8.3, 2.1 Hz, 1H), 6.68 (ddd, J = 8.3, 8.3, 1.9 Hz, 1H), 7.21 (ddd, J = 8.3, 8.3, 6.8 Hz, 1H), 8.05 (s, 1H), 9.85 (br s, 1H) |

*com'l = commercially available side chain

The compounds of additional Examples 88-175 were prepared in accordance with the following Methods A through E, as indicated in Table 3 below.

Method A

Preparation of N-substituted 6-(1-aminoethyl)-1-cyclopentyl-1,5-dihydro-4H-pyrazolo[3,4-d]pyrimidin-4-ones

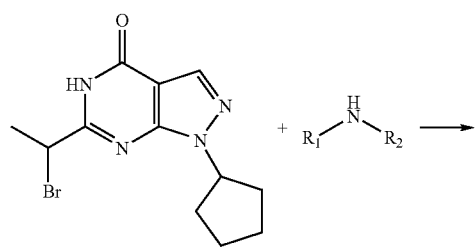

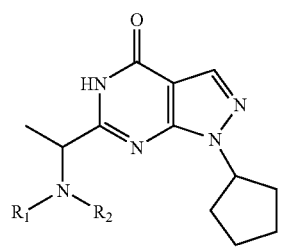

The amines (0.14 mmol) were weighed into vials and treated with a solution of 6-(1-bromoethyl)-1-cyclopentyl-1,5-dihydro-4H-pyrazolo[3,4-d]pyrimidin-4-one (22 mg, 0.07 mmol, prepared in a manner analogous to the synthesis of C25 in Example 5, except that C29 was used in place of C2) in a 1:5 mixture of DMF: acetonitrile (0.6 mL). Potassium carbonate (29 mg, 0.21 mmol) was added, and the reactions were shaken and heated at 82° C. for 8 h. The reactions were then cooled to room temperature and water (1.5 mL) and EtOAc (2.5 mL) were added. After vortexing the reactions, the organic portions were separated and passed through a short column of sodium sulfate. This process was repeated two times. The combined filtrates for each reaction were concentrated in vacuo, then treated with a 3% solution of trifluoroacetic acid in dichloromethane (0.5 mL). The mixtures were shaken for 15 mins, solvent removed in vacuo, and the crude samples were dissolved in DMSO (1 mL) and purified by preparative HPLC (column: Xterra PrepMS-$C_{18}$, 5 µm, 19×100 mm; Solvent A: 0.1% trifluoroacetic acid in water (v/v); Solvent B: acetonitrile; Gradient: 5% to 95% B), to afford the final Examples.

Method B

Preparation of N-substituted 6-[(1R)-1-aminoethyl]-1-cyclopentyl-1,5-dihydro-4H-pyrazolo[3,4-d]pyrimidin-4-ones

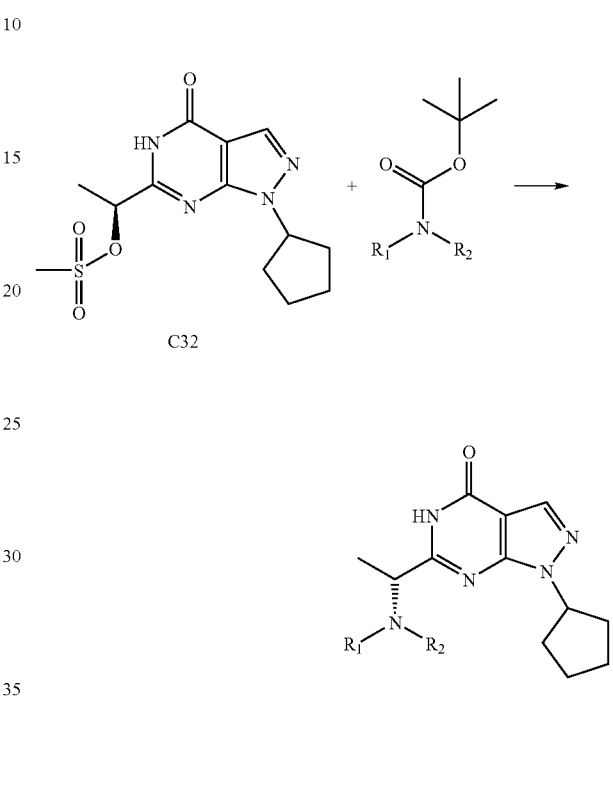

C32

The t-butoxycarbonyl-protected amines (0.1 mmol) were added to a solution of 1:1 trifluoroacetic acid: dichloromethane (0.75 mL) and shaken at room temperature for 18 h. The reactions were concentrated in vacuo and a 2.33 mM solution of triethylamine in 1:1 toluene: acetonitrile (0.15 mL) was added. Next, (1 S)-1-(1-cyclopentyl-4-oxo-4,5-dihydro-1H-pyrazolo[3,4-d]pyrimidin-6-yl)ethyl methanesulfonate (C32, 16.3 mg, 0.05 mmol) dissolved in 1:1 toluene: acetonitrile (0.6 mL) was added, and the reactions were heated to 90° C. for 8 h. The reactions were cooled to room temperature and left for 48 h, then 1N aqueous sodium hydroxide solution (1.5 mL) and EtOAc (2.2 mL) were added. The reactions were vortexed, and the organic layers were separated and loaded onto a strong cation-exchange solid phase extraction (SCX SPE) cartridge. The extraction process was repeated two times, followed by a final wash of the SPE column with EtOAc (5 mL). The crude products were released by eluting the columns with a solution of triethylamine in MeOH (1N, 6 mL). The eluants were concentrated in vacuo, dissolved in DMSO (1 mL) and purified by preparative HPLC (column: XBridge $C_{18}$, 5 µm; 19×100 mm; Solvent A: 0.03% ammonium hydroxide in water (v/v); Solvent B: 0.03% ammonium hydroxide in acetonitrile (v/v); Gradient: 15% to 95% B), to provide the final Examples.

Method C

Preparation of N-substituted 6-[(1R)-1-aminoethyl]-1-cyclopentyl-1,5-dihydro-4H-pyrazolo[3,4-d]pyrimidin-4-ones

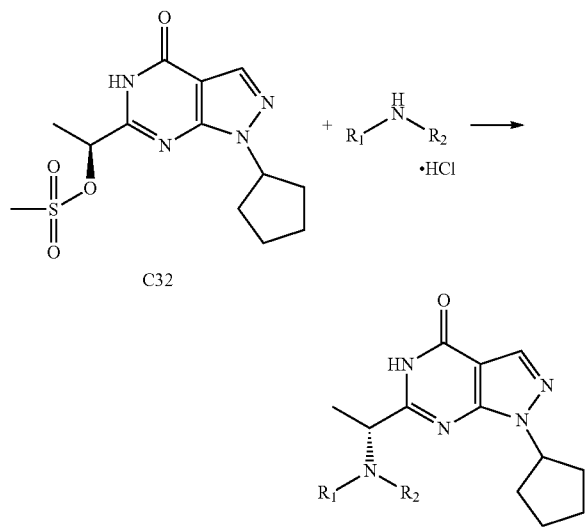

The amine hydrochloride salts (0.150 mmol) were dissolved in 1:1 dichloroethane: methanol (2.4 mL) and loaded onto SCX SPE columns. The source vials were rinsed with additional 1:1 dichloroethane: MeOH (2.4 mL), which was added to the column, and the columns were eluted with MeOH (4 mL). The free base of the amine was released by eluting the columns with triethylamine in MeOH (1N). These eluants were concentrated in vacuo and treated with a solution of triethylamine in 1:1 toluene: acetonitrile (0.83 mM, 0.15 mL). Next, a solution of C32 (16.3 mg, 0.05 mmol) in 1:1 toluene: acetonitrile (0.6 mL) was added and the reactions were heated to 90° C. for 8 h. The reactions were then shaken at room temperature for 18 h and an aqueous solution of sodium hydroxide (1N, 1.5 mL) and ethyl acetate (2.2 mL) was added. The reactions were vortexed, and the organics were separated and loaded onto SCX SPE columns. The extraction process was repeated two times, followed by a final wash of the column with EtOAc (5 mL). The crude products were released by eluting the columns with a solution of triethylamine in MeOH (1N, 6 mL). Solvent was removed in vacuo, and the residues were dissolved in DMSO (1 mL) and purified by one of the following preparative HPLC methods. Method 1 (column: XBridge $C_{18}$, 5 µm, 19×100 mm; Solvent A: 0.03% ammonium hydroxide in water (v/v); Solvent B: 0.03% ammonium hydroxide in acetonitrile (v/v) using an appropriate gradient); Method 2 (column: XBridge $C_{18}$, 5 µm, 19×100 mm; Solvent A: 0.05% trifluoroacetic acid in water (v/v); Solvent B: 0.05% trifluoroacetic acid in acetonitrile (v/v) using an appropriate gradient); Method 3 (column: Atlantis $dC_{18}$, 5 µm, 19×100 mm; Solvent A: 0.05% trifluoroacetic acid in water (v/v); Solvent B: 0.05% trifluoroacetic acid in acetonitrile (v/v) using an appropriate gradient), to provide the final Examples.

Method D

Preparation of O-substituted 6-[1-(3-hydroxyazetidin-1-yl)ethyl]-1-(tetrahydro-2H-pyran-4-yl)-1,5-dihydro-4H-pyrazolo[3,4-d]pyrimidin-4-ones

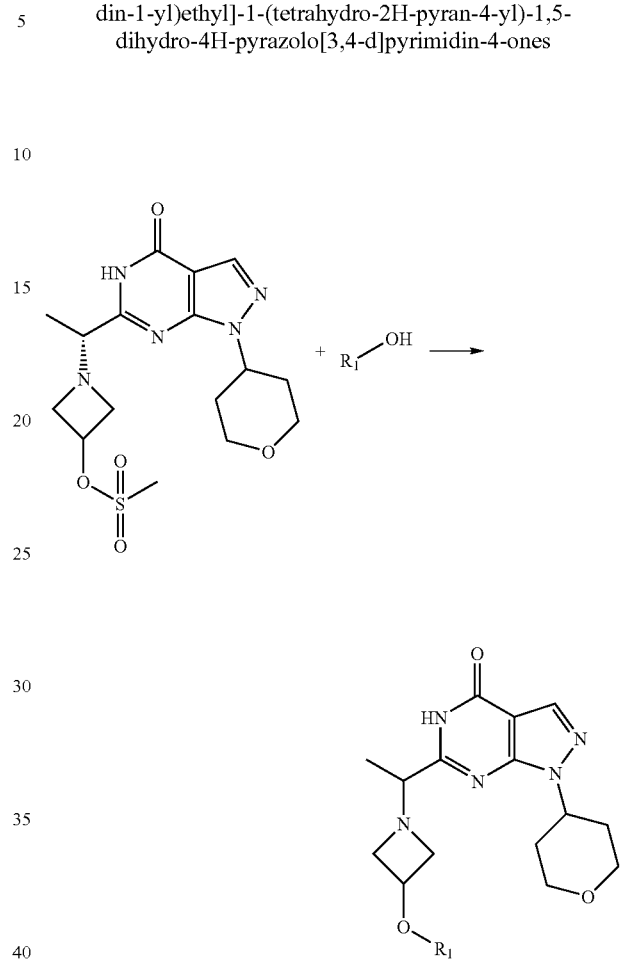

To the alcohols (0.1 mmol) was added 1-{(1R)-1-[4-oxo-1-(tetrahydro-2H-pyran-4-yl)-4,5-dihydro-1H-pyrazolo[3,4-d]pyrimidin-6-yl]ethyl}azetidin-3-yl methanesulfonate (20 mg, 0.05 mmol) in DMF (0.77 mL). Cesium carbonate (49 mg, 0.15 mmol) was added and the reactions were heated to 70° C. for 20 h. The reactions were cooled to room temperature and EtOAc (2 mL) was added, after which the reactions were heated to 35° C. and shaken. Reactions were centrifuged to segregate particulates, and 2.4 mL of the reaction mixtures was transferred to SCX-SPE columns. An additional 2.4 mL of EtOAc was added to the reaction vessel, and transferred to the SCX-SPE column. The columns were washed with MeOH (5 mL) and the desired products were then released by eluting with a solution of triethylamine in MeOH (6 mL). The solvent was removed in vacuo. A solution of trifluoroacetic acid in dichloromethane (10%, 0.5 mL) was added, and the mixtures were shaken for 15 mins. Solvents were removed in vacuo and the crude samples were dissolved in DMSO (0.6 mL) and purified using the conditions described for Method A, to afford the final Examples.

Method E

Preparation of O-substituted 6-[1-(3-hydroxyazetidin-1-yl)ethyl]-1-(tetrahydro-2H-pyran-4-yl)-1,5-dihydro-4H-pyrazolo[3,4-d]pyrimidin-4-ones

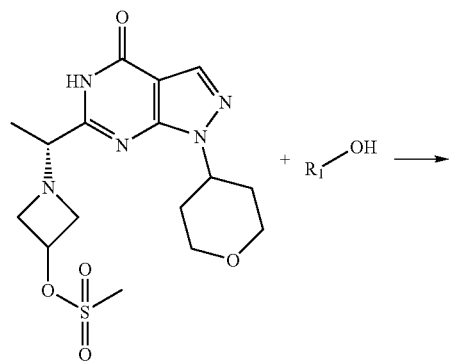

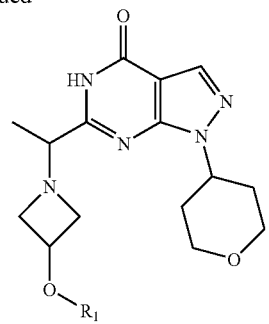

The products were synthesized by following the general procedure of Method D, except that 1-{(1R)-1-[4-oxo-1-(tetrahydro-2H-pyran-4-yl)-4,5-dihydro-1H-pyrazolo[3,4-d]pyrimidin-6-yl]ethyl}azetidin-3-yl methanesulfonate (20 mg, 0.05 mmol) was dissolved in 0.50 mL of acetonitrile instead of DMF, and potassium carbonate (21 mg, 0.15 mmol) was used in place of cesium carbonate. Compounds were purified using the conditions described for Method A, to provide the final Examples.

TABLE 3

| Ex. No. | Method | IUPAC Name | Retention Time (min.) | MS: Obs ion (M + 1) |
|---|---|---|---|---|
| 88 | A | 1-cyclopentyl-6-[1-(3-phenylpyrrolidin-1-yl)ethyl]-1,5-dihydro-4H-pyrazolo[3,4-d]pyrimidin-4-one, trifluoroacetate salt | 2.98a | 378.2 |
| 89 | A | 6-(1-azetidin-1-ylethyl)-1-cyclopentyl-1,5-dihydro-4H-pyrazolo[3,4-d]pyrimidin-4-one, trifluoroacetate salt | 2.41a | 288.2 |
| 90 | A | 1-cyclopentyl-6-{1-[(3R)-3-(2-methoxyphenoxy)pyrrolidin-1-yl]ethyl}-1,5-dihydro-4H-pyrazolo[3,4-d]pyrimidin-4-one, trifluoroacetate salt | 2.96a | 424.2 |
| 91 | A | 6-{1-[3-(2-chlorophenyl)pyrrolidin-1-yl]ethyl}-1-cyclopentyl-1,5-dihydro-4H-pyrazolo[3,4-d]pyrimidin-4-one, trifluoroacetate salt | 3.11a | 412.2 |
| 92 | A | 1-cyclopentyl-6-[1-(3-pyridin-4-ylpyrrolidin-1-yl)ethyl]-1,5-dihydro-4H-pyrazolo[3,4-d]pyrimidin-4-one, trifluoroacetate salt | 2.33a | 379.41 |
| 93 | D | 5-fluoro-2-[(1-{1-[4-oxo-1-(tetrahydro-2H-pyran-4-yl)-4,5-dihydro-1H-pyrazolo[3,4-d]pyrimidin-6-yl]ethyl}azetidin-3-yl)oxy]benzonitrile, trifluoroacetate salt | 2.57a | 439.1 |
| 94 | E | 6-{1-[3-(pyridin-3-yloxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 1.85a | 397.2 |
| 95 | E | 2-[(1-{1-[4-oxo-1-(tetrahydro-2H-pyran-4-yl)-4,5-dihydro-1H-pyrazolo[3,4-d]pyrimidin-6-yl]ethyl}azetidin-3-yl)oxy]benzonitrile, trifluoroacetate salt | 2.48a | 421.2 |
| 96 | E | 6-{1-[3-(2-chloro-4-methylphenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.79a | 444.2 |
| 97 | E | 6-{1-[3-(4-chloro-3-methylphenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.87a | 444.3 |
| 98 | D | 6-{1-[3-(isoquinolin-5-yloxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.06a | 447.2 |
| 99 | D | 6-{1-[3-(2,6-difluorophenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.54a | 432.1 |
| 100 | D | 6-{1-[3-(3-chloro-4-fluorophenoxy)azetidin-1-yl]ethyl}-1-(tetrahydro-2H-pyran-4-yl)-1,5-dihydro- | 2.77a | 448 |

TABLE 3-continued

| | | | | |
|---|---|---|---|---|
| | | 4H-pyrazolo[3,4-d]pyrimidin-4-one, trifluoroacetate salt | | |
| 101 | D | 6-{1-[3-(2-chloro-3,4-difluorophenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.82a | 466 |
| 102 | D | 6-{1-[3-(4-chloro-2-methylphenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.88a | 444.1 |
| 103 | D | 6-{1-[3-(2,5-dichlorophenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.81a | 464 |
| 104 | D | 3-fluoro-4-[(1-{1-[4-oxo-1-(tetrahydro-2H-pyran-4-yl)-4,5-dihydro-1H-pyrazolo[3,4-d]pyrimidin-6-yl]ethyl}azetidin-3-yl)oxy]benzonitrile, trifluoroacetate salt | 2.57a | 437.9 |
| 105 | D | 3-chloro-4-[(1-{1-[4-oxo-1-(tetrahydro-2H-pyran-4-yl)-4,5-dihydro-1H-pyrazolo[3,4-d]pyrimidin-6-yl]ethyl}azetidin-3-yl)oxy]benzonitrile, trifluoroacetate salt | 2.62a | 455.1 |
| 106 | D | 6-{1-[3-(quinolin-7-yloxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.12a | 447.1 |
| 107 | D | 6-{1-[3-(2,3-difluoro-4-methylphenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.79a | 446.1 |
| 108 | D | 6-{1-[3-(2-chlorophenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.67a | 430 |
| 109 | D | 2-chloro-3-fluoro-6-[(1-{1-[4-oxo-1-(tetrahydro-2H-pyran-4-yl)-4,5-dihydro-1H-pyrazolo[3,4-d]pyrimidin-6-yl]ethyl}azetidin-3-yl)oxy]benzonitrile, trifluoroacetate salt | 2.76a | 473.1 |
| 110 | D | 6-{1-[3-(2-fluorophenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.53a | 414.1 |
| 111 | D | 6-{1-[3-(2-chloro-5-methoxyphenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.72a | 460.1 |
| 112 | D | 6-{1-[3-(isoquinolin-7-yloxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.11a | 447.1 |
| 113 | D | 6-{1-[3-(4-chlorophenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.73a | 430.1 |
| 114 | D | 6-{1-[3-(3-chlorophenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.73a | 430.1 |
| 115 | D | 5-{1-[3-(3,5-difluorophenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.68a | 432.1 |
| 116 | D | 6-{1-[3-(2-fluoro-5-methylphenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.71a | 428.1 |
| 117 | D | 6-{1-[3-(4-tert-butylphenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 3.06a | 452.2 |
| 118 | D | 6-(1-{3-[(7-chloroquinolin-4-yl)oxy]azetidin-1-yl}ethyl)-1-(tetrahydro-2H-pyran-4-yl)-1,5-dihydro-4H-pyrazolo[3,4-d]pyrimidin-4-one, trifluoroacetate salt | 2.47a | 481 |
| 119 | D | 6-{1-[3-(3-chloro-2-fluorophenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.76a | 448 |
| 120 | D | 6-(1-{3-[(4-fluoro-2,3-dihydro-1-benzofuran-7-yl)oxy]azetidin-1-yl}ethyl)-1-(tetrahydro-2H-pyran- | 2.64a | 456.1 |

TABLE 3-continued

| | | | | |
|---|---|---|---|---|
| | | 4-yl)-1,5-dihydro-4H-pyrazolo[3,4-d]pyrimidin-4-one, trifluoroacetate salt | | |
| 121 | D | 6-{1-[3-(2-chloro-6-fluorophenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.64a | 448.1 |
| 122 | D | 1-(tetrahydro-2H-pyran-4-yl)-6-(1-{3-[4-(trifluoromethyl)phenoxy]azetidin-1-yl}ethyl)-1,5-dihydro-4H-pyrazolo[3,4-d]pyrimidin-4-one, trifluoroacetate salt | 2.87a | 464.1 |
| 123 | D | 6-{1-[3-(2,4-difluorophenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.63a | 432.1 |
| 124 | D | 6-{1-[3-(2-chloro-4,5-difluorophenoxy)azetidin-1-yl]ethyl}1-(tetrahydro-2H-pyran-4-yl)-1,5-dihydro-4H-pyrazolo[3,4-d]pyrimidin-4-one, trifluoroacetate salt | 2.79a | 466 |
| 125 | D | 1-(tetrahydro-2H-pyran-4-yl)-6-(1-{3-[3-(trifluoromethyl)phenoxy]azetidin-1-yl}ethyl)-1,5-dihydro-4H-pyrazolo[3,4-d]pyrimidin-4-one, trifluoroacetate salt | 2.84a | 464.1 |
| 126 | D | 6-{1-[3-(2,5-difluorophenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.61a | 432.1 |
| 127 | D | 1-(tetrahydro-2H-pyran-4-yl)-6-{1-[3-(2,3,4-trifluorophenoxy)azetidin-1-yl]ethyl}-1,5-dihydro-4H-pyrazolo[3,4-d]pyrimidin-4-one, trifluoroacetate salt | 2.73a | 450 |
| 128 | D | 6-{1-[3-(2-chloro-4-fluorophenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.73a | 448 |
| 129 | D | 5-chloro-2-[(1-{1-[4-oxo-1-(tetrahydro-2H-pyran-4-yl)-4,5-dihydro-1H-pyrazolo[3,4-d]pyrimidin-6-yl]ethyl}azetidin-3-yl)oxy]benzonitrile, trifluoroacetate salt | 2.7a | 455.1 |
| 130 | D | 2-chloro-6-fluoro-3-[(1-{1-[4-oxo-1-(tetrahydro-2H-pyran-4-yl)-4,5-dihydro-1H-pyrazolo[3,4-d]pyrimidin-6-yl]ethyl}azetidin-3-yl)oxy]benzonitrile, trifluoroacetate salt | 2.72a | 473.1 |
| 131 | D | 6-{1-[3-(2,3-dichlorophenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.83a | 464 |
| 132 | D | 1-(tetrahydro-2H-pyran-4-yl)-6-(1-{3-[3-(trifluoromethoxy)phenoxy]azetidin-1-yl}ethyl)-1,5-dihydro-4H-pyrazolo[3,4-d]pyrimidin-4-one, trifluoroacetate salt | 2.91a | 480.1 |
| 133 | D | 1-(tetrahydro-2H-pyran-4-yl)-6-{1-[3-(3,4,5-trifluorophenoxy)azetidin-1-yl]ethyl}-1,5-dihydro-4H-pyrazolo[3,4-d]pyrimidin-4-one, trifluoroacetate salt | 2.76a | 450 |
| 134 | D | 1-(tetrahydro-2H-pyran-4-yl)-6-{1-[3-(2,4,5-trifluorophenoxy)azetidin-1-yl]ethyl}-1,5-dihydro-4H-pyrazolo[3,4-d]pyrimidin-4-one, trifluoroacetate salt | 2.68a | 450.1 |
| 135 | D | 6-{1-[3-(4-chloro-2-fluorophenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.76a | 448 |
| 136 | D | 6-{1-[3-(5-fluoro-2-methylphenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.75a | 428.1 |
| 137 | D | 6-{1-[3-(3-fluoro-5-methoxyphenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.7a | 444.1 |
| 138 | D | 6-{1-[3-(3,4-difluoro-2-methylphenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.82a | 446.1 |
| 139 | D | 6-{1-[3-(2-chloro-6-methylphenoxy)azetidin-1-yl]ethyl}-1-(tetrahydro-2H-pyran-4-yl)-1,5-dihydro-4H-pyrazolo[3,4-d]pyrimidin-4-one, trifluoroacetate salt | 2.76a | 444 |
| 140 | B | (3aR,9bR)-2-[(1R)-1-(1-cyclopentyl-4-oxo-4,5-dihydro-1H-pyrazolo[3,4-d]pyrimidin-6-yl)ethyl]- | 2.51b | 419.1 |

TABLE 3-continued

| | | | | |
|---|---|---|---|---|
| | | 1,2,3,3a,5,9b-hexahydro-4H-pyrrolo[3,4-c]quinolin-4-one | | |
| 141 | B | 6-{(1R)-1-[3-(6-bromopyridin-2-yl)pyrrolidin-1-yl]ethyl}-1-cyclopentyl-1,5-dihydro-4H-pyrazolo[3,4-d]pyrimidin-4-one | 3.06e | 457 |
| 142 | B | (3aR,9bR)-8-chloro-2-[(1R)-1-(1-cyclopentyl-4-oxo-4,5-dihydro-1H-pyrazolo[3,4-d]pyrimidin-6-yl)ethyl]-1,2,3,3a,5,9b-hexahydro-4H-pyrrolo[3,4-c]quinolin-4-one | 2.57b | 453 |
| 143 | C | 1-cyclopentyl-6-[(1R)-1-(3-phenylpyrrolidin-1-yl)ethyl]-1,5-dihydro-4H-pyrazolo[3,4-d]pyrimidin-4-one | 2.28c | 378.2 |
| 144 | C | 1-cyclopentyl-6-{(1R)-1-[3-(2,3-dimethoxyphenyl)pyrrolidin-1-yl]ethyl}-1,5-dihydro-4H-pyrazolo[3,4-d]pyrimidin-4-one | 2.33c | 438.2 |
| 145 | C | 4-({1-[(1R)-1-(1-cyclopentyl-4-oxo-4,5-dihydro-1H-pyrazolo[3,4-d]pyrimidin-6-yl)ethyl]azetidin-3-yl}oxy)benzonitrile | 2.15c | 405.1 |
| 146 | C | 1-cyclopentyl-6-{(1R)-1-[3-(3-methylphenoxy)azetidin-1-yl]ethyl}-1,5-dihydro-4H-pyrazolo[3,4-d]pyrimidin-4-one | 2.39c | 394.2 |
| 147 | C | 1-cyclopentyl-6-{(1R)-1-[3-(3-methoxyphenoxy)azetidin-1-yl]ethyl}-1,5-dihydro-4H-pyrazolo[3,4-d]pyrimidin-4-one | 2.29c | 410.2 |
| 148 | C | 1-cyclopentyl-6-{(1R)-1-[3-(3-methoxyphenyl)-3-methylpyrrolidin-1-yl]ethyl}-1,5-dihydro-4H-pyrazolo[3,4-d]pyrimidin-4-one | 2.39c | 422.2 |
| 149 | C | 6-{(1R)-1-[3-(2-chlorophenyl)pyrrolidin-1-yl]ethyl}-1-cyclopentyl-1,5-dihydro-4H-pyrazolo[3,4-d]pyrimidin-4-one | 2.42c | 412.1 |
| 150 | C | 1-cyclopentyl-6-{(1R)-1-[3-(2-fluorophenyl)pyrrolidin-1-yl]ethyl}-1,5-dihydro-4H-pyrazolo[3,4-d]pyrimidin-4-one | 2.31c | 396.1 |
| 151 | C | 1-cyclopentyl-6-{(1R)-1-[3-(4-fluorophenyl)pyrrolidin-1-yl]ethyl}-1,5-dihydro-4H-pyrazolo[3,4-d]pyrimidin-4-one | 2.35c | 396.1 |
| 152 | C | 6-{(1R)-1-[3-(3-chlorophenyl)pyrrolidin-1-yl]ethyl}-1-cyclopentyl-1,5-dihydro-4H-pyrazolo[3,4-d]pyrimidin-4-one | 2.46c | 412.1 |
| 153 | C | 1-cyclopentyl-6-[(1R)-1-(3-pyridin-4-ylpyrrolidin-1-yl)ethyl]-1,5-dihydro-4H-pyrazolo[3,4-d]pyrimidin-4-one | 1.47c | 379.1 |
| 154 | C | 1-cyclopentyl-6-{(1R)-1-[(3R)-3-(2-methylphenoxy)pyrrolidin-1-yl]ethyl}-1,5-dihydro-4H-pyrazolo[3,4-d]pyrimidin-4-one | 2.45c | 408.2 |
| 155 | C | 6-{(1R)-1-[3-(3-chlorophenoxy)azetidin-1-yl]ethyl}-1-cyclopentyl-1,5-dihydro-4H-pyrazolo[3,4-d]pyrimidin-4-one | 2.44c | 414 |
| 156 | C | 6-{(1S)-1-[(3R)-3-(2-chlorophenoxy)pyrrolidin-1-yl]ethyl}-1-cyclopentyl-1,5-dihydro-4H-pyrazolo[3,4-d]pyrimidin-4-one | 2.41c | 428.1 |
| 157 | C | 1-cyclopentyl-6-{(1R)-1-[3-(pyridin-3-yloxy)azetidin-1-yl]ethyl}-1,5-dihydro-4H-pyrazolo[3,4-d]pyrimidin-4-one | 1.5c | 381.1 |
| 158 | C | 1-cyclopentyl-6-{(1R)-1-[3-(2,5-dichlorophenoxy)azetidin-1-yl]ethyl}-1,5-dihydro-4H-pyrazolo[3,4-d]pyrimidin-4-one | 2.52c | 448.1 |
| 159 | C | 4-{1-[(1R)-1-(1-cyclopentyl-4-oxo-4,5-dihydro-1H-pyrazolo[3,4-d]pyrimidin-6-yl)ethyl]pyrrolidin-3-yl}-N,N-dimethylbenzamide | 1.92c | 449.2 |
| 160 | C | 1-cyclopentyl-6-{(1R)-1-[3-(2,5-dimethoxyphenyl)pyrrolidin-1-yl]ethyl}-1,5-dihydro-4H-pyrazolo[3,4-d]pyrimidin-4-one | 2.38c | 438.2 |
| 161 | C | 1-cyclopentyl-6-{(1R)-1-[(3R)-3-(2-methoxyphenoxy)pyrrolidin-1-yl]ethyl}-1,5-dihydro-4H-pyrazolo[3,4-d]pyrimidin-4-one | 2.24c | 424.1 |
| 162 | C | 6-[(1R)-1-(3-benzylazetidin-1-yl)ethyl]-1-cyclopentyl-1,5-dihydro-4H-pyrazolo[3,4-d]pyrimidin-4-one | 2.31c | 378.2 |
| 163 | C | N-cyclobutyl-3-{1-[(1R)-1-(1-cyclopentyl-4-oxo-4,5-dihydro-1H-pyrazolo[3,4-d]pyrimidin-6-yl)ethyl]pyrrolidin-3-yl}benzamide | 2.24c | 475.2 |
| 164 | C | 1-cyclopentyl-6-{(1R)-1-[3-(3,4-difluorophenoxy)azetidin-1-yl]ethyl}-1,5-dihydro-4H-pyrazolo[3,4-d]pyrimidin-4-one | 2.28d | 416.1 |
| 165 | C | 6-{(1R)-1-[3-(4-chlorophenoxy)azetidin-1-yl]ethyl}-1-cyclopentyl-1,5-dihydro-4H-pyrazolo[3,4-d]pyrimidin-4-one | 2.35d | 414.1 |

TABLE 3-continued

| 166 | C | 1-cyclopentyl-6-{(1R)-1-[3-(4-methoxyphenoxy)azetidin-1-yl]ethyl}-1,5-dihydro-4H-pyrazolo[3,4-d]pyrimidin-4-one | 2.13d | 410.1 |
|---|---|---|---|---|
| 167 | C | 1-cyclopentyl-6-{(1R)-1-[(3S)-3-(2-methoxyphenoxy)pyrrolidin-1-yl]ethyl}-1,5-dihydro-4H-pyrazolo[3,4-d]pyrimidin-4-one | 2.13d | 424.1 |
| 168 | C | 2-({(3R)-1-[(1R)-1-(1-cyclopentyl-4-oxo-4,5-dihydro-1H-pyrazolo[3,4-d]pyrimidin-6-yl)ethyl]pyrrolidin-3-yl}oxy)bezonitrile | 2.1d | 419.1 |
| 169 | C | 1-cyclopentyl-6-[(1R)-1-{3-[4-(trifluoromethyl)phenoxy]azetidin-1-yl}ethyl]-1,5-dihydro-4H-pyrazolo[3,4-d]pyrimidin-4-one | 2.47d | 448.1 |
| 170 | C | methyl (3R,4S)-1-[(1R)-1-(1-cyclopentyl-4-oxo-4,5-dihydro-1H-pyrazolo[3,4-d]pyrimidin-6-yl)ethyl]-4-(4-fluorophenyl)pyrrolidine-3-carboxylate | 2.37c | 454.1 |
| 171 | C | 1-cyclopentyl-6-{(1R)-1-[(3S,4R)-3-methoxy-4-phenylpyrrolidin-1-yl]ethyl}-1,5-dihydro-4H-pyrazolo[3,4-d]pyrimidin-4-one | 2.32c | 408.2 |
| 172 | C | 1-cyclopentyl-6-[(1R)-1-{3-[3-(trifluoromethyl)phenoxy]azetidin-1-yl}ethyl]-1,5-dihydro-4H-pyrazolo[3,4-d]pyrimidin-4-one | 2.55c | 448.1 |
| 173 | C | 6-{(1R)-1-[3-(2-chloro-5-fluorophenoxy)azetidin-1-yl]ethyl}-1-cyclopentyl-1,5-dihydro-4H-pyrazolo[3,4-d]pyrimidin-4-one | 2.43c | 432.2 |
| 174 | C | 1-[(1R)-1-(1-cyclopentyl-4-oxo-4,5-dihydro-1H-pyrazolo[3,4-d]pyrimidin-6-yl)ethyl]spiro[azetidine-3,2'-chromen]-4'(3'H)-one | 2.15c | 420.1 |
| 175 | C | 1-cyclopentyl-6-{(1R)-1-[3-(4-fluorophenoxy)azetidin-1-yl]ethyl}-1,5-dihydro-4H-pyrazolo[3,4-d]pyrimidin-4-one | 2.3c | 398.1 |

[a]Column: Waters Xterra MS C18 3.0 × 50 mm, 5 μm; Mobile phase A: 0.1% TFA in water (v/v); Mobile phase B: Acetonitrile; flow rate 1.6 mL/min
Gradient:

| 0 minutes | 5% B |
|---|---|
| 0.1 minutes | 5% B |
| 5.0 minutes | 95% B |
| 6.0 minutes | 95% B |

[b]Column: Xbridge Phenyl 4.6 × 50 mm, 5 μm; Mobile phase A: 0.03% $NH_4OH$ in water (v/v); Mobile phase B: 0.03% $NH_4OH$ in acetonitrile (v/v); Flow rate 2 mL/mi
Gradient:

| 0 minutes | 5% B |
|---|---|
| 4 minutes | 95% B |
| 5 minutes | 95% B |

[c]Column: Atlantis dC18 4.6 × 50 mm, 5 μm; Mobile phase A: 0.1% TFA in water (v/v); Mobile phase B: 100% acetonitrile; flow rate 2 mL/min
Gradient:

| 0 minutes | 5% B |
|---|---|
| 4 minutes | 95% B |
| 5 minutes | 95% B |

[d]Column: Symmetry C8 4.6 × 50 mm, 5 μm; Mobile phase A: 0.1% TFA in water (v/v); Mobile phase B: 100% acetonitrile; flow rate 2 mL/min
Gradient:

| 0 minutes | 5% B |
|---|---|
| 4.0 minutes | 80% B |
| 5.0 minutes | 80% B |

[e]Column: Symmetry C8 4.6 × 50 mm, 5 μm; Mobile phase A: 0.03% $NH_4OH$ in water (v/v); Mobile phase B: 0.03% $NH_4OH$ in acetonitrile (v/v); flow rate 2 mL/min
Gradient:

| 0 minutes | 5% B |
|---|---|
| 4.0 minutes | 95% B |
| 5.0 minutes | 95% B |

Biological Protocols

The utility of the compounds of Formula (I), and the pharmaceutically acceptable salts thereof, in the treatment or prevention of diseases (such as are detailed herein) in mammals (e.g., humans) may be demonstrated by the activity thereof in conventional assays known to one of ordinary skill in the art, including the assays described below. Such assays also provide a means whereby the activities of the compounds of Formula (I) can be compared with the activities of other known compounds.

Phosphodiesterase 9 (PDE9) Inhibitory Activity

PDE9 $IC_{50}$, 384-well assay: Test compounds were solubilized in 100% dimethyl sulfoxide and diluted to the required concentrations in 15% dimethyl sulfoxide/water. The PDE9A enzyme was thawed slowly and diluted in 50 mM Tris HCl buffer (pH 7.5 at room temperature) containing 1.3 mM $MgCl_2$. Incubations were initiated by the addition of PDE9A enzyme to 384-well plates containing test drugs and radioligand (50 nM $^3$H-cGMP). After a thirty minute incubation at room temperature, 10 μM 6-benzyl-1-cyclopentyl-1,5-dihydro-4H-pyrazolo[3,4-d]pyrimidin-4-one was added to each well of the plate to stop the reaction. Phosphodiesterase SPA beads (Amersham/GE) were then added to the assay plate at a concentration of 0.2 mg/well. Activity of test compounds was assessed by measuring the amount of $^3$H-5'GMP resulting from enzyme cleavage of $^3$H-cGMP radioligand. Levels of $^3$H-5'GMP bound to SPA beads were determined by paralux counting of the assay plates in a Microbeta Trilux Counter (PerkinElmer). Non-specific binding was determined by radioligand binding in the presence of a saturating, concentration of 6-benzyl-1-cyclopentyl-1,5-dihydro-4H-pyrazolo[3,4-d]pyrimidin-4-one (10 μM). The $IC_{50}$ value of each test compound (concentration at which 50% inhibition of specific binding occurs) was calculated by non-linear regression (curve fitting) of the concentration-response and is shown in Table 4 below.

PDE9 $IC_{50}$, 96-well assay: The assay was performed using the Phosphodiesterase Scintillation Proximity (SPA) assay (GE Healthcare Life Sciences). The assay was carried out in 96 well clear bottom microtiter plates (Costar 3632, Corning Inc). The human recombinant PDE9 enzyme was generated in SF-9 cells, the cell pellets were sonicated in buffer (20 mM Tris, 2 mM benzamidine, 1 mM EDTA, 250 mM sucrose, 100 μM PMSF, pH 7.5 with HCl), centrifuged at 40,000×g for 20 min at 4° C. The supernatants were stored at −80° C. [8-$^3$H] guanosine 3',5'-cyclic phosphate (TRK 392, GE Healthcare Life Sciences) was diluted in assay buffer (50 mM Tris-HCl, pH7.5, containing 1.3 mM $MgCl_2$) such that the final well concentration was 50 nM. Test compounds were dissolved in DMSO, diluted in DI $H_2O$ and serially diluted in 20% DMSO/80% $H_2O$, for a final concentration of 2% DMSO. For the assay the PDE9 was diluted with assay buffer such that 20% or less of the substrate was hydrolyzed to 5'GMP. Each assay well contained 10 μL of test compound or solvent, 40 μl of [$^3$H]cGMP and 50 μl of enzyme, background was determined by a high concentration of a PDE inhibitor. The assay was initiated with the addition of the enzyme and carried out at room temperature for 30 min. The assay was terminated with the addition of 10 μL of a PDE9 inhibitor that was sufficient to totally inhibit the enzyme activity, immediately followed by the addition of 50 μL per well of SPA beads. The plates were sealed, vortexed, allowed to set for >300 min, then counted in a Wallac TriLux MicroBeta LSC. The $IC_{50}$ value of each test compound is shown in Table 4 below.

TABLE 4

| Ex. No. | PDE9 $IC_{50}$, 384-well assay (μM) | PDE9 $IC_{50}$, 96-well assay (μM) |
|---|---|---|
| 1 | 0.0866 | N.D. |
| 2 | 0.00971* | N.D. |
| 3 | N.D. | 0.0373* |
| 4 | N.D. | 0.0817 |
| 5 | N.D. | 0.02 |
| 6 | 0.0324* | N.D. |
| 7 | 0.00224* | N.D. |
| 8 | 0.00933* | N.D. |
| 9 | 0.01218* | 0.0107 |
| 10 | 0.0202* | N.D. |
| 11 | 0.0254* | 0.0824 |
| 12 | 0.0404* | N.D. |
| 13 | N.D. | 0.00949 |
| 14 | N.D. | 0.136 |
| 15 | N.D. | 0.211 |
| 16 | N.D. | 0.047* |
| 17 | N.D. | 0.0156* |
| 18 | 0.0503* | N.D. |
| 19 | 0.0418* | N.D. |
| 20 | 0.0274 | N.D. |
| 21 | 0.0437* | N.D. |
| 22 | 0.0419* | N.D. |
| 23 | 0.0282* | N.D. |
| 24 | 0.0343* | N.D. |
| 25 | 0.043* | N.D. |
| 26 | 0.0319* | N.D. |
| 27 | 0.0539* | N.D. |
| 28 | 0.0424* | N.D. |
| 29 | 0.0633* | N.D. |
| 30 | 0.0596* | N.D. |
| 31 | 0.0127* | N.D. |
| 32 | 0.0219* | N.D. |
| 33 | 0.0127* | N.D. |
| 34 | 0.00781* | N.D. |
| 35 | 0.169* | N.D. |
| 36 | 0.237* | N.D. |
| 37 | N.D. | 0.032 |
| 38 | 0.0225* | 0.0125* |
| 39 | 0.0298* | N.D. |
| 40 | 0.066* | N.D. |
| 41 | 0.0518* | N.D. |
| 42 | 0.0325* | N.D. |
| 43 | 0.0146* | N.D. |
| 44 | 0.0851* | N.D. |
| 45 | 0.18* | N.D. |
| 46 | 0.025* | N.D. |
| 47 | 0.0312* | N.D. |
| 48 | 0.0186* | N.D. |
| 49 | 0.0198* | N.D. |
| 50 | 0.0105* | N.D. |
| 51 | 0.0115* | N.D. |
| 52 | 0.032* | N.D. |
| 53 | 0.0258* | N.D. |
| 54 | N.D. | 0.0702 |
| 55 | N.D. | 0.0211* |
| 56 | N.D. | 0.00537* |
| 57 | 0.0671* | 0.222* |
| 58 | N.D. | 0.0225 |
| 59 | N.D. | 0.0105* |
| 60 | 0.0332* | N.D. |
| 61 | N.D. | 0.0245* |
| 62 | N.D. | 0.0165* |
| 63 | N.D. | 0.0429 |
| 64 | N.D. | 0.245 |
| 65 | N.D. | 0.256 |
| 66 | N.D. | 0.216 |
| 67 | 0.0735* | 0.0399* |
| 68 | 0.00847* | 0.00294* |
| 69 | N.D. | 0.0453 |
| 70 | N.D. | 0.0572 |
| 71 | N.D. | 0.00463 |
| 72 | N.D. | 0.0228 |
| 73 | N.D. | 0.0594 |
| 74 | N.D. | 0.00745 |
| 75 | N.D. | 0.0202 |
| 76 | N.D. | 0.0138 |
| 77 | N.D. | 0.0272* |
| 78 | N.D. | 0.00541 |
| 79 | N.D. | 0.00456 |
| 80 | N.D. | 0.00381* |
| 81 | N.D. | 0.0892 |
| 82 | N.D. | 0.0503 |
| 83 | 0.0132* | 0.0314 |

TABLE 4-continued

| Ex. No. | PDE9 IC$_{50}$, 384-well assay (µM) | PDE9 IC$_{50}$, 96-well assay (µM) |
|---|---|---|
| 84 | N.D. | 0.0132 |
| 85 | N.D. | 0.0348* |
| 86 | N.D. | 0.0241* |
| 87 | 0.0555* | N.D. |
| 88 | N.D. | 0.23* |
| 89 | N.D. | 0.593* |
| 90 | N.D. | 0.211* |
| 91 | N.D. | 0.148* |
| 92 | N.D. | 0.382* |
| 93 | N.D. | 0.0694 |
| 94 | N.D. | 0.31 |
| 95 | N.D. | 0.0283 |
| 96 | N.D. | 0.0142 |
| 97 | N.D. | 0.0233 |
| 98 | N.D. | 0.0156 |
| 99 | N.D. | 0.112 |
| 100 | N.D. | 0.0638 |
| 101 | N.D. | 0.0488 |
| 102 | N.D. | 0.0845 |
| 103 | N.D. | 0.0309 |
| 104 | N.D. | 0.0332 |
| 105 | N.D. | 0.0426 |
| 106 | N.D. | 0.0214 |
| 107 | N.D. | 0.0472 |
| 108 | N.D. | 0.0521 |
| 109 | N.D. | 0.0301 |
| 110 | N.D. | 0.148 |
| 111 | N.D. | 0.0344 |
| 112 | N.D. | 0.0583 |
| 113 | N.D. | 0.0882 |
| 114 | N.D. | 0.0856 |
| 115 | N.D. | 0.0404 |
| 116 | N.D. | 0.0908 |
| 117 | N.D. | 0.234 |
| 118 | N.D. | 0.0404 |
| 119 | N.D. | 0.0449 |
| 120 | N.D. | 0.0701 |
| 121 | N.D. | 0.0911 |
| 122 | N.D. | 0.107 |
| 123 | N.D. | 0.211 |
| 124 | N.D. | 0.0646 |
| 125 | N.D. | 0.0436 |
| 126 | N.D. | 0.0574 |
| 127 | N.D. | 0.11 |
| 128 | N.D. | 0.0745 |
| 129 | N.D. | 0.0447 |
| 130 | N.D. | 0.0362 |
| 131 | N.D. | 0.0223 |
| 132 | N.D. | 0.0489 |
| 133 | N.D. | 0.0514 |
| 134 | N.D. | 0.102 |
| 135 | N.D. | 0.0991 |
| 136 | N.D. | 0.119 |
| 137 | N.D. | 0.0324 |
| 138 | N.D. | 0.0787 |
| 139 | N.D. | 0.215 |
| 140 | 0.292 | N.D. |
| 141 | 0.0617 | N.D. |
| 142 | 0.763 | N.D. |
| 143 | 0.273 | N.D. |
| 144 | 0.0729 | N.D. |
| 145 | 0.0248* | N.D. |
| 146 | 0.0572* | N.D. |
| 147 | 0.0243* | N.D. |
| 148 | 0.568 | N.D. |
| 149 | 0.321 | N.D. |
| 150 | 0.517* | N.D. |
| 151 | 0.41 | N.D. |
| 152 | 0.35 | N.D. |
| 153 | 0.174 | N.D. |
| 154 | 0.661 | N.D. |
| 155 | 0.155 | N.D. |
| 156 | 0.292 | N.D. |
| 157 | 0.0289* | N.D. |
| 158 | 0.248* | N.D. |
| 159 | 0.332 | N.D. |
| 160 | 0.151 | N.D. |
| 161 | 0.216 | N.D. |
| 162 | 0.0348* | N.D. |
| 163 | 0.0533* | N.D. |
| 164 | 0.125 | N.D. |
| 165 | 0.184 | N.D. |
| 166 | 0.0172* | N.D. |
| 167 | 0.915 | N.D. |
| 168 | 0.336 | N.D. |
| 169 | 0.713 | N.D. |
| 170 | 0.693 | N.D. |
| 171 | 0.913 | N.D. |
| 172 | 0.335 | N.D. |
| 173 | 0.153 | N.D. |
| 174 | 0.0617 | N.D. |
| 175 | 0.0612 | N.D. |

N.D. = not done
*Value represents the geometric mean of 2-8 IC$_{50}$ determinations All references cited throughout this specification are expressly incorporated herein by reference.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

We claim:

1. A compound of Formula (I),

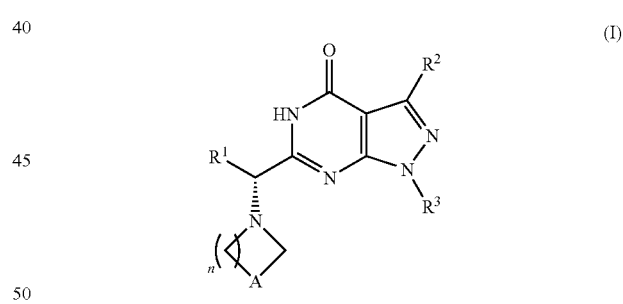

(I)

or a pharmaceutically acceptable salt thereof, wherein:
R$^1$ is selected from the group consisting of
(i) hydrogen,
(ii) (C$_1$-C$_4$)alkyl,
(iii) (C$_2$-C$_4$)alkenyl,
(iv) (C$_2$-C$_4$)alkynyl,
(v) (C$_1$-C$_4$)alkoxy,
(vi) (C$_1$-C$_4$)haloalkyl,
(vii) (C$_3$-C$_6$)cycloalkyl, optionally substituted with one to three substituents, the substituents being independently selected from the group consisting of (C$_1$-C$_4$)alkyl, (C$_1$-C$_4$)alkoxy, halo, (C$_1$-C$_4$)haloalkyl, (C$_1$-C$_4$)haloalkoxy, cyano, carboxy, and carbamoyl,
(viii) 4 to 10 member heterocycloalkyl, optionally substituted with one to three substituents, the substituents being independently selected from the group consisting of $(C_1-C_4)$alkyl, $(C_1-C_4)$alkoxy, halo, $(C_1-C_4)$haloalkyl, $(C_1-C_4)$ haloalkoxy, cyano, carboxy, and carbamoyl,
(ix) aryl, optionally substituted with one to three substituents, the substituents being independently selected from the group consisting of $(C_1-C_4)$alkyl, $(C_1-C_4)$alkoxy, halo, $(C_1-C_4)$haloalkyl, $(C_1-C_4)$ haloalkoxy, cyano, carboxy, and carbamoyl, and
(x) heteroaryl, optionally substituted with one to three substituents, the substituents being independently selected from the group consisting of $(C_1-C_4)$alkyl, $(C_1-C_4)$alkoxy, halo, $(C_1-C_4)$haloalkyl, $(C_1-C_4)$haloalkoxy, cyano, carboxy, and carbamoyl;
$R^2$ is selected from the group consisting of hydrogen, $(C_1-C_4)$alkyl, $(C_1-C_4)$ haloalkyl, cyano, and $(C_3-C_6)$cycloalkyl;
$R^3$ is selected from the group consisting of $(C_1-C_6)$alkyl, $(C_2-C_6)$alkenyl, $(C_2-C_6)$ alkynyl, $(C_3-C_8)$cycloalkyl, heterocycloalkyl, aryl, and heteroaryl, each of which optionally may be substituted with one to three substituents, the substituents being independently selected from the group consisting of $(C_1-C_4)$alkyl, $(C_1-C_4)$alkoxy, halo, and $(C_1-C_4)$haloalkyl;
n is 1 or 2;
A is —$CR^4R^5$— or —$CHR^a$—$CHR^b$—;
$R^4$ is selected from the group consisting of
(i) hydrogen,
(ii) $(C_1-C_7)$alkyl,
(iii) $(C_3-C_8)$cycloalkyl,
(iv) 4 to 10 member heterocycloalkyl,
(v) aryl, optionally substituted with one to three substituents, the substituents being independently selected from the group consisting of $(C_1-C_4)$alkyl, $(C_1-C_4)$alkoxy, halo, $(C_1-C_4)$haloalkyl, $(C_1-C_4)$haloalkoxy, $(C_3-C_6)$ cycloalkyl, cyano, carboxy, and carbamoyl,
(vi) heteroaryl, optionally substituted with one to three substituents, the substituents being independently selected from the group consisting of $(C_1-C_4)$ alkyl, $(C_1-C_4)$ alkoxy, halo, $(C_1-C_4)$haloalkyl, $(C_1-C_4)$haloalkoxy, $(C_3-C_6)$cycloalkyl, cyano, carboxy, and carbamoyl, and
(vii) $LR^6$, wherein:
L is selected from the group consisting of —$CH_2$—, —$NR^7$—, and —O—;
$R^6$ is aryl, heteroaryl, $(C_1-C_8)$alkyl, $(C_3-C_8)$cycloalkyl, 4 to 10 member heterocycloalkyl, or $(C_1-C_6)$alkoxy, each of which optionally may be substituted with one to three substituents, the substituents being independently selected from the group consisting of $(C_1-C_4)$ alkyl, $(C_1-C_4)$ alkoxy, halo, $(C_1-C_4)$haloalkyl, $(C_1-C_4)$haloalkoxy, $(C_3-C_6)$cycloalkyl, cyano, carboxy, and carbamoyl; and
$R^7$ is hydrogen, methyl or ethyl;
$R^5$ is selected from the group consisting of hydrogen, hydroxyl, $(C_1-C_4)$alkoxy, halogen, and $(C_1-C_6)$alkyl; or $R^4$ and $R^5$, together with the carbon to which they are attached, form a cycloalkyl or heterocycloalkyl ring that optionally incorporates an oxo group and is optionally substituted with $(C_1-C_8)$alkyl, $(C_3-C_8)$ cycloalkyl, halo, $(C_1-C_8)$ alkoxy, or $(C_1-C_3)$haloalkyl;
$R^a$ is $(C_1-C_4)$alkoxy or $R^8$—O—C(O)—, wherein $R^8$ is $(C_1-C_4)$alkyl; and
$R^b$ is aryl, heteroaryl, or heterocycloalkyl, optionally substituted with halo, $(C_1-C_8)$ alkyl, $(C_3-C_8)$cycloalkyl, $(C_1-C_8)$alkoxy, or $(C_1-C_3)$ haloalkyl; or $R^a$ and $R^b$, together with the carbons to which they are attached, form a cycloalkyl or heterocycloalkyl ring that optionally incorporates an oxo group and is optionally substituted with $(C_1-C_8)$ alkyl, $(C_3-C_8)$ cycloalkyl, halo, $(C_1-C_8)$alkoxy, or $(C_1-C_3)$haloalkyl.

2. The compound of claim 1, wherein:
$R^1$ is selected from the group consisting of
(i) $(C_1-C_4)$alkyl,
(ii) $(C_3-C_6)$cycloalkyl,
(iii) $(C_1-C_4)$haloalkyl,
(iv) 4 to 10 member heterocycloalkyl, optionally substituted with one to three substituents, the substituents being independently selected from the group consisting of $(C_1-C_4)$alkyl, $(C_1-C_4)$alkoxy, halo, $(C_1-C_4)$haloalkyl, $(C_1-C_4)$ haloalkoxy, cyano, carboxy, and carbamoyl,
(v) aryl, optionally substituted with one to three substituents, the substituents being independently selected from the group consisting of $(C_1-C_4)$alkyl, $(C_1-C_4)$alkoxy, halo, $(C_1-C_4)$haloalkyl, $(C_1-C_4)$haloalkoxy, cyano, carboxy, and carbamoyl, and
(vi) heteroaryl, optionally substituted with one to three substituents, the substituents being independently selected from the group consisting of $(C_1-C_4)$alkyl, $(C_1-C_4)$alkoxy, halo, $(C_1-C_4)$ haloalkoxy, cyano, carboxy, and carbamoyl;
$R^2$ is selected from the group consisting of hydrogen, $(C_1-C_4)$alkyl, $(C_1-C_4)$ haloalkyl, cyano, and cyclopropyl;
$R^4$ is selected from the group consisting of
(i) hydrogen,
(ii) aryl, optionally substituted with one to three substituents, the substituents being independently selected from the group consisting of $(C_1-C_4)$alkyl, $(C_1-C_4)$alkoxy, halo, $(C_1-C_4)$haloalkyl, $(C_1-C_4)$haloalkoxy, $(C_3-C_6)$ cycloalkyl, cyano, carboxy, and carbamoyl,
(iii) heteroaryl, optionally substituted with one to three substituents, the substituents being independently selected from the group consisting of $(C_1-C_4)$ alkyl, $(C_1-C_4)$ alkoxy, halo, $(C_1-C_4)$haloalkyl, $(C_1-C_4)$haloalkoxy, $(C_3-C_6)$cycloalkyl, cyano, carboxy, and carbamoyl, and
(iv) $LR^6$, wherein:
L is selected from the group consisting of —$CH_2$—, —$NR^7$—, and —O—; and
$R^6$ is aryl or heteroaryl, each of which optionally may be substituted with one to three substituents, the substituents being independently selected from the group consisting of $(C_1-C_4)$alkyl, $(C_1-C_4)$alkoxy, halo, $(C_1-C_4)$ haloalkyl, $(C_1-C_4)$haloalkoxy, $(C_3-C_6)$cycloalkyl, cyano, carboxy, and carbamoyl;
$R^5$ is selected from the group consisting of hydrogen, hydroxyl, $(C_1-C_4)$alkoxy, halo, and $(C_1-C_6)$alkyl; or $R^4$ and $R^5$, together with the carbon to which they are attached, form a cyclic ketone; and
$R^b$ is aryl or heteroaryl, optionally substituted with halo, $(C_1-C_3)$ alkyl, or $(C_1-C_3)$ haloalkyl; or $R^a$ and $R^b$, together with the carbons to which they are attached, form a cycloalkyl or heterocycloalkyl ring that optionally incorporates an oxo group and is optionally substituted with $(C_1-C_8)$alkyl, $(C_3-C_8)$cycloalkyl, halo, $(C_1-C_8)$alkoxy, or $(C_1-C_3)$ haloalkyl.

3. The compound of claim 2, or a pharmaceutically acceptable salt thereof, wherein:
$R^1$ is $(C_1-C_4)$alkyl, $(C_3-C_6)$cycloalkyl, or phenyl;
$R^2$ is hydrogen;
$R^3$ is selected from the group consisting of isopropyl, cyclobutyl, cyclopentyl, tetrahydrofuranyl, and tetrahydropyranyl;
A is —$CR^4R^5$—; and
L is —$CH_2$— or —O—.

4. The compound of claim 3, or a pharmaceutically acceptable salt thereof, wherein:
   $R^1$ is methyl, ethyl, cyclopropyl or phenyl;
   $R^4$ is selected from the group consisting of hydrogen, phenyl, pyridinyl, pyrimidinyl, quinolinyl, pyrazinyl, pyridazinyl, phthalazinyl, quinazolinyl, naphthyridinyl, quinoxalinyl, isoquinolinyl, benzofuranyl, dihydrobenzofuranyl, each of which optionally may be substituted with one to three substituents, the substituents being independently selected from the group consisting of $(C_1-C_4)$alkyl, $(C_1-C_4)$alkoxy, halo, $(C_3-C_6)$cycloalkyl, carbamoyl, and $LR^6$;
   $R^5$ is selected from the group consisting of hydrogen, methyl, hydroxy, and halo; or $R^4$ and $R^5$, together with the carbon to which they are attached form benzopyranone; and
   $R^6$ is phenyl, pyrimidinyl, pyridinyl, pyrazinyl, quinoxalinyl, phthalazinyl, pyridazinyl, quinazolinyl, naphthyridinyl, isoquinolinyl, quinolinyl, benzofuranyl, each of which optionally may be substituted with one to three substitutents, the substitutents being independently selected from the group consisting of $(C_1-C_4)$alkyl, $(C_1-C_4)$alkoxy, halo, $(C_1-C_4)$haloalkyl, $(C_1-C_4)$haloalkoxy, and cyano.

5. The compound of claim 4, or a pharmaceutically acceptable salt thereof, wherein:
   $R^1$ is methyl or ethyl;
   n is 1;
   $R^3$ is cyclopentyl or tetrahydro-2H-pyranyl;
   $R^4$ is pyrimidinyl or $LR^6$;
   $R^5$ is hydrogen, methyl, hydroxy, or fluoro;
   L is —O—; and
   $R^6$ is optionally substituted phenyl.

6. The compound of claim 1, or a pharmaceutically acceptable salt thereof, wherein:
   $R^1$ is methyl, ethyl, cyclopropyl or phenyl;
   $R^2$ is hydrogen;
   $R^3$ is selected from the group consisting of isopropyl, cyclobutyl, cyclopentyl, and tetrahydro-2H-pyran-4-yl;
   n is 1;
   A is —$CHR^a$—$CHR^b$—;
   $R^a$ is methoxy or $R^8$—O—C(O)—, wherein $R^8$ is methyl; and
   $R^b$ is phenyl, optionally substituted with halo; or $R^a$ and $R^b$, together with the carbons to which they are attached, form a dihydroquinolone, optionally substituted with halo.

7. The compound of claim 1, selected from the group consisting of:
   1-cyclopentyl-6-[(1R)-1-(3-pyrimidin-2-ylazetidin-1-yl)ethyl]-1,5-dihydro-4H-pyrazolo [3,4-d]pyrimidin-4-one;
   1-cyclopentyl-6-{(1R)-1-[3-(pyrimidin-2-yloxy)azetidin-1-yl]ethyl}-1,5-dihydro-4H-pyrazolo [3,4-d]pyrimidin-4-one;
   1-cyclopentyl-6-[(1R)-1-(3-pyridin-2-ylazetidin-1-yl)ethyl]-1,5-dihydro-4H-pyrazol [3,4-d]pyrimidin-4-one;
   1-cyclopentyl-6-[(1R)-1-(3-pyridin-4-ylazetidin-1-yl)ethyl]-1,5-dihydro-4H-pyrazolo [3,4-d]pyrimidin-4-one;
   1-cyclopentyl-6-[(1R)-1-(3-pyridin-3-ylazetidin-1-yl)ethyl]-1,5-dihydro-4H-pyrazolo [3,4-d]pyrimidin-4-one;
   1-cyclopentyl-6-[(1R)-1-(3-pyrimidin-5-ylazetidin-1-yl)ethyl]-1,5-dihydro-4H-pyrazolo [3,4-d]pyrimidin-4-one;
   1-cyclopentyl-6-[(1R)-1-(3-pyridazin-3-ylazetidin-1-yl)ethyl]-1,5-dihydro-4H-pyrazolo [3,4-d]pyrimidin-4-one;
   1-cyclopentyl-6-{(1R)-1-[3(pyrimidin-5-ylmethyl)azetidin-1-yl]ethyl}-1,5-dihydro-4H-pyrazolo [3,4-d]pyrimidin-4-one;
   1-cyclopentyl-6-[(1R)-1-(3-pyrimidin-4-ylazetidin-1-yl)ethyl]-1,5-dihydro-4H-pyrazolo [3,4-d]pyrimidin-4-one;
   1-cyclopentyl-6-{(1R)-1-[3-(2-methylpyrimidin-4-yl)azetidin-1-yl]ethyl}-1,5-dihydro-4H-pyrazolo [3,4-d]pyrimidin-4-one;
   1-cyclopentyl-6-[(1R)-1-(3-quinolin-2-ylazetidin-1-yl)ethyl]-1,5-dihydro-4H-pyrazolo [3,4-d]pyrimidin-4-one;
   1-cyclopentyl-6-{(1R)-1-[(3R)-3-(pyrimidin-2-yloxy)pyrrolidin-1-yl]ethyl}-1,5-dihydro-4H-pyrazolo [3,4-d]pyrimidin-4-one;
   1-cyclopentyl-6-{(1R)-1-[(3S)-3-(pyrimidin-2-yloxy)pyrrolidin-1-yl]ethyl}-1,5-dihydro-4H-pyrazolo [3,4-d]pyrimidin-4-one;
   1-cyclopentyl-6-[(1R)-1-{3-[(6-methylpyridin-3-yl)methyl]azetidin-1-yl}ethyl]-1,5-dihydro-4H-pyrazolo [3,4-d]pyrimidin-4-one;
   1-cyclopentyl-6-[(1R)-1-(3-pyrimidin-2-ylpyrrolidin-1-yl)ethyl]-1,5-dihydro-4H-pyrazolo [3,4-d]pyrimidin-4-one;
   1-cyclopentyl-6-{(1R)-1-[3-(5-methylpyrimidin-2-yl)azetidin-1-yl]ethyl}-1,5-dihydro-4H-pyrazolo [3,4-d]pyrimidin-4-one;
   1-cyclopentyl-6-{(1R)-1-[3-(5-cyclopropylpyrimidin-2-yl)azetidin-1-yl]ethyl}-1,5-dihydro-4H-pyrazolo [3,4-d]pyrimidin-4-one;
   1-cyclopentyl-6-{(1R)-1-[3-(4,6-dimethylpyrimidin-2-yl)azetidin-1-yl]ethyl}-1,5-dihydro-4H-pyrazolo [3,4-d]pyrimidin-4-one;
   1-cyclopentyl-6-{(1R)-1-[3-(4-methylpyrimidin-2-yl)azetidin-1-yl]ethyl}-1,5-dihydro-4H-pyrazolo [3,4-d]pyrimidin-4-one;
   1-cyclopentyl-6-{(1R)-1-[3-(3fluorobenzyl)azetidin-1-yl]ethyl}-1,5-dihydro-4H-pyrazolo [3,4-d]pyrimidin-4-one;
   (3aR,9bR)-2-[(1R)-1-(1-cyclopentyl-4-oxo-4,5-dihydro-1H-pyrazolo[3,4-d]pyrimidin-6-yl)ethyl]-1,2,3,3a,5,9b-hexahydro-4H-pyrrolo[3,4-c]quinolin-4-one;
   6-{(1R)-1-[3-(6-bromopyridin-2-yl)pyrrolidin-1-yl]ethyl}-1-cyclopentyl-1,5-dihydro-4H-pyrazolo [3,4-d]pyrimidin-4-one;
   (3aR,9bR)-8-chloro-2-[(1R)-1-(1-cyclopentyl-4-oxo-4,5-dihydro-1H-pyrazolo[3,4-d]pyrimidin-6-yl)ethyl]-1,2,3,3a,5,9b-hexahydro-4H-pyrrolo[3,4-c]quinolin-4-one;
   1-cyclopentyl-6-[(1R)-1-(3-phenylpyrrolidin-1-yl)ethyl]-1,5-dihydro-4H-pyrazolo [3,4-d]pyrimidin-4-one;
   1-cyclopentyl-6-{(1R)-1-[3-(2,3-dimethoxyphenyl)pyrrolidin-1-yl]ethyl}-1,5-dihydro-4H-pyrazolo [3,4-d]pyrimidin-4-one;
   4-({1-[(1R)-1-(1-cyclopentyl-4-oxo-4,5-dihydro-1H-pyrazolo[3,4-d]pyrimidin-6-yl)ethyl]azetidin-3-yl}oxy)benzonitrile;
   1-cyclopentyl-6-{(1R)-1-[3-(3-methylphenoxy)azetidin-1-yl]ethyl}-1,5-dihydro-4H-pyrazolo [3,4-d]pyrimidin-4-one;
   1-cyclopentyl-6-{(1R)-1-[3-(3-methoxyphenoxy)azetidin-1-yl]ethyl}-1,5-dihydro-4H-pyrazolo [3,4-d]pyrimidin-4-one;

1-cyclopentyl-6-{(1R)-1-[3-(3-methoxyphenyl)-3-methylpyrrolidin-1-yl]ethyl}-1,5-dihydro-4H-pyrazolo [3,4-d]pyrimidin-4-one;

6-{(1R)-1-[3-(2-chlorophenyl)pyrrolidin-1-yl]ethyl}-1-cyclopentyl-1,5-dihydro-4H-pyrazolo [3,4-d]pyrimidin-4-one;

1-cyclopentyl-6-{(1R)-1-[3-(2-fluorophenyl)pyrrolidin-1-yl]ethyl}-1,5-dihydro-4H-pyrazolo [3,4-d]pyrimidin-4-one;

1-cyclopentyl-6-{(1R)-1-[3-(4-fluorophenyl)pyrrolidin-1-yl]ethyl}-1,5-dihydro-4H-pyrazolo [3,4-d]pyrimidin-4-one;

6-{(1R)-1-[3-(3-chlorophenyl)pyrrolidin-1-yl]ethyl}-1-cyclopentyl-1,5-dihydro-4H-pyrazolo [3,4-d]pyrimidin-4-one;

1-cyclopentyl-6-[(1R)-1-(3-pyridin-4-ylpyrrolidin-1-yl)ethyl]-1,5-dihydro-4H-pyrazolo [3,4-d]pyrimidin-4-one;

1-cyclopentyl-6-{(1R)-1-[(3R)-3-(2-methylphenoxy)pyrrolidin-1-yl]ethyl}-1,5-dihydro-4H-pyrazolo [3,4-d]pyrimidin-4-one;

6-{(1R)-1-[3-(3-chlorophenoxy)azetidin-1-yl]ethyl}-1-cyclopentyl-1,5-dihydro-4H-pyrazolo [3,4-d]pyrimidin-4-one;

6-{(1S)-1-[(3R)-3-(2-chlorophenoxy)pyrrolidin-1-yl]ethyl}-1-cyclopentyl-1,5-dihydro-4H-pyrazolo [3,4-d]pyrimidin-4-one;

1-cyclopentyl-6-{(1R)-1-[3-(pyridin-3-yloxy)azetidin-1-yl]ethyl}-1,5-dihydro-4H-pyrazolo [3,4-d]pyrimidin-4-one;

1-cyclopentyl-6-{(1R)-1-[3-(2,5-dichlorophenoxy)azetidin-1-yl]ethyl}-1,5-dihydro-4H-pyrazolo [3,4-d]pyrimidin-4-one;

4-{1-[(1R)-1-(1-cyclopentyl-4-oxo-4,5-dihydro-1H-pyrazolo [3,4-d]pyrimidin-6-yl) ethyl]pyrrolidin-3-yl}—N,N-dimethylbenzamide;

1-cyclopentyl-6-{(1R)-1-[3-(2,5-dimethcmphenyl)pyrrolidin-1-yl]ethyl}-1,5-dihydro-4H-pyrazolo [3,4-d]pyrimidin-4-one;

1-cyclopentyl-6-{(1R)-1-[(3R)-3-(2-methoxphenoxy)pyrrolidin-1-yl]ethyl}-1,5-dihydro-4H-pyrazolo [3,4-d]pyrimidin-4-one;

6-[(1R)-1-(3-benzylazetidin-1-yl)ethyl]-1-cyclopentyl-1,5-dihydro-4H-pyrazolo[3,4-d]pyrimidin-4-one;

N-cyclobutyl-3-{1-[(1R)-1-(1-cyclopentyl-4-oxo-4,5-dihydro-1H-pyrazolo[3,4-d]pyrimidin-6-yl)ethyl]pyrrolidin-3-yl}benzamide;

1-cyclopentyl-6-{(1R)-1-[3-(3,4-difluorophenoxy)azetidin-1-yl]ethyl}-1,5-dihydro-4H-pyrazolo [3,4-d]pyrimidin-4-one;

6-{(1R)-1-[3-(4-chlorophenoxy)azetidin-1-yl]ethyl}-1-cyclopentyl-1,5-dihydro-4H-pyrazolo [3,4-d]pyrimidin-4-one;

1-cyclopentyl-6-{(1R)-1-[3-(4-methoxyphenoxy)azetidin-1-yl]ethyl}-1,5-dihydro-4H-pyrazolo [3,4-d]pyrimidin-4-one;

1-cyclopentyl-6-{(1R)-1-[(3S)-3-(2-methoxyphenoxy)pyrrolidin-1-yl]ethyl}-1,5-dihydro-4H-pyrazolo [3,4-d]pyrimidin-4-one;

2-({(3R)-1-[(1R)-1-(1-cyclopentyl-4-oxo-4,5-dihydro-1H-pyrazolo[3,4-d]pyrimidin-6-yl)ethyl]pyrrolidin-3-yl}oxy)benzonitrile;

1-cyclopentyl-6-[(1R)-1-{3-[4-(trifluoromethyl)phenoxy]azetidin-1-yl}ethyl]-1, 5-dihydro-4H-pyrazolo [3,4-d]pyrimidin-4-one;

methyl(3R,4S)-1-[(1R)-1-(1-cyclopentyl-4-oxo-4,5-dihydro-1H-pyrazolo[3,4-d]pyrimidin-6-yl)ethyl]-4-(4-fluorophenyl)pyrrolidine-3-carboxylate;

1-cyclopentyl-6-{(1R)-1-[(3S,4R)-3-methoxy-4-phenylpyrrolidin-1-yl]ethyl}-1,5-dihydro-4H-pyrazolo [3,4-d]pyrimidin-4-one;

1-cyclopentyl-6-[(1R)-1-{3[3-(trifluoromethyl)phenoxy]azetidin-1-yl}ethyl]-1,5-dihydro-4H-pyrazolo [3,4-d]pyrimidin-4-one;

6-{(1R)-1-[3-(2-chloro-5-fluorophenoxy)azetidin-1-yl]ethyl}-1-cyclopentyl-1,5-dihydro-4H-pyrazolo [3,4-d]pyrimidin-4-one;

1-[(1R)-1-(1-cyclopentyl-4-oxo-4,5-dihydro-1H-pyrazolo[3,4-d]pyrimidin-6-yl)ethyl]spiro[azetidine-3,2'-chromen]-4'(3'H)-one;

1-cyclopentyl-6-{(1R)-1-[3-(4-fluorophenoxy)azetidin-1-yl]ethyl}-1,5-dihydro-4H-pyrazolo [3,4-d]pyrimidin-4-one;

or a pharmaceutically acceptable salt thereof.

8. The compound of claim 1, selected from the group consisting of:

6-{(1R)-1-[3-(4-methylpyridin-2-yl)azetidin-1-yl]ethyl}-1-(tetrahydro-2H-pyran-4-yl)-1,5-dihydro-4H-pyrazolo [3,4-d]pyrimidin-4-one;

6-[cyclopropyl(3-phenoxyazetidin-1-yl)methyl]-1-(tetrahydro-2H-pyran-4-yl)-1,5-dihydro-4H-pyrazolo [3,4-d]pyrimidin-4-one;

2-fluoro-5-[(1-{1-[4-oxo-1-(tetrahydro-2H-pyran-4-yl)-4,5-dihydro-1H-pyrazolo[3,4-d]pyrimidin-6-yl]ethyl}azetidin-3-yl)oxy]benzonitrile;

6-[(1R)-1-(3-quinolin-2-ylazetidin-1-yl)ethyl]-1-(tetrahydro-2H-pyran-4-yl)-1,5-dihydro-4H-pyrazolo [3,4-d]pyrimidin-4-one;

6-{(1R)-1-[3-(6-methylpyridin-2-yl)azetidin-1-yl]ethyl}-1-(tetrahydro-2H-pyran-4-yl)-1,5-dihydro-4H-pyrazolo [3,4-c]pyrimidin-4-one;

6-{(1R)-1-[3-(4-fluorophenoxy)azetidin-1-yl]ethyl}-1-(tetrahydro-2H-pyran-4-yl)-1,5-dihydro-4H-pyrazolo [3,4-d]pyrimidin-4-one;

6-{(1R)-1-[3-(5-chloropyrimidin-2-yl)azetidin-1-yl]ethyl}-1-(tetrahydro-2H-pyran-4-yl)-1,5-dihydro-4H-pyrazolo [3,4-d]pyrimidin-4-one;

6-[(1R)-1-(3-phenylazetidin-1-yl)ethyl]-1-(tetrahydro-2H-pyran-4-yl)-1,5-dihydro-4H-pyrazolo [3,4-d]pyrimidin-4-one;

6-[(1R)-1-(3-pyrazin-2-ylazetidin-1-yl)ethyl]-1-(tetrahydro-2H-pyran-4-yl)-1,5-dihydro-4H-pyrazolo [3,4-d]pyrimidin-4-one;

6-[(1R)-1-(3-pyrimidin-2-ylazetidin-1-yl)ethyl]-1-(tetrahydro-2H-pyran-4-yl)-1,5-dihydro-4H-pyrazolo [3,4-d]pyrimidin-4-one;

6-[(1R)-1-(3-pyridin-2-ylazetidin-1-yl)ethyl]-1-(tetrahydro-2H-pyran-4-yl)-1,5-dihydro-4H-pyrazolo [3,4-d]pyrimidin-4-one;

6-[(1R)-1-(3-pyridin-4-ylazetidin-1-yl)ethyl]-1-(tetrahydro-2H-pyran-4-yl)-1,5-dihydro-4H-pyrazolo [3,4-d]pyrimidin-4-one;

6-[(1R)-1-(3-pyridin-3-ylazetidin-1-yl)ethyl]-1-(tetrahydro-2H-pyran-4-yl)-1,5-dihydro-4H-pyrazolo [3,4-d]pyrimidin-4-one;

6-[(1R)-1-(3-pyrimidin-5-ylazetidin-1-yl)ethyl]-1-(tetrahydro-2H-pyran-4-yl)-1,5-dihydro-4H-pyrazolo [3,4-d]pyrimidin-4-one;

6-[(1R)-1-(3-pyridazin-3-ylazetidin-1-yl)ethyl]-1-(tetrahydro-2H-pyran-4-yl)-1,5-dihydro-4H-pyrazolo [3,4-d]pyrimidin-4-one;

6-{(1R)-1-[3-(2-methylpyrimidin-4-yl)azetidin-1-yl]ethyl}-1-(tetrahydro-2H-pyran-4-yl)-1,5-dihydro-4H-pyrazolo [3,4-d]pyrimidin-4-one;

6-{(1R)-1-[3-(3-fluorobenzyl)azetidin-1-yl]ethyl}-1-(tetrahydro-2H-pyran-4-yl)-1,5-dihydro-4H-pyrazolo [3,4-d]pyrimidin-4-one;

6-[(1R)-1-(3-phenoxyazetidin-1-ypethyl]-1-(tetrahydro-2H-pyran-4-yl)-1,5-dihydro-4H-pyrazolo [3,4-d]pyrimidin-4-one;

6-{(1R)-1-[3-(6-methylpyridin-2-yl)azetidin-1-yl]propyl}-1-(tetrahydro-2H-pyran-4-yl )-1,5-dihydro-4H-pyrazolo [3,4-d]pyrimidin-4-one;

6-[(1-(3-pyridin-2-ylazetidin-1-yl)propyl]-1-(tetrahydro-2H-pyran-4-yl)-1,5-dihydro-4H-pyrazolo [3,4-d]pyrimidin-4-one;

6-{(1R)-1-[3-(5-methylpyrimidin-2-yl)azetidin-1-yl]propyl}-1-(tetrahydro-2H-pyran-4-yl)-1,5-dihydro-4H-pyrazolo [3,4-d]pyrimidin-4-one;

6-{(1R)-1-[3-(5-chloropyrimidin-2-yl)azetidin-1-yl]propyl}-1-(tetrahydro-2H-pyran-4-yl)-1,5-dihydro-4H-pyrazolo [3,4-d]pyrimidin-4-one;

6-{(1R)-1-[3-(pyrimidin-2-ylmethyl)azetidin-1-yl]ethyl}-1-(tetrahydro-2H-pyran-4-yl)-1,5-dihydro-4H-pyrazolo [3,4-d]pyrimidin-4-one;

6-{(1R)-1-[3-(5-methylpyrimidin-2-yl)azetidin-1-yl]ethyl}-1-(tetrahydro-2H-pyran-4-yl-1,5-dihydro-4H-pyrazolo [3,4-d]pyrimidin-4-one;

6-{(1R)-1-[3-(5-cyclopropylpyrimidin-2-yl)azetidin-1-yl]ethyl}-1-(tetrahydro-2H-pyran-4-yl)-1,5-dihydro-4H-pyrazolo [3,4-d]pyrimidin-4-one;

6-{(1R)-1-[3-(4,6-dimethylpyrimidin-2-yl)azetidin-1-yl]ethyl}-1-(tetrahydro-2H-pyran-4-yl)-1,5-dihydro-4H-pyrazolo [3,4-d]pyrimidin-4-one; and 6-{(1R)-1-[3-(4-methylpyrimidin-2-yl)azetidin-1-yl]ethyl}-1-(tetrahydro-2H-pyran-4-yl)-1,5-dihydro-4H-pyrazolo [3,4-d]pyrimidin-4-one;

or a pharmaceutically acceptable salt thereof.

9. The compound of claim 1, selected from the group consisting of:

1-cyclobutyl-6-{(1R)-1-[3-(pyrimidin-2yloxy)azetidin-1-yl]ethyl}-1,5-dihydro-4H-pyrazolo [3,4-d]pyrimidin-4-one; and 1-isopropyl-6-[1-(3-phenoxyazetidin-1-yl)ethyl]-1,5-dihydro-4H-pyrazolo[3,4-d]pyrimidin-4-one;

or a pharmaceutically acceptable salt thereof.

10. A compound of formula I,

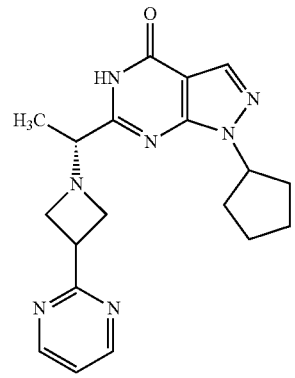

or a pharmaceutically acceptable salt thereof.

11. A pharmaceutical composition comprising a compound according to claim 1, or a pharmaceutically acceptable salt thereof, and a pharmaceutically acceptable vehicle, carrier or diluent.

* * * * *